United States Patent
Konno et al.

(10) Patent No.: US 6,770,644 B1
(45) Date of Patent: Aug. 3, 2004

(54) HYDROXAMIC ACID DERIVATIVES, PROCESS FOR THE PRODUCTION THEREOF AND DRUG CONTAINING THE SAME AS THE ACTIVE INGREDIENT

(75) Inventors: Mitoshi Konno, Mishima-gun (JP); Katsuhito Sakaki, Mishima-gun (JP); Masao Naka, Mishima-gun (JP); Mikio Konishi, Mishima-gun (JP); Tadamitsu Kishimoto, Tondabayashi (JP)

(73) Assignee: Ono Pharmaceuticals Co., Ltd., Osaka (JP)

( * ) Notice: Subject to any disclaimer, the term of this patent is extended or adjusted under 35 U.S.C. 154(b) by 0 days.

(21) Appl. No.: 10/088,821

(22) PCT Filed: Sep. 22, 2000

(86) PCT No.: PCT/JP00/06506

§ 371 (c)(1),
(2), (4) Date: Mar. 22, 2002

(87) PCT Pub. No.: WO01/21583

PCT Pub. Date: Mar. 29, 2001

(30) Foreign Application Priority Data

Sep. 24, 1999 (JP) .......................................... 11-270459
Jul. 7, 2000 (JP) ...................................... 2000-206649

(51) Int. Cl.[7] .................. A61K 31/5375; C07D 413/02
(52) U.S. Cl. .............................. 514/236.8; 514/254.02; 514/326; 514/575; 544/137; 544/168; 544/367; 544/393; 546/209; 546/234; 562/621
(58) Field of Search ................................. 544/137, 168, 544/367, 393; 546/209, 234; 562/621; 514/236.8, 254.02, 326, 575

(56) References Cited

U.S. PATENT DOCUMENTS 4,769,461 A 9/1988 Musser et al.
5,804,601 A 9/1998 Kato et al.

FOREIGN PATENT DOCUMENTS

EP 737671 A2 10/1996
JP 59-46244 3/1984

OTHER PUBLICATIONS

CAS–ONLINE Registry No. 331232–28–1, Entry Date Apr. 13, 2001.*
International Search Report.

* cited by examiner

Primary Examiner—Joseph K. McKane
Assistant Examiner—Kamal Saeed
(74) Attorney, Agent, or Firm—Sughrue Mion, PLLC

(57) ABSTRACT

Hydroxamic acid derivatives of the formula (I)

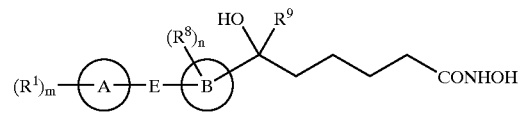

(wherein all the symbols have the same meaning as defined in the specification.),
non-toxic salt thereof or prodrugs thereof.

The compounds of the formula (I) inhibit producing IL-6, so it may be used for the prevention and/or treatment of various inflammatory diseases, sepsis, multiple myeloma, plasma cell leukemia, osteoporosis, cachexia, psoriasis, nephritis, renal cell carcinoma, Kaposi's sarcoma, rheumatoid arthritis, hypergammaglobulinemia, Castleman's disease, atrial myxoma, diabetes mellitus, autoimmune diseases, hepatitis, colitis, graft versus host disease, infectious diseases and endometriosis.

7 Claims, No Drawings

HYDROXAMIC ACID DERIVATIVES, PROCESS FOR THE PRODUCTION THEREOF AND DRUG CONTAINING THE SAME AS THE ACTIVE INGREDIENT

TECHNICAL FIELD

The present invention relates to hydroxamic acid derivatives, the methods for preparation thereof and inhibitors of interleukin-6 production comprising thereof, as an active ingredient.

More particularly, it relates to (1) inhibitors of IL-6 production comprising hydroxamic acid derivatives of the formula (I)

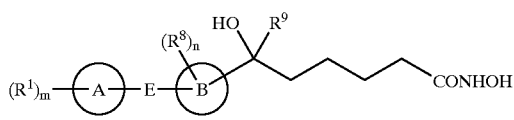

(wherein all the symbols have the same meaning as defined hereinafter), non-toxic salts thereof and prodrugs thereof, as an active ingredient,
(2) novel hydroxamic acid derivatives of the above formula (I), non-toxic salts thereof and prodrugs thereof and
(3) the methods for preparation of hydroxamic acid derivatives of the above formula (I), non-toxic salts thereof and prodrugs thereof.

BACKGROUND

Cytokine is a multifunctional factor which plays an important role in the host defense system of living body and it relates to various life phenomena. However, there are many diseases which may be caused by overproduction thereof or overresponse thereto.

IL-6 is a cytokine produced from various cells, e.g. T cells, B cells, macrophages, kidney mesangial cells, fibroblasts, and its various physiological effects are known e.g. induction of B cells differentiation to antibody-producing cells, activation of T cells, increase of platelets, and production of acute phase protein from liver cells. But an abnormal production of IL-6 has been observed in various inflammations, autoimmune diseases and neoplastic diseases and it is suggested that IL-6 plays a certain role in the causes of such pathophysiological situations. In the experiment using an animal model in which IL-6 was forcibly expressed, various types of diseases could be observed and such results strongly suggest the existence of relationship between the abnormal production of IL-6 and the cause of certain diseases (Biochem. J., 265, 621 (1990), Immunol. Today, 11, 443 (1990), J. Autoimmun., 5 Suppl A, 123 (1992), Clin. Immunol. Immunopathol., 62, S60 (1992)).

Therefore inhibition of IL-6 production is expected to improve various kinds of diseases such as inflammatory diseases as a representative. The present invention is targeted for the cytokine and provides novel medicines through inhibiting the production thereof.

Clinical application of the compounds of the present invention involves those diseases which may be caused and be changed to worse by abnormal production of IL-6 or by overresponse to them. Inhibitors of IL-6 production may be used for the prevention and/or treatment of various inflammatory diseases, sepsis, multiple myeloma, plasma cell leukemia, osteoporosis, cachexia, psoriasis, nephritis, renal cell carcinoma, Kaposi's sarcoma, rheumatoid arthritis, hypergammaglobulinemia, Castleman's disease, atrial myxoma, diabetes mellitus, autoimmne diseases, hepatitis, colitis, graft versus host disease, infectious diseases and endometriosis (J. Immunol., 145, 4185 (1990), J. Exp. Med., 172, 1505 (1990), J. Clin. Invest., 87, 739 (1991), J. Clin. Invest., 89, 1681 (1992), EMBO J., 13, 1189 (1994), Hematol. Oncol. Clin. North Am., 11, 159 (1997), Cytokines Cell Mol. Ther., 4(3), 161 (1998), Folia Med. (Plovdiv), 41(1), 78 (1999), JPEN J. Parenter Enteral Nutr., 23(5), S20 (1999), J. Infect. Dis., 180(1), 10 (1999), Am. J. Obstet. Gynecol., 176(3), 593 (1997)).

For example, in the specification of Japanese Patent Application Kokai S59-46244, it is described that hydroxamic acid derivatives of the formula (X)

[wherein $A^X$ is $R^X X^X m^X$ ($R^X$ is phenyl, pyrrolyl, thienyl, imidazolyl or thiazolyl, $X^X$ is halogen, lower alkyl, lower alkoxy or nitro, $m^X$ is 0 or an integer of 1–2 and each $X^X$ is the same or different optionally.), $B^X$ is —CHOH—, —CH—, —O— or —CO, nX is an integer of 2–10.]
is useful as anti-parasite agent.

And in the U.S. Pat. No. 4,769,461, it is described that hydroxamic acid derivatives of the formula (Y)

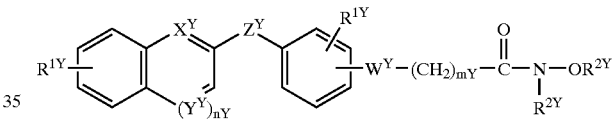

[wherein $W^Y$ is a bond, —O—, —S—, —$NR^{2Y}$—, —CH(OH)— or —$NR^{2Y}$—CO—, $X^Y$ is N or $CR^{2Y}$,
when nY=0, $Y^Y$ is O, S, $NR^{2Y}$ or $C(R^{2Y})_2$
when nY=1, $Y^Y$ is N or $CR^{2Y}$,
$Z^Y$ is —$CH_2O$—, —$CH_2S$—, —$CH_2NR^{2y}$—, —O—, —S—, —$NR^2$—, —CO—, —$CONR^{2Y}$—, —$CHR^{2Y}CHR^{2Y}$—, —$C(R^{2Y})$=$C(R^{2Y})$— or —C≡C—,
$R^{1Y}$ is hydrogen, lower alkyl, trifluoromethyl, nitro, hydroxy, lower alkoxy, mercapto, lower alkylthio or halogen,
$R^{2Y}$ is hydrogen or lower alkyl,
nY is 0 or 1,
mY is 1–6.
With the proviso that when $W^Y$ is a bond, then mY is 0–5.]
is useful as antiinflammatory or anti-allergy agent by inhibition of cyclooxygenase and lipoxygenase.

DISCLOSURE OF THE INVENTION

Energetic investigations have been carried out to discover a compound possessing an inhibitory activity of IL-6 production. As a results, the present inventors have found that the purpose has been achieved by hydroxamic acid derivatives of the formula (I) or non-toxic salts thereof.

Hydroxamic acid derivatives of the formula (I) of the present invention have not been known as inhibitors of IL-6 production at all. Further, almost hydroxamic acid derivatives of the formula (I), non-toxic salts thereof and prodrugs thereof are novel compounds which are not known at all.

The present invention relates to
1) an inhibitor of IL-6 production comprising hydroxamic acid derivatives of the formula (I),

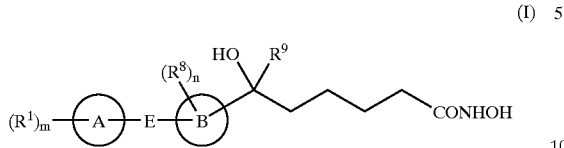

[wherein, $R^1$ is
(a) C1–8 alkyl,
(b) C2–8 alkenyl,
(c) C2–8 alkynyl,
(d) halogen,
(e) nitro,
(f) nitrile,
(g) trifluoromethyl,
(h) trifluoromethoxy,
(i) —$OR^2$,
(j) —$SR^2$,
(k) —$NR^3R^4$,
(l) —$COR^5$,
(m) keto,
(n) Cyc1,
(o) C1–8 alkyl substituted by —$OR^2$, —$SR^2$, —$NR^3R^4$, —$COR^5$ or Cyc1,
(p) —$SO_2R^{10}$,
(q) (C1–8 alkylene)—$OR^{11}$,
(r) C1–8 alkyl substituted by nitrile, —$SO_2R^{10}$ or —O—(C1–8 alkylene)—$OR^{11}$,
(s) —O—(C1–8 alkylene)—$NR^{12}R^{13}$,
(t) —S—(C1–8 alkylene)—$NR^{12}R^{13}$,
(u) C1–8 alkyl substituted by —O—(C1–8 alkylene)—$NR^{12}R^{13}$— or —S—(C1–8 alkylene)—$NR^{12}R^{13}$,
(v) C2–8 alkenyl substituted by —$OR^2$, —$SR^2$, —$NR^3R^4$, —$COR^5$, Cyc1, nitrile, —$SO_2R^{10}$, —O—(C1–8 alkylene)—$OR^{11}$, —O—(C1–8 alkylene)—$NR^{12}R^{13}$ or —S—(C1–8 alkylene)—$NR^{12}R^{13}$ or
(w) C2–8 alkynyl substituted by —$OR^2$, —$SR^2$, —$NR^3R^4$, —$COR^5$, Cyc1, nitrile, —$SO_2R^{10}$, —O—(C1–8 alkylene)—$OR^{11}$, —O—(C1–8 alkylene)—$NR^{12}R^{13}$ or —S—(C1–8 alkylene)—$NR^{12}R^{13}$,
$R^2$ is hydrogen, C1–8 alkyl, C2–9 acyl or Cyc1,
$R^3$ and $R^4$ are each independently hydrogen, C1–8 alkyl, C2–9 acyl or Cyc1,
$R^5$ is hydroxy, C1–8 alkyl, C1–8 alkoxy, —$NR^6R^7$ or Cyc1,
$R^6$ and $R^7$ are each independently hydrogen, C1–8 alkyl or Cyc1,
$R^{10}$ is C1–8 alkyl or Cyc1,
Cyc1 is C3–7 monocarbocyclic ring or 5–7 membered mono-cyclic hetero ring containing 1–4 nitrogen atom(s), one oxygen atom and/or one sulfur atom,
$R^{11}$ is hydrogen, C1–8 alkyl, C2–9 acyl or Cyc1,
$R^{12}$ and $R^{13}$ are each independently hydrogen, C1–8 alkyl, C2–9 acyl or Cyc1,
m is 0 or an integer of 1–5,
ring A is C3–15 mono-, bi- or tri-carbocyclic ring or 5–18 membered mono-, bi- or tri-cyclic hetero ring containing 1–4 nitrogen atom(s), 1–2 oxygen atom(s) and/or 1–2 sulfur atom(s),
ring B is C5–15 mono-, bi- or tri-carbocyclic aryl or 5–18 membered mono-, bi- or tricyclic hetero aryl containing 1–4 nitrogen atom(s), 1–2 oxygen atom(s) and/or 1–2 sulfur atom(s),
E is a bond, —CH=CH— or —C≡C—,
$R^8$ is
(a) C1–8 alkyl,
(b) C1–8 alkoxy,
(c) halogen,
(d) nitro,
(e) nitrile,
(f) trifluoromethyl or
(g) trifluoromethoxy.
With the proviso that when E is a bond, then $R^1$ and $R^8$, taken together, may be optionally C1–4 alkylene.
n is 0 or an integer of 1–5,
$R^9$ is hydrogen, C1–8 alkyl, C2–8 alkenyl or C2–8 alkynyl.],
nontoxic salts thereof or prodrugs thereof, as an active ingredient,
2) Hydroxamic acid derivatives of the formula (I)

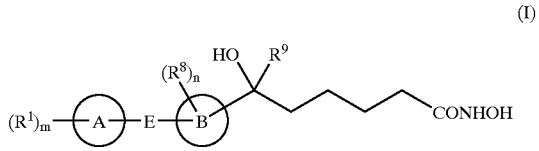

[wherein, $R^1$ is
(a) C1–8 alkyl,
(b) C2–8 alkenyl,
(c) C2–8 alkynyl,
(d) halogen,
(e) nitro,
(f) nitrile,
(g) trifluoromethyl,
(h) trifluoromethoxy,
(i) —$OR^2$,
(j) —$SR^2$,
(k) —$NR^3R^4$,
(l) —$COR^5$,
(m) keto,
(n) Cyc1,
(o) C1–8 alkyl substituted by —$OR^2$, —$SR^2$, —$NR^3R^4$, —$COR^5$ or Cyc1,
(p) —$SO_2R^{10}$,
(q) —O—(C1–8 alkylene)—$OR^{11}$,
(r) C1–8 alkyl substituted by nitrile, —$SO_2R^{10}$ or —O—(C1–8 alkylene)—$OR^{11}$,
(s) —O—(C1–8 alkylene)—$NR^{12}R^{13}$,
(t) —S—(C1–8 alkylene)—$NR^{12}R^{13}$,
(u) C1–8 alkyl substituted by —O—(C1–8 alkylene)—$NR^{12}R^{13}$— or —S—(C1–8 alkylene)—$NR^{12}R^{13}$,
(v) C2–8 alkenyl substituted by —$OR^2$, —$SR^2$, —$NR^3R^4$, —$COR^5$, Cyc1, nitrile, —$SO_2R^{10}$, —O—(C1–8 alkylene)—$OR^{11}$, —O—(C1–8 alkylene)—$NR^{12}R^{13}$ or —S—(C1–8 alkylene)—$NR^{12}R^{13}$ or
(w) C2–8 alkynyl substituted by —$OR^2$, —$SR^2$, —$NR^3R^4$, —$COR^5$, Cyc1, nitrile, —$SO_2R^{10}$, —O—(C1–8 alkylene)—$OR^{11}$, —O—(C1–8 alkylene)—$NR^{12}R^{13}$ or —S—(C1–8 alkylene)—$NR^{12}R^{13}$ or
$R^2$ is hydrogen, C1–8 alkyl, C2–9 acyl or Cyc1,
$R^3$ and $R^4$ are each independently hydrogen, C1–8 alkyl, C2–9 acyl or Cyc1,
$R^5$ is hydroxyl, C1–8 alkyl, C1–8 alkoxy, —$NR^6R^7$ or Cyc1, $R^6$ and $R^7$ are each independently hydrogen, C1–8 alkyl or Cyc1, $R^{10}$ is C1–8 alkyl or Cyc1, Cyc1 is C3–7 mono-carbocyclic ring or 5–7 membered mono-cyclic hetero ring containing 1–4 nitrogen atom(s), one oxygen atom and/or one sulfur atom, $R^{11}$ is hydrogen, C1–8 alkyl, C2–9 acyl or Cyc1, $R^{12}$ and $R^{13}$ are each independently hydrogen, C1–8 alkyl, C2–9 acyl or Cyc1, m is 0 or an integer of 1–5, ring A is C3–15 mono-, bi- or tri-carbocyclic ring or 5–18 membered mono-, bi- or tri-cyclic hetero ring containing 1–4 nitrogen atom(s), 1–2 oxygen atom(s) and/or 1–2 sulfur atom(s), ring B is C5–15 mono-, bi- or tri-carbocyclic aryl or 5–18 membered mono-, bi- or tri-cyclic hetero aryl containing 1–4 nitrogen atom(s), 1–2 oxygen atom(s) and/or 1–2 sulfur atom(s), E is a bond, —CH═CH— or —C≡C—, $R^8$ is
  (a) C1–8 alkyl,
  (b) C1–8 alkoxy,
  (c) halogen,
  (d) nitro,
  (e) nitrile,
  (f) trifluoromethyl or
  (g) trifluoromethoxy.

With the proviso that when E is a bond then $R^1$ and $R^8$, taken together, is C1–4 alkylene optionally.

n is 0 or an integer of 1–5, $R^9$ is hydrogen, C1–8 alkyl, C2–8 alkenyl or C2–8 alkynyl.

With the proviso that when E is —CH═CH— or —C≡C—, ring A is C3–7 mono-carbocyclic ring or 5–7 membered mono-cyclic hetero ring containing 1–4 nitrogen atom(s), one oxygen atom and/or one sulfur atom.], nontoxic salts thereof or prodrugs thereof, 3) the methods for preparation of hydroxamic acid derivatives of the above formula (I), non-toxic salts thereof and prodrugs thereof.

DETAILED EXPLANATION OF THE INVENTION

Unless otherwise specified, all isomers are included in the present invention. For example, alkyl, alkoxy and alkylene groups include straight or branched ones. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomer (D-, L-, d-, l-, (+)-, (−)-isomer), polar compounds generated by chromatographic separation (more polar compound, less polar compound), equilibrium compounds, mixtures thereof at voluntary ratios and racemic mixtures are also included in the present invention.

In the present invention, C1–8 alkyl means methyl, ethyl, propyl, butyl, pentyl, hexyl, heptyl, octyl and the isomers thereof.

C2–8 alkenyl means vinyl, propenyl, butenyl, pentenyl, hexenyl, heptenyl, octenyl, butadienyl, pentadienyl, hexadienyl, heptadienyl, octadienyl, hexatrienyl, heptatrienyl, octatrienyl and the isomer thereof.

C2–8 alkynyl means ethynyl, propynyl, butynyl, pentynyl, hexynyl, heptynyl, octynyl, butadiynyl, pentadiynyl, hexadiynyl, heptadiynyl, octadiynyl, hexatriynyl, heptatriynyl, octatriynyl and the isomer thereof.

Halogen means fluoride, chloride, bromide and iodide.

C1–4 alkylene means methylene, ethylene, trimethylene, tetramethylene and the isomers thereof.

C1–8 alkylene means methylene, ethylene, trimethylene, tetramethylene, pentamethylene, hexamethylene, heptamethylene, octamethylene and isomers thereof.

C2–9 acyl means acetyl, propionyl, butyryl, valeryl, hexanoyl, heptanoyl, octanoyl, nonanoyl and the isomers thereof.

C1–8 alkoxy means methoxy, ethoxy, propoxy, butoxy, pentyloxy, hexyloxy, heptyloxy, octyloxy and the isomers thereof.

C3–7 mono-carbocyclic ring means C3–7 mono-aromatic carbocyclic ring, partially saturated carbocyclic ring thereof and fully saturated carbocyclic ring thereof. It includes, for example, cyclopropane, cyclobutane, cyclopentane, cyclohexane, cycloheptane, cyclopentene, cyclohexene, cycloheptene, cyclopentadiene, cyclohexadiene, cycloheptadiene and benzene etc.

5–7 membered mono-cyclic hetero ring containing 1–4 nitrogen atom(s), one oxygen atom and/or one sulfur atom means 5–7 membered mono-cyclic hetero aryl containing 1–4 nitrogen atom(s), one oxygen atom and/or one sulfur atom and partially or fully saturated one. It includes, for example, pyrrole, imidazole, pyrazole, triazole, tetrazole, pyridine, pyrazine, pyrimidine, pyridazine, azepine, diazepine, furan, pyran, oxepine, oxazepine, thiophene, thiain (thiopyran), thiepine, oxazole, isoxazole, thiazole, isothiazole, oxadiazole, oxazine, oxadiazine, oxazepine, oxadiazepine, thiadiazole, thiazine, thiadiazine, thiazepine, thiadiazepine, pyrroline, pyrrolidine, imidazoline, imidazolidine, pyrazoline, pyrazolidine, triazoline, triazolidine, tetrazoline, tetrazolidine, dihydropyridine, dihydropyrimidine, dihydropyridazine, piperidine, piperazine, tetrahydropyrimidine, tetrahydropyridazine, dihydroazepine, dihydrodiazepine, tetrahydroazepine, tetrahydrodiazepine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, tetrahydroxadiazole, tetrahydroxazine, tetrahydroxadiazine, tetrahydroxazepine, tetrahydroxadiazepine, tetrahydrothiadiazole, tetrahydrothiazine, tetrahydrothiadiazine, tetrahydrothiazepine, tetrahydrothiadiazepine, morpholine and thiomorpholine etc.

C3–15 mono-, bi- or tri-carbocyclic ring means C3–15 mono-, bi- and tri-aromatic carbocyclic ring, partially saturated carbocyclic ring thereof and fully saturated carbocyclic ring thereof. It includes, for example, cyclopropane, cyclobutane, cyclopentane, cyclohexane, cycloheptane, cyclopentene, cyclohexene, cycloheptene, cyclopentadiene, cyclohexadiene, cycloheptadiene, benzene, pentalene, indene, naphthalene, azulene, fluorene, phenanthrene, anthracene, acenaphthylene, biphenylene, perhydropentalene, perhydroindene, dihydronaphthalene, tetrahydronaphthalene, perhydronaphthalene, perhydroazulene, perhydrofluorene, perhydrophenanthrene, perhydroanthracene, perhydroacenaphthylene and perhydrobiphenylene, etc.

5–18 membered mono-, bi- or tri-cyclic hetero ring containing 1–4 nitrogen atom(s), 1–2 oxygen atom(s) and/or 1–2 sulfur atom(s) means 5–18 membered mono-, bi- or tri-cyclic hetero aryl containing 1–4 nitrogen atom(s), 1–2 oxygen atom(s) and/or 1–2 sulfur atom(s) and partially or fully saturated one. It includes, for example, pyrrole, imidazole, pyrazole, triazole, tetrazole, pyridine, pyrazine, pyrimidine, pyridazine, azepine, diazepine, furan, pyran, oxepine, oxazepine, thiophene, thiain (thiopyran), thiepine, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzimidazole, carbazole, acridine, dibenzofuran, dibenzothiophene, pyrroline, pyrrolidine, imidazoline, imidazolidine, pyrazoline, pyrazolidine, triazoline, triazolidine, tetrazoline, tetrazolidine, dihydropyridine, dihydropyrimidine, dihydropyridazine, piperidine, piperazine, tetrahydropyrimidine, tetrahydropyridazine, dihydroazepine, dihydrodiazepine, tetrahydroazepine, tetrahydrodiazepine, dihydrofuran, tetrahydrofuran, dihydropyran, tetrahydropyran, dihydrothiophene, tetrahydrothiophene, dihydrothiain (dihydrothiopyran), tetrahydrothiain (tetrahydrothiopyran), dihydrooxazole, tetrahydrooxazole, dihydroisoxazole, tetrahydroisoxazole, dihydrothiazole, tetrahydrothiazole, dihydroisothiazole, tetrahydroisothiazole, tetrahydrooxadiazole, tetrahydrooxazine, tetrahydrooxadiazine, tetrahydrooxazepine, tetrahydrooxadiazepine, tetrahydrothiadiazole, tetrahydrothiazine, tetrahydrothiadiazine, tetrahydrothiazepine, tetrahydrothiadiazepine, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, benzoxazepine, benzoxadiazepine, benzothiazepine, benzothiadiazepine, benzazepine, benzodiazepine, indroxoazepine, indrotetrahydroxazepine, indroxadiazepine, indrotetrahydroxadiazepine, indrothiazepine, indrotetrahydrothiazepine, indrothiadiazepine, indrotetrahydrothiadiazepine, indroazepine, indrotetrahydroazepine, indrodiazepine, indrotetrahydrodiazepine, benzofurazan, benzothiadiazole, benzotriazole, imidazothiazole, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, 1,3-dioxaindan and 1,4-dioxotetrahydronaphthalene.

C5–15 mono-, bi- or tri-carbocyclic aryl means cyclopentadiene, cyclohexadiene, cycloheptadiene, cycloheptatriene, benzene, indene, naphthalene, fluorene and anthracene etc.

5–18 membered mono-, bi- or tri-cyclic hetero aryl containing 1–4 nitrogen atom(s), 1–2 oxygen atom(s) and/or 1–2 sulfur atom(s) means pyrrole, imidazole, triazole, tetrazole, pyrazole, pyridine, pyrazine, pyrimidine, pyridazine, azepine, diazepine, furan, pyran, oxepine, thiophene, thiain (thiopyran), thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzimidazole, benzoxepine, benzoxazepine, benzoxadiazepine, benzothiepine, benzothiazepine, benzothiadiazepine, benzazepine, benzodiazepine, benzofurazan, benzothiadiazole, benzotriazole, carbazole, acridine, dibenzofuran and dibenzothiophene.

In the present invention, unless otherwise specified, as will be apparent to those skilled in the art, a symbol ⋯ represents bonding to back of the paper (that is, α-configuration), ⬤ represents bonding to front of the paper (that is, β-configuration), ⁓ represents α-, β- or mixture thereof and ∕ represents mixture of α-configuration and β-configuration.

[Salts]

Non-toxic salts of the present invention include all non-toxic salts, for example, general salts, acid addition salts, hydrate salts.

The compounds of the present invention may be converted into the corresponding salts by conventional means. Water-soluble salts are preferred. Suitable salts, for example, include:

salts of alkali metals (e.g. potassium, sodium), salts of alkaline earth metals (e.g. calcium, magnesium), ammonium salts, salts of pharmaceutically acceptable organic amines (e.g. tetramethylammonium, triethylamine, methylamine, dimethylamine, cyclopentylamine, benzylamine, phenethylamine, piperidine, monoethanolamine, diethanolamine, tris (hydroxymethyl)amine, lysine, arginine, N-methyl-D-glucamine).

The compounds of the present invention may be converted into the corresponding acid addition salts by conventional means. Water-soluble salts are preferred. Suitable salts, for example, include:

salts of inorganic acids e.g. hydrochloride, hydrobromide, sulfate, phosphate, nitrate; salts of organic acids e.g. acetate, trifluoroacetate, lactate, tartrate, oxalate, fumarate, maleate, citrate, benzoate, methanesulfonate, ethanesulfonate, benzenesulfonate, toluenesulfonate, isethionate, glucuronate, gluconate.

The compounds of the present invention and salts thereof may be converted into the corresponding hydrates by conventional means.

Furthermore, the prodrugs of the present invention means the compounds that —CONHOH group of the formula (I) is converted to

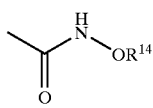

(wherein, $R^{14}$ is C1–8 alkyl substituted by C1–8 alkyl or C1–8 alkoxy) or

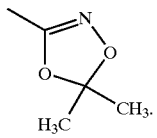

Among the compounds of the present invention, preferred ring A is C3–10 mono-, bi-carbocyclic ring or 5–10 membered mono-, bi-cyclic hetero ring containing 1–4 nitrogen atom(s), 1–2 oxygen atom(s) and/or 1–2 sulfur atom(s). Especially, C5–7 mono-carbocyclic ring or 5–10 membered mono-, bi-cyclic hetero ring containing 1–4 nitrogen atom (s), 1–2 oxygen atom(s) and/or 1–2 sulfur atom(s) is preferable. Benzene, cyclohexane, benzoxazole, benzothiazole, benzimidazole, benzothiophene or benzofuran is more preferable.

Preferred $R^1$ is (1) C1–8 alkyl, (2) —$OR^2$, (3) —$SR^2$, (4) halogen, (5) Cyc1, (6) —$NR^3R^4$ or (7) C1–8 alkyl substituted by —$OR^2$, —$SR^2$, halogen, Cyc1, —$NR^3R^4$. Especially, (1) C1–8 alkyl, (2) C1–8 alkoxy, (3) C1–8 alkylthio, (4) halogen, (5) 5–7 membered mono-cyclic hetero ring containing 1–4 nitrogen atom(s), one oxygen atom and/or one sulfur atom, (6) di(C1–8 alkyl)amino or (7) C1–8 alkyl substituted by C1–8 alkoxy, C1–8 alkylthio, halogen, 5–7 membered mono-cyclic hetero ring, di(C1–8 alkyl) amino is preferable. Methyl, methoxy, methylthio, chloride, dimethylamino, dipropylamino, morpholine, piperidine, piperazine, methoxymethyl, methylthiomethyl, dimethylaminomethyl, dipropylaminomethyl, morpholine-1-ylmethyl, piperidine-1-ylmethyl or piperazine-1-ylmethyl is more preferable.

Preferred stereoisomer of hydroxy group is R configuration, S configuration or mixture thereof. Especially, R or S configuration is preferable. S configuration is more preferable.

Preferred E is, preferably, a bond, —CH=CH— or —C≡C— and a bond or —C≡C— is preferable.

Preferred B ring is C1–5 mono- or bi-carbocyclic aryl or 5–15 membered mono- or bi-cyclic hetero aryl. Especially, benzene, naphthalene, pyridine, thiophene, benzofuran or benzoxazole is preferable.

Preferred $R^8$ is C1–4 alkyl. Especially, methyl is preferable.

Preferred $R^9$ is hydrogen, C1–4 alkyl, C2–4 alkenyl or C2–4 alkynyl. Especially, hydrogen, methyl or allyl is preferable.

Preferred m is 0 or an integer of 1–5. Especially, 0 or 1 is preferable.

Preferred n is 0 or an integer of 1–5. Especially, 0 or 1 is preferable.

In the present invention, preferred compounds are compounds prepared in example hereinafter, shown in the following table 1 to 7 and salts thereof etc.

TABLE 1

(I-1)

| No. | $(R^1)_m$—A— |
|---|---|
| 1 | F—⌬— |
| 2 | $CF_3$—⌬— |
| 3 | $H_3C$\N—⌬—  $H_3C$/ |
| 4 | $CH_3O$—⌬— |
| 5 | HO—⌬— |
| 6 | NC—⌬— |
| 7 | $H_3COOC$—⌬— |
| 8 | morpholino—⌬— |
| 9 | piperidino—⌬— |
| 10 | HN-piperazino—⌬— |
| 11 | Cl,Cl-⌬— |
| 12 | $CH_3O$,$CH_3O$-⌬— |

TABLE 1-continued
(I-1)
| No. | (R¹)ₘ–A– |
|---|---|
| 13 | 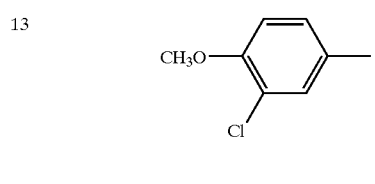 |
| 14 | 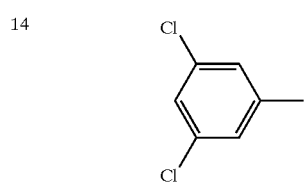 |
| 15 | 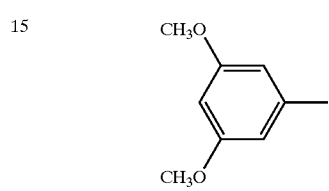 |
| 16 | 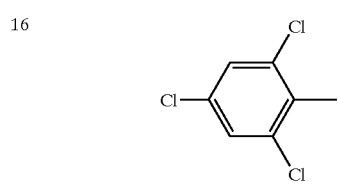 |
| 17 | 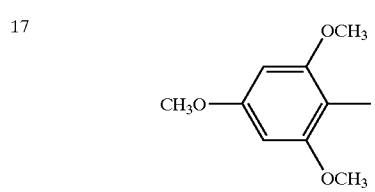 |
| 18 | 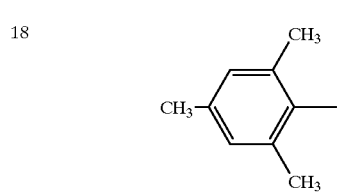 |
TABLE 2
(I-1)
| No. | (R¹)ₘ–A– |
|---|---|
| 1 | cyclopropyl– |
| 2 | cyclopentyl– |
| 3 | cycloheptyl– |
| 4 | piperidin-1-yl– |
| 5 | piperazin-1-yl (HN)– |
| 6 | 4-methylpiperazin-1-yl– |
| 7 | morpholin-4-yl– |
| 8 | tetrahydropyran-4-yl– |
| 9 | 4-oxocyclohexyl– |
| 10 | 4-hydroxycyclohexyl– |
| 11 | 4-aminocyclohexyl– |
| 12 | 4-(dimethylamino)cyclohexyl– |
| 13 | 4-methoxycyclohexyl– |

TABLE 2-continued
(I-1)
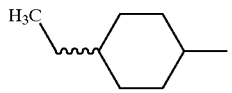
| No. | (R¹)ₘ—A— |
|---|---|
| 14 | 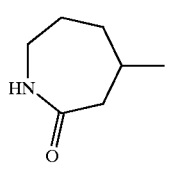 |
| 15 | 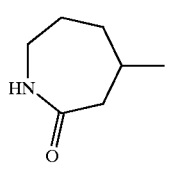 |
| 16 | 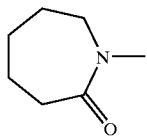 |
| 17 | 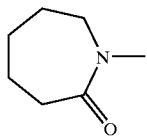 |
| 18 | 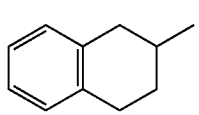 |
| 19 | 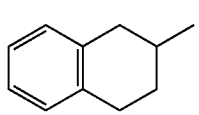 |
| 20 | 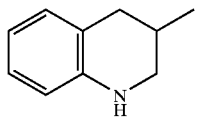 |
TABLE 3
(I-1)
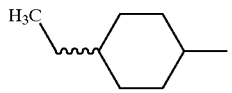
| No. | (R¹)ₘ—A— |
|---|---|
| 1 | 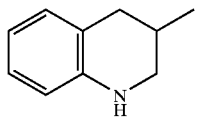 |
| 2 | 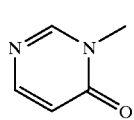 |
| 3 | 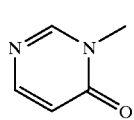 |
| 4 | 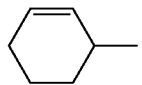 |
| 5 | 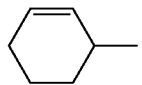 |
| 6 | 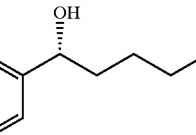 |
| 7 | 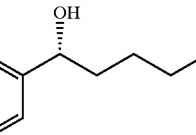 |
| 8 | 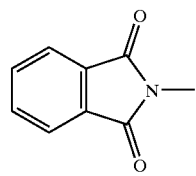 |
| 9 | 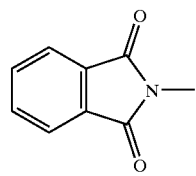 |

TABLE 3-continued (I-1)

| No. | (R¹)ₘ—(A)— |
|---|---|
| 10 | 2-methyl-2,3-dihydrobenzofuran |
| 11 | 2-methyl-1,3-benzodioxole |
| 12 | 2-methyl-1H-indene |

TABLE 4

(I-2)

| No. | (R¹)ₘ—(A)— | (R⁸)ₙ—(B)— |
|---|---|---|
| 1 | phenyl | 3-fluoro-phenyl |
| 2 | cyclohexyl | 3-chloro-phenyl |
| 3 | phenyl | 2-methyl-benzoxazol-5-yl |
| 4 | phenyl | 2-methyl-benzothiazol-5-yl |

TABLE 4-continued (I-2)

| No. | (R¹)ₘ—(A)— | (R⁸)ₙ—(B)— |
|---|---|---|
| 5 | phenyl | 2-methyl-1H-benzimidazol-5-yl |
| 6 | phenyl | 2-methyl-2,3-dihydrobenzofuran-5-yl |
| 7 | phenyl | 2-methyl-1,3-benzodioxol-5-yl |
| 8 | phenyl | 2-methyl-benzothiophen-5-yl |

TABLE 5

(I-3)

| No. | R¹ |
|---|---|
| 1 | 4-pyrrolidinyl-ethyl |
| 2 | 3-pyrrolidinyl-ethyl |
| 3 | 2-pyrrolidinyl-ethyl |
| 4 | 3-morpholinyl-ethyl |

TABLE 5-continued
(I-3)
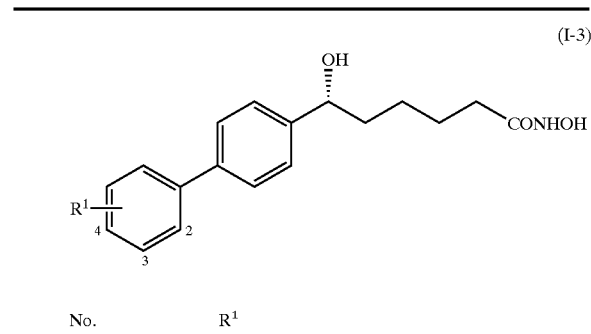
| No. | R¹ |
|---|---|
| 5 | 2- (N-ethylmorpholine) |
| 6 | 3- (N-ethylpiperidine) |
| 7 | 2- (N-ethylpiperidine) |
TABLE 5-continued
(I-3)
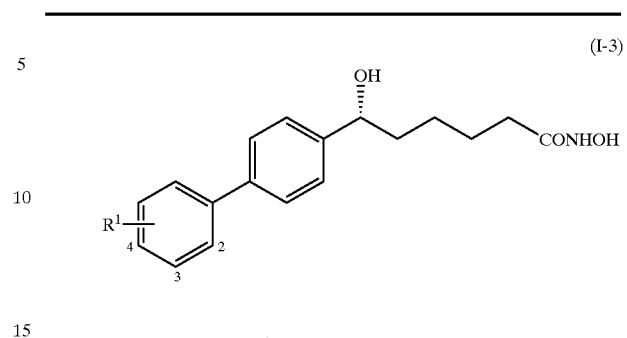
| No. | R¹ |
|---|---|
| 8  | 3-$CH_2$—$N(CH_3)_2$ |
| 9  | 2-$CH_2$—$N(CH_3)_2$ |
| 10 | 4-$(CH_2)_2$—$N(CH_2CH_2CH_3)_2$ |
| 11 | 3-$(CH_2)_2$—$N(CH_2CH_2CH_3)_2$ |
| 12 | 2-$(CH_2)_2$—$N(CH_2CH_2CH_3)_2$ |
| 13 | 3-$CH_2$—$N(CH_2CH_2CH_3)_2$ |
| 14 | 2-$CH_2$—$N(CH_2CH_2CH_3)_2$ |
| 15 | 4-O—$(CH_2)_2$—$N(CH_2CH_2CH_3)_2$ |
| 16 | 4-S—$(CH_2)_2$—$N(CH_2CH_2CH_3)_2$ |
| 17 | 4-O—$(CH_2)_2$—$N(CH_3)_2$ |
| 18 | 4-S—$(CH_2)_2$—$N(CH_3)_2$ |
TABLE 6
(I-4)
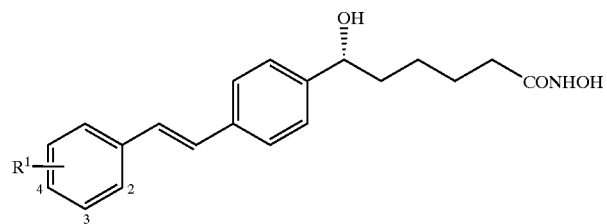
| No. | R¹ |
|---|---|
| 1 | 4- (N-ethylpyrrolidine) |
| 2 | 3- (N-ethylpyrrolidine) |
| 3 | 2- (N-ethylpyrrolidine) |
| 4 | 4- (N-ethylmorpholine) |

TABLE 6-continued
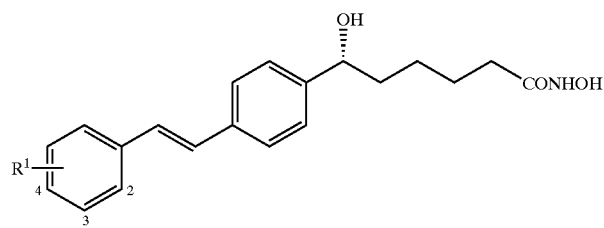
(I-4)
| No. | R¹ |
|---|---|
| 5 | 3- 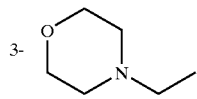 |
| 6 | 2- 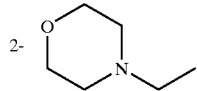 |
| 7 | 4- 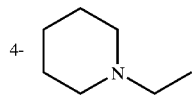 |
| 8 | 3- 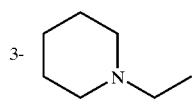 |
| 9 | 2- 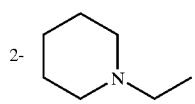 |
| 10 | 4-(CH$_2$)$_2$—N(CH$_3$)$_2$ |
| 11 | 3-(CH$_2$)$_2$—N(CH$_3$)$_2$ |
| 12 | 2-(CH$_2$)$_2$—N(CH$_3$)$_2$ |
| 13 | 4-(CH$_2$)$_2$—N(CH$_2$CH$_2$CH$_3$)$_2$ |
| 14 | 3-(CH$_2$)$_2$—N(CH$_2$CH$_2$CH$_3$)$_2$ |
| 15 | 2-(CH$_2$)$_2$—N(CH$_2$CH$_2$CH$_3$)$_2$ |
| 16 | 4-CH$_2$—N(CH$_2$CH$_2$CH$_3$)$_2$ |
| 17 | 3-CH$_2$—N(CH$_2$CH$_2$CH$_3$)$_2$ |
| 18 | 2-CH$_2$—N(CH$_2$CH$_2$CH$_3$)$_2$ |
| 19 | 4-O—(CH$_2$)$_2$—N(CH$_2$CH$_2$CH$_3$)$_2$ |
| 20 | 4-S—(CH$_2$)$_2$—N(CH$_2$CH$_2$CH$_3$)$_2$ |
| 21 | 4-O—(CH$_2$)$_2$—N(CH$_3$)$_2$ |
| 22 | 4-S—(CH$_2$)$_2$—N(CH$_3$)$_2$ |

TABLE 7
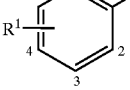
(I-5)
| No. | R¹ |
|---|---|
| 1 | 4- 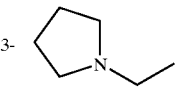 |
| 2 | 3- 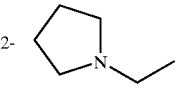 |
| 3 | 2- 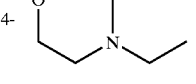 |
| 4 | 4- 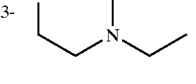 |
| 5 | 3- 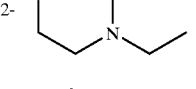 |
| 6 | 2- 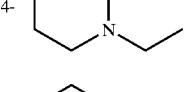 |
| 7 | 4- 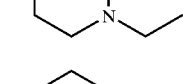 |
| 8 | 3- 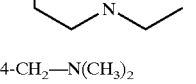 |
| 9 | 2- |
| 10 | 4-CH$_2$—N(CH$_3$)$_2$ |
| 11 | 3-CH$_2$—N(CH$_3$)$_2$ |
| 12 | 2-CH$_2$—N(CH$_3$)$_2$ |
| 13 | 4-(CH$_2$)$_2$—N(CH$_2$CH$_2$CH$_3$)$_2$ |
| 14 | 3-(CH$_2$)$_2$—N(CH$_2$CH$_2$CH$_3$)$_2$ |
| 15 | 2-(CH$_2$)$_2$—N(CH$_2$CH$_2$CH$_3$)$_2$ |
| 16 | 4-CH$_2$—N(CH$_2$CH$_2$CH$_3$)$_2$ |
| 17 | 3-CH$_2$—N(CH$_2$CH$_2$CH$_3$)$_2$ |
| 18 | 2-CH$_2$—N(CH$_2$CH$_2$CH$_3$)$_2$ |
| 19 | 4-O—(CH$_2$)$_2$—N(CH$_2$CH$_2$CH$_3$)$_2$ |

TABLE 7-continued

(I-5)

| No. | $R^1$ |
|---|---|
| 20 | 4-S—$(CH_2)_2$—$N(CH_2CH_2CH_3)_2$ |
| 21 | 4-O—$(CH_2)_2$—$N(CH_3)_2$ |
| 22 | 4-S—$(CH_2)_2$—$N(CH_3)_2$ |

[Methods for Preparation of the Compounds of the Present Invention]

Hydroxamic acid derivatives of the formula (I) in the present invention, non-toxic salts thereof and prodrugs thereof may be prepared by the following methods or the methods described in examples.

[1] Among the compounds of the present invention, the prodrugs of the formula (IA) may be prepared by the following methods of (a)–(c).

(a) Among the prodrugs of the formula (IA), the compounds in which $R^1$ doesn't represent a group containing amino, thiol and carboxy, that is, the compounds of the formula (IA-a)

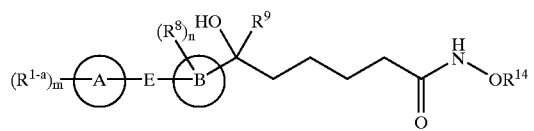

(IA-a)

(wherein, $R^{1-a}$ has the same meaning as $R^1$. With the proviso that $R^{1-a}$ doesn't represent a group containing of amino, thiol and carboxy and the other symbols have the same meaning as defined hereinbefore.) may be prepared by amidation of the compounds of the formula (II)

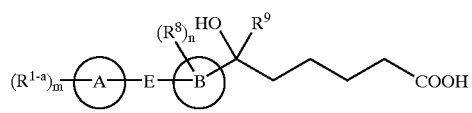

II (wherein, all the symbols have the same meaning as defined hereinbefore.) and the compounds of the formula (III)

$$H_2N—OR^{14}$$ (III)

(wherein, $R^{14}$ has the same meaning as defined hereinbefore.).

The amidation is known. For example, it may be carried out
(1) by the method with using acid halide,
(2) by the method with using mixed acid anhydride,
(3) by the method with using conducing agent etc.

Concrete description of these methods are as follows:

(1) The method with acid halide may be carried out, for example; carboxylic acid is reacted with an acid halide (oxalyl chloride or thionyl chloride etc.) in an organic solvent (chloroform, methylene chloride, diethyl ether or tetrahydrofuran etc.) or without solvents at from −20° C. to a refluxing temperature to give an acid halide. The obtained acid halide and an amine are reacted in an organic solvent (chloroform, methylene chloride, diethyl ether or tetrahydrofuran etc.) in the presence of tertiary amine (pyridine, triethylamine, dimethylaniline or dimethylaminopyridine etc.), at 0–40° C. Also this reaction may be carried out by the reaction with amine and acid halide in an organic solvent (dioxane or tetrahydrofuran etc.), with an aqueous alkali solution (solution of bicarbonate or solution of sodium hydroxide etc.) at 0–40° C.

(2) The method with mixed acid anhydride may be carried out, for example; carboxylic acid is reacted with an acid halide (pivaloyl chloride etc.) or an acid derivative (ethyl chloroformate or isobutyl chloroformate etc.) in an organic solvent (chloroform, methylene chloride, diethyl ether or tetrahydrofuran etc.) or without solvents, in the presence of tertiary amine (pyridine, triethylamine, dimethylaniline or dimethylaminopylidine etc.), at 0–40° C. The mixed acid anhydride is reacted with an amine in an organic solvent (chloroform, methylene chloride, diethyl ether or tetrahydrofuran etc.) at 0–40° C.

(3) The method with condensing agent may be carried out, for example; a carboxylic acid and an amine are reacted in an organic solvent (chloroform, methylene chloride, dimethylformamide, diethyl ether or tetrahydrofuran etc.) or without solvents in the presence or absence of tertiary amine (pyridine, triethylamine, dimethylaniline or dimethylaminopyridine etc.) using with condensing agent (1,3-dicyclohexylcarbodiimido (DCC), 1-ethyl-3-[3-(dimethylamino)propyl]carbodiimido (EDC), 1,1'-carbonyidiimidazole (CDI), 2-chloro-1-methylpyridinium iodide or 1-propanephosphonic acid cyclic anhydride (PPA) etc.) using or without 1-hydroxybenzotriazole (HOBt) at 0–40° C.

Preferably, the above reactions (1), (2) and (3) are carried out under an atmosphere of an inert gas (argon, nitrogen etc.) on anhydrous condition.

(b) Among the prodrugs of the formula (IA), the above compounds of the formula (IA-a) may be prepared by coupling reaction with the compounds of the formula (IV)

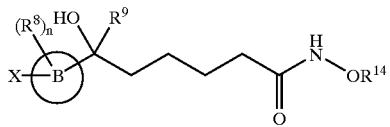

(IV)

(wherein, X is halogen and the other symbols have the same meaning as defined hereinbefore.) and the compounds of the formula (V)

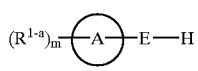

(V)

(wherein all the symbols have the same meaning as defined hereinbefore.) or the compounds of the formula (VI)

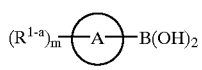

(VI)

(wherein all the symbols have the same meaning as defined hereinbefore.).

The reaction is known. For example, it may be carried out in an organic solvent (benzene, dimethylformamide, dioxane, tetrahydrofuran, methanol, acetonitrile, dimethoxyethane or acetone etc.) in the presence of a base (sodium ethylate, sodium hydroxide, potassium hydroxide, triethylamine, sodium carbonate, sodium hydrogen carbonate, potassium carbonate, cesium carbonate, thallium carbonate, tripotassium phosphate, cesium fluoride, barium hydroxide or tetrabutylammonium fluoride etc.) and a catalyst (tetrakis(triphenylphosphine)palladium ($Pd(PPh_3)_4$), dichlorobis(triphenylphosphine)palladium ($PdCl_2(PPh_3)_2$), palladium acetate ($Pd(OAc)_2$), palladium black, 1,1-bis(diphenylphosphinoferrocene)dichloro palladium ($PdCl_2(dppf)_2$), dichlorodiallylpalladium ($PdCl_2(allyl)_2$) or iodephenylbis(triphenylphosphine)palladium ($PhPdI(PPh_3)_2$) etc.) at room temperature −120° C.

(c) Among the prodrugs of the formula (IA), the compounds in which $R^1$ is a group containing at least one of amino, thiol or carboxy, i.e., the compounds of the formula (IA-c)

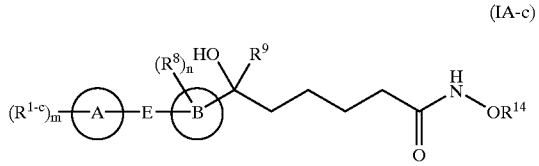

(IA-c)

(wherein, $R^{1-c}$ is a group containing at least one of amino, thiol or carboxy and the other symbols have the same meaning as defined hereinbefore.) may be prepared by the removal of a protecting group in the compounds of the formula (IA-a) in which amino, thiol or carboxy is protected by a protecting group, i.e., the compounds (IA-a1)

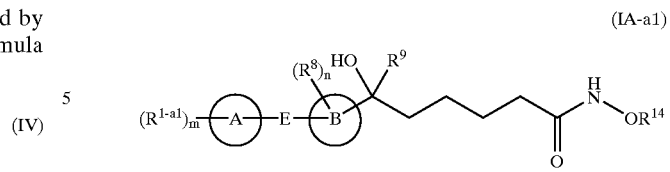

(IA-a1)

(wherein, $R^{1-a1}$ is a group containing at least one of protected amino, protected thiol or protected carboxy and the other symbols have the same meaning as defined hereinbefore.).

A protecting group of amino includes, for example, benzyloxycarbonyl, allyloxycarbonyl, t-butoxycarbonyl, trifluoroacetyl or 9-fluorenylmethoxycarbonyl.

A protecting group of thiol includes, for example, benzyl, methoxybenzyl, acetoamidemethyl, triphenylmethyl or acetyl.

A protecting group of carboxy includes, for example, methyl, ethyl, t-butyl, benzyl or allyl.

The protecting group of amino, thiol or carboxy includes the above one, in addition, the other protecting group which is removable selectively and easily, for example, one described in T. W. Greene et. al., Protective Groups in Organic Synthesis, Third Edition, Wiley-Interscience, New York, 1999.

The removal of a protecting group of amino, thiol or carboxy is well known. For example, it is (1) the removal of a protecting group in an alkaline condition,
(2) the removal of a protecting group in an acidic condition,
(3) the removal of a protecting group by hydrogenelysis, or
(4) the removal of a protecting group using metal complex etc.

Concrete description of these methods are as follows:

(1) The removal of protecting group in an alkaline condition may be carried out, for example, in an organic solvent (methanol, tetrahydrofuran or dioxane etc.) with hydroxide of alkaline metal (sodium hydroxide, potassium hydroxide or lithium hydroxide etc.), hydroxide of alkaline earth metal (barium hydroxide or calcium hydroxide etc.), carbonate (sodium carbonate or potassium carbonate etc.), or an aqueous solution thereof or a mixture thereof at 0–40° C.

(2) The removal of protecting group in an acidic condition may be carried out, for example, in an organic solvent (dichloromethane, chloroform, dioxane, ethyl acetate or anisole etc.), organic acid (acetic acid, trifluoroacetic acid or methanesulfonic acid) or inorganic acid (hydrochloric acid or sulfuric acid etc.), or a mixture thereof (hydrogen bromide/acetic acid etc.) at 0–100° C.

(3) The removal of a protecting group by hydrogenelysis may be carried out, for example, in a solvent (ether (tetrahydrofuran, dioxane, dimethoxyethane or diethylether etc.), alcohol(methanol or ethanol etc.), benzene(benzene or toluene etc.), ketone (acetone or methylethylketone etc.), nitrile (acetonitrile etc.), amido (dimethylformamide etc.), water, ethyl acetate, acetic acid or a mixture thereof etc.) in the presence of a catalyst (palladium-carbon, palladium black, palladium hydroxide, platinum oxide, raney nickel etc.), at atmospheric or reduced pressure under an atmosphere of hydrogen or ammonium formate at 0–200° C.

(4) The removal of a protecting group using metal complex may be carried out, for example, in an organic solvent (dichloromethane, dimethylformamide or tetrahydrofuran etc.) in the presence of a trap reagent (tributyltin hydride or dimedone etc.) and/or an organic acid (acetic acid etc.) with metal complex (tetrakis(triphenylphosphine)palladium(0) complex etc.) at 0–40° C.

As well known to the person in the art, the aimed compounds of present invention may be prepared easily by choice of these reaction.

[2] Among the compounds of the present invention, hydroxamic acid derivatives of the formula (I) may be prepared by the method of (d) or (e).

(d) Among hydroxamic acid derivatives of the formula (I), the compound wherein $R^1$ doesn't represent a group containing amino, thiol or carboxy, i.e., the compound of the formula (I-d)

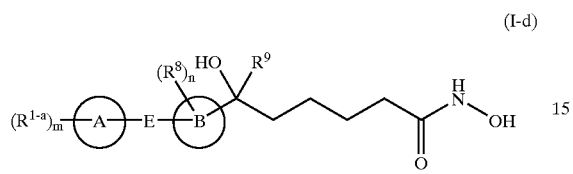

(I-d)

(wherein, all the symbols have the same meaning as defined hereinbefore.) may be prepared by the amidation with the compound of the above formula (II) and hydroxyamine ($H_2N$—OH).

The amidation may be carried out by the same procedure as described hereinbefore.

(e) Hydroxamic acid derivatives of the formula (I) may be prepared by the removal of a protecting group of the compounds of the above formula (IA).

The removal of a protecting group of the hydroxamic acid is known. For example, it is (1) the removal of a protecting group in an alkaline condition,
(2) the removal of a protecting group in an acidic condition, or
(3) the removal of a protecting group by hydrogenelysis etc.

The removal of a protecting group may be carried out by the same procedure as described hereinbefore.

The reaction of the removal of a protecting group of hydroxamic acid in the present invention means an ordinal one which is well known to the person in the art, for example, the removal of a protecting group in an alkaline condition, the removal of a protecting group in an acidic condition or the removal of a protecting group by hydrogenelysis. The aimed compounds of the present invention may be prepared easily by choice of these reaction.

As well known to the person in the art, a protecting group of hydroxamic acid includes, for example, t-butyl, —C(CH$_3$)$_2$—OCH$_3$ and benzyl. In addition, such a group includes the other protecting group which is removable selectively and easily, for example, one described in T. W. Greene et. al., Protective Groups in Organic Synthesis, Third Edition, Wiley-Interscience, New York, 1999.

[3] Among the compounds of the present invention, the prodrugs of the formula (IB) may be prepared by the removal of the methanol in the compounds of the formula (IA) wherein $R^{14}$ is 1-methoxy-1-methylethyl, i.e., the compounds of the formula (IA-3)

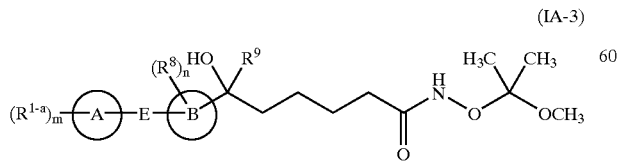

(IA-3)

(wherein, all the symbols have the same meaning as defined hereinbefore.).

The reaction of the removal of methanol is known. For example, it may be carried out in an organic solvent (benzene, toluene, dioxane or pyridine etc.) at 60–150° C.

The compounds of the formula (II) and (IV) are known per se or may be prepared according to the following Reaction Scheme 1 and Reaction Scheme 2 or by known methods easily.

Reaction Scheme 1

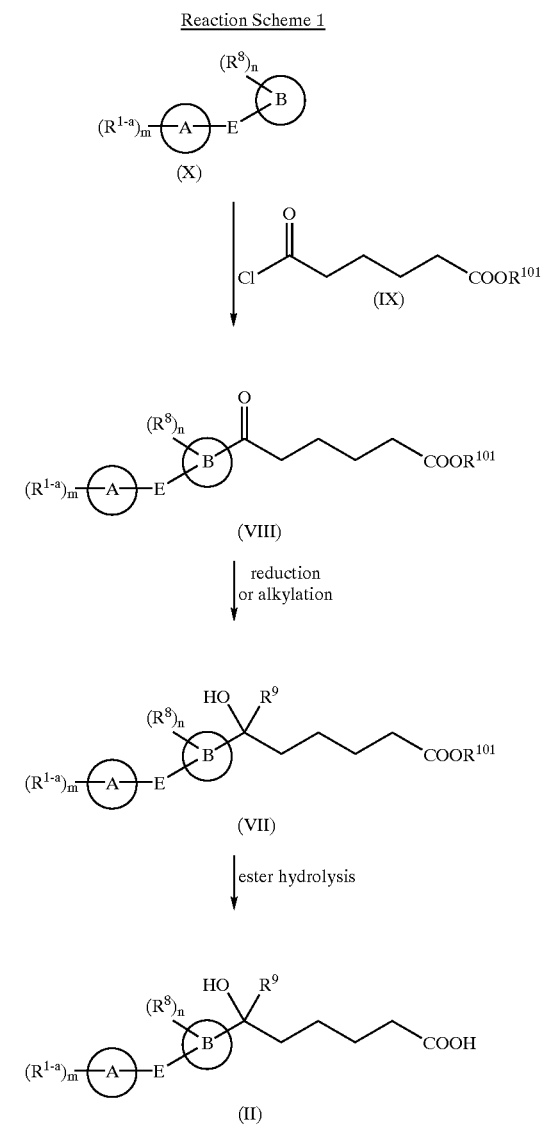

Reaction Scheme 2

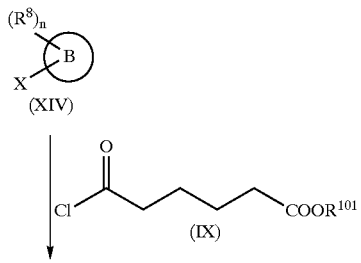

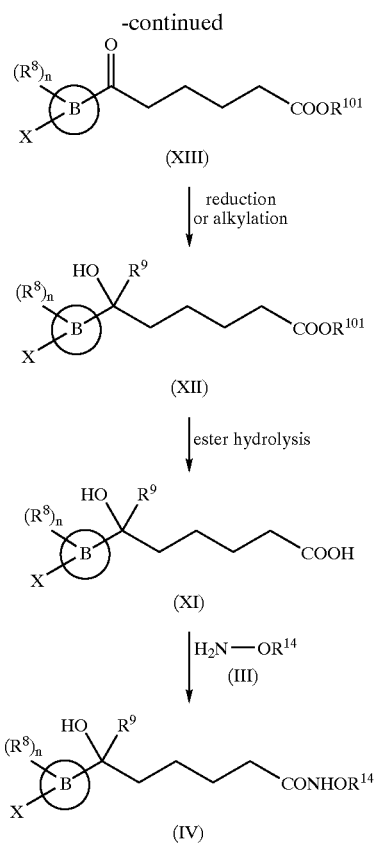

In reaction scheme,

R$^{101}$ is C1–4 alkyl or —CH$_2$CH$_2$OCH$_2$CH$_2$OCH$_3$,

R$^{1-a}$, R$^8$, R$^9$, R$^{14}$, ring A, ring B, E, m, n or X have the same meaning as defined hereinbefore.

In above reaction schemes, each reaction may be carried out by each conventional technique. Further, in above reaction scheme, the compounds of the formula (X), (XIV), (III), (V) and (VI) used as starting materials have been known per se or may be prepared by known methods easily.

In each reaction in the present specification, obtained products may be purified by conventional techniques. For example, purification may be carried out by distillation at atmospheric or reduced pressure, by high performance liquid chromatography, by thin layer chromatography or by column chromatography using silica gel or magnesium silicate, by washing or by recrystallization. Purification may be carried out after each reaction, or after a series of reactions.

The other starting materials and each test compounds in the present invention have been known per se or may be prepared by known methods.

[Pharmacological Activities of the Compounds of the Present Invention]

According to following experiments, it is confirmed that the compound of the present invention has an inhibitory activity on IL-6 production.

(1) The Measurement of an Inhibitory Activity on IL-6 Production from A549 Cells

[Method]

1.5×10$^4$ of A549 cells (human lung epithelial cell line) were suspended in 100 μL of Dulbecco's Modified Eagle Medium (DMEM) containing 0.5% fetal bovine serum (abbreviated as FBS) and incubated for a day and night in 96 well-microplate. 20 μL of the test compound dissolved in dimethylsulfoxide (DMSO) at various concentrations and 80 μL of tumor necrosis factor-α (TNF-α (Genzyme Co., cat. No. TNF-H)) dissolved in serum-free DMEM at the concentration of 12.5 ng/mL were added thereto. After the incubation for 24 hours, the supernatant (100 μL) was collected to measure the amount of IL-6 being produced using enzyme linked immuno solvent assay (ELISA) (R&D Systems Co., cat. No. D6050). Then the inhibitory activity of the test compound was calculated and the 50% inhibitory concentration (IC$_{50}$) was determined. For example, the IC$_{50}$ value of the compound of example 3 was 0.052 μM.

(2) The Measurement of an Inhibitory Activity on IL-6 Production from Human Synovial Cells

[Method]

3.0×10$^3$ of synovial cells from rheumatoid arthritis patients were suspended in 200 μL of DMEM containing 10% FBS and incubated for a day and night in 96 well-microplate, followed by the incubation for 5 hours in serum-free DMEM. 20 μL of the test compound dissolved in DMSO at various concentrations and 80 μL of interleukin-1β (IL-1β (Genzyme Co., cat. No. 80-3688-01)) dissolved in DMEM containing 2.5% fetal bovine serum at the concentration of 5 ng/mL were added thereto. After the incubation for 24 hours, the supernatant (100 μL) was collected to measure the amount of IL-6 being produced using ELISA (R&D Systems Co., cat. No. D6050). Then the inhibitory activity of the test compound was calculated and the 50% inhibitory concentration (IC$_{50}$) was determined. For example, the IC$_{50}$ value of the compound of example 3 was 0.041 μM.

(3) The Effect on Collagen-induced Arthritis Model in Rats

[Method]

Eight weeks old female DA rats were used. During the experimental period, they were housed in animal room artificially kept the room temperature of 24±2° C., humidity of 55±5%, and 12 hours interval of light and dark cycle. They had free access to a standard solid pellet chow (CE-2, Japan CLEA) and drinking tap water, and were used for the experiment after a week acclimation. The collagen-induced arthritis was performed by the following method. After the mixing of bovine type II collagen (0.3% collagen solution, KOKEN #K41, lot. 11214, abbreviated as CII), incomplete Freund's adjuvant (DIFCO #0639-60) and saline with the ratio of 1:2:1, the mixture was then ultra-sonicated to form emulsion for 20 seconds×3 times at 1 minute interval. The intradermal injection of 0.1 mL of the emulsion (0.75 mg of CII/mL) was performed on each four different portions of the back on day 0. A week after the first immunization, arthritis was elicited by the intradermal injection of 0.15 mL of the emulsion at the basal portion of the tail. The test compound was suspended in 0.5% carboxymethylcellulose solution, and was administered orally in the morning and evening twice a day from day 0 to day 28. According to the method of Osterman T. et al. (Inflamm. Res., 44, 258–263, 1995), the severity of arthritis was judged and scored. The hind paw volume of each animal was also measured with the plethysmometer (UNICOM, TK-101CMP). For example, 10 mg/kg/day (b.i.d.) of the compound of the example 3 completely inhibited the development of arthritis, and the example 3 even at the dose of 3 mg/kg/day showed significant inhibition by approximately 60% on the arthritis score and the hind paw edema.

[Toxicity]

The toxicity of the compounds of formula (I) of the present invention, nonoxic salts thereof or prodrugs thereof is very low and therefore the compounds may be considered safe for pharmaceutical use.

[Application for Pharmaceuticals]

The compounds of the present invention possess an inhibitory activity of IL-6 production in animal, especially human, so they are useful for the prevention and/or treatment of, for example, various inflammatory diseases, sepsis, multiple myeloma, plasma cell leukemia, osteoporosis, cachexia, psoriasis, nephritis, renal cell carcinoma, Kaposi's sarcoma, rheumatoid arthritis, hypergammaglobulinemia , Castleman's disease, atrial myxoma, diabetes mellitus, autoimmne diseases, hepatitis, colitis, graft versus host disease, infectious diseases and endometriosis.

For the purpose above described, the compounds of formula (I), non-toxic salts thereof or prodrugs thereof may be normally administered systemically or locally, usually by oral or parenteral administration.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 0.1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compounds of the present invention may be administered in the form of, for example, solid forms for oral administration, liquid forms for oral administration, injections, liniments or suppositories for parenteral administration.

Solid forms for oral administration include compressed tablets, pills, capsules, dispersible powders, and granules. Capsules include hard capsules and soft capsules.

In such solid forms, one or more of the active compound (s) may be admixed with vehicles (such as lactose, mannitol, glucose, microcrystalline cellulose, starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable solutions, suspensions and emulsions, syrups and elixirs. In such forms, one or more of the active compound(s) may be dissolved, suspended or emulized into diluent(s) commonly used in the art (such as purified water, ethanol or a mixture thereof). Furthermore, such liquid forms may also comprise some additives, such as wetting agents, suspending agents, emulsifying agents, sweetening agents, flavoring agents, aroma, preservative or buffering agent.

Injections for parenteral administration include sterile aqueous, suspensions, emulsions and solid forms which are dissolved or suspended into solvent(s) for injection immediately before use. In injections, one or more of the active compound(s) may be dissolved, suspended or emulized into solvent(s). The solvents may include distilled water for injection, physiological salt solution, vegetable oil, propylene glycol, polyethylene glycol, alcohol, e.g. ethanol, or a mixture thereof. Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared and compensated according to sterile methods. They may also be manufactured in the form of sterile solid forms such as freeze-dried products, which may be dissolved in sterile water or some other a sterile diluent(s) for injection immediately before use.

Other forms for parenteral administration include liquids for external use, IL-6 ointments and endermic liniments, inhalations, sprays, suppositories and pessaries for vaginal administration which comprise one or more of the active compound(s) and may be prepared by methods known per se.

Sprays may comprise additional substances other than diluents, such as stabilizing agents (such as sodium sulfate), isotonic buffers (such as sodium chloride, sodium citrate or citric acid). For preparation of such sprays, for example, the method described in the U.S. Pat. No. 2,868,691 or U.S. Pat. No. 3,095,355 may be used.

THE BEST MODE FOR CARRYING OUT THE INVENTION

The following reference examples and examples are intended to illustrate the present invention, but do not limit them.

In chromatographic separations and TLC, the solvents in parenthesis show the eluting and developing solvents and the ratios of the solvents used are by volume.

The solvents in parenthesis in NMR show the solvents used for measurement.

REFERENCE EXAMPLE 1

Ethyl 6-(4-(4-chlorophenyl)phenyl)-6-oxohexanoate

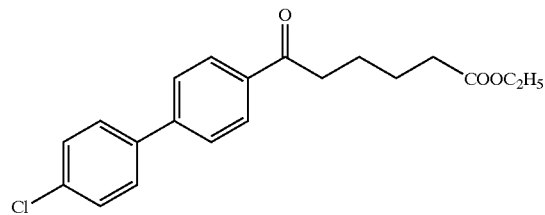

To adipic acid mono ethyl ester (34.8 g) was added thionyl chloride (72 mL). The reaction mixture was stirred at 100° C. for 1.5 hours. The reaction mixture was concentrated to give adipinyl chloride mono ethyl ester. To a suspension of aluminium chloride (53.3 g) in dichloromethane (500 mL) was added 4-chlorobiphenyl (37.7 g) at 5° C. The reaction mixture was stirred for 15 minutes and a solution of adipinyl chloride mono ethyl ester in dichloromethane (200 mL) was added thereto at 5° C. The reaction mixture was stirred at room temperature for 2 hours. To the reaction mixture was added ice water and the mixture was extracted with dichloromethane. The extract was washed with water, a saturated aqueous solution of sodium hydrogen carbonate and a saturated aqueous solution of sodium chloride, dried over anhydrous magnesium sulfate, and concentrated. The obtained residue was recrystallized from hexane/ethyl acetate and dried to give the title compound (53.8 g) having the following physical data.

TLC: Rf 0.60 (chloroform),

NMR (CDCl$_3$): δ 8.04 (d, J=8.8 Hz, 2H), 7.64 (d, J=8.8 Hz, 2H), 7.56 (d, J=8.4 Hz, 2H), 7.44 (d, J=8.4 Hz, 2H), 4.14 (q, J=7.2 Hz, 2H), 3.03 (t, J=6.6 Hz, 2H), 2.38 (t, J=7.0 Hz, 2H), 1.95–1.60 (m, 4H), 1.26 (t, J=7.2 Hz, 3H).

REFERENCE EXAMPLE 2

Ethyl 6-(4-(4-chlorophenyl)phenyl)-6-hydroxyhexanoate

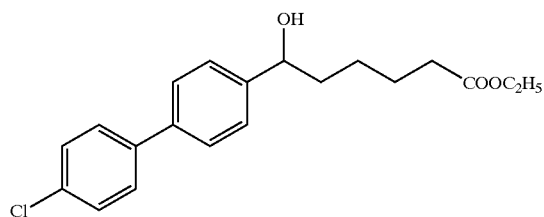

To a mixture solution of the compound prepared in reference example 1 (10.02 g) in dichloromethane (300 mL) and methanol (100 mL) was added sodium borohydride (5.4 g) at 0° C. The reaction mixture was stirred at room temperature for 2 hours. The reaction mixture was poured Into a saturated aqueous solution of ammonium chloride and extracted with dichloromethane. The extract was washed with a saturated aqueous solution of sodium chloride, dried over anhydrous sodium sulfate, and concentrated to give the title compound (10.03 g) having the following physical data.

TLC: Rf 0.25 (chloroform),

NMR (CDCl$_3$): δ 7.65–7.34 (m, 8H), 4.73 (t, J=6.2 Hz, 1H), 4.11 (q, J=7.0 Hz, 2H), 2.03 (t, J=7.0 Hz, 2H), 1.90–1.30 (m, 6H), 1.23 (t, J=7.0 Hz, 3H).

REFERENCE EXAMPLE 3

6-(4-(4-chlorophenyl)phenyl)-6-hydroxyhexanoic acid

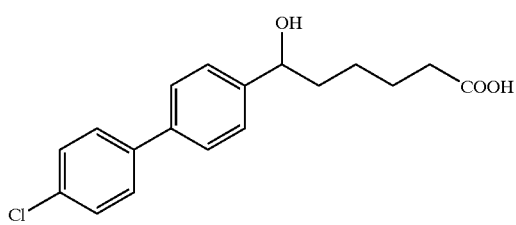

To a solution of the compound prepared in reference example 2 (10.03 g) in ethanol (100 mL) was added 2N aqueous solution of sodium hydroxide (50 mL). The reaction mixture was stirred at 60° C. for 1 hour. To the reaction mixture was added 1N aqueous solution of hydrochloric acid and the mixture was extracted with ethyl acetate. The extract was washed with a saturated aqueous solution of sodium chloride, dried over anhydrous sodium sulfate, and concentrated. The obtained residue was recrystallized from isopropylalcohol and dried to give the title compound (9.12 g) having the following physical data.

TLC: Rf 0.52 (chloroform:tetrahydrofuran:acetic acid=10:4:1),

NMR (d$_6$-DMSO): δ 11.80 (brs, 1H), 7.68 (d, J=8 Hz, 2H), 7.61 (d, J=8 Hz, 2H), 7.49 (d, J=8 Hz, 2H), 7.40 (d, J=8 Hz, 2H), 5.16 (brs, 1H), 4.65–4.40 (m, 1H), 2.18 (t, J=7 Hz, 2H), 1.80–1.05 (m, 6H).

EXAMPLE 1

N-(1-methoxy-1-methyl)ethoxy-(4-(4-chlorophenyl)phenyl)-6-hydroxyhexanamide

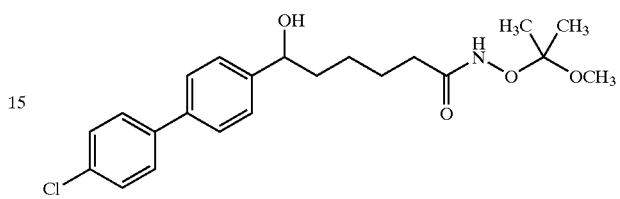

Under an atmosphere of argon, to a solution of the compound prepared in reference example 3 (7.74 g) in dimethylformamide (150 mL) was added 1-ethyl-3-[3-(dimethylamino)propyl]carbodiimide (6.99 g), 1-hydroxybenzotriazol (5.58 g), (1-methoxy-1-methylethyl)hydroxyamine (8.0 g) and triethylamine (15.5 mL). The reaction mixture was stirred at room temperature overnight. The reaction mixture was poured into ice water and extracted with ethyl acetate. The extract was washed with a saturated aqueous solution of sodium hydrogen carbonate and a saturated aqueous solution of sodium chloride, dried over anhydrous sodium sulfate, and concentrated. The obtained residue was purified by column chromatography on silica gel (ethyl acetate:hexane:triethylamine=80:20:1) to give the compound of the present invention (8.1 g) having the following physical data.

TLC: Rf 0.50 (ethyl acetate:methanol=20:1),

NMR (CDCl$_3$): δ 7.73 (brs, 1H), 7.60–7.35 (m, 8H), 4.74 (t, J=6 Hz, 1H), 3.31 (s, 3H), 2.50–1.15 (m, 8H), 1.41 (s, 6H).

EXAMPLE 2

N-hydroxy-6-(4-(4-chlorophenyl)phenyl)-6-hydroxyhexanamide

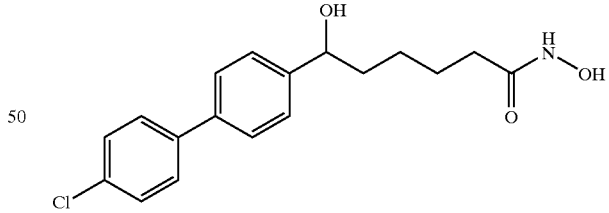

To a solution of the compound prepared in example 1 (7.27 g) in methanol (100 mL) was added concentrated hydrochloric acid (2.0 mL). The reaction mixture was stirred at room temperature for 30 minutes. The reaction mixture was concentrated and distilled off an azetropic mixture with ethanol. To the obtained residue was added ethyl acetate and the precipitated crystal was filtered and dried to give the compound of the present invention (5.55 g) having the following physical data.

TLC: Rf 0.21 (chloroform:methanol:acetic acid=10:1:1),

NMR (d$_6$-DMSO): δ 10.31 (s, 1H), 8.64 (s, 1H), 7.68 (d, J=8.8 Hz, 2H), 7.65 (d, J=8.8 Hz, 2H), 7.50 (d, J=8.4 Hz,

2H), 7.40 (d, J=8.4 Hz, 2H), 5.15 (d, J=4.4 Hz, 1H), 4.54 (m, 1H), 1.93 (t, J=7.3 Hz, 2H), 1.70–1.40 (m, 4H), 1.40–1.10 (m, 2H).

EXAMPLES 2(1)–2(5)

By the same procedure as a series of reactions of reference example 1→reference example 2→reference example 3→example 1→example 2 using a corresponding benzene derivative instead of 4-chlorobiphenyl, the following compounds of the present invention were obtained.

EXAMPLE 2(1)

N-hydroxy-6-(4-biphenyl)-6-hydroxyhexanamide

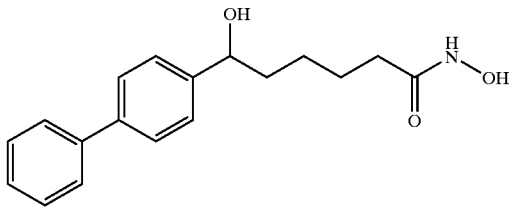

TLC: Rf 0.42 (ethyl acetate:methanol=39:1),

NMR ($d_6$-DMSO): δ 10.29 (brs, 1H), 8.64 (brs, 1H), 7.66–7.58 (m, 4H), 7.47–7.30 (m, 5H), 5.18–5.09 (m, 1H), 4.57–4.55 (m, 1H), 1.91 (t, J=7.5 Hz, 2H), 1.64–1.44 (m, 4H), 1.40–1.20 (m, 2H).

EXAMPLE 2(2)

N-hydroxy-4-(4-cyclohexylphenyl)-6-hydroxyhexanamide

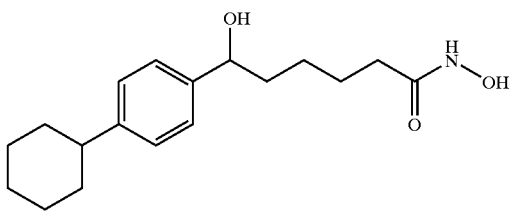

TLC: Rf 0.32 (ethyl acetate),

NMR ($d_6$-DMSO): δ 10.29 (s, 1H), 8.63 (s, 1H), 7.19 (d, J=7.8 Hz, 2H), 7.12 (d, J=7.8 Hz, 2H), 4.98 (d, J=4.5 Hz, 1H), 4.40–4.38 (m, 1H), 2.48–2.40 (m, 1H), 1.89 (t, J=7.5 Hz, 2H), 1.81–1.12 (m, 16H).

EXAMPLE 2(3)

N-hydroxy-6-(4-(4-methylphenyl)phenyl)-6-hydroxyhexanamide

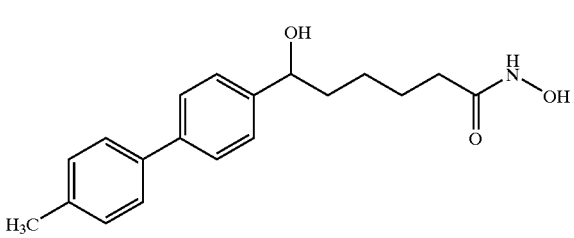

TLC: Rf 0.43 (ethyl acetate),

NMR ($d_6$-DMSO): δ 10.29 (brs, 1H), 8.62 (d, J=1.5 Hz, 1H), 7.56 (d, J=8.4 Hz, 2H), 7.53 (d, J=8.4 Hz, 2H), 7.36 (d, J=8.4 Hz, 2H), 7.25 (d, J=8.4 Hz, 2H), 5.11 (d, J=4.5 Hz, 1H), 4.54–4.48 (m, 1H), 2.33 (s, 3H), 1.91 (t, J=7.5 Hz, 2H), 1.63–1.16 (m, 6H).

EXAMPLE 2(4)

N-hydroxy-6-(4-(4-methoxyphenyl)phenyl)-6-hydroxyhexanamide

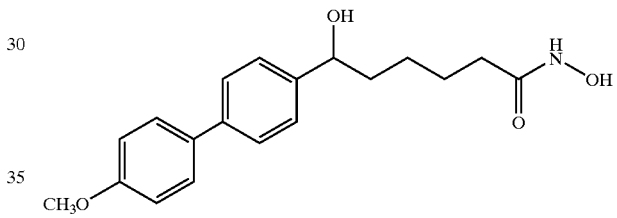

TLC: Rf 0.27 (chloroform:methanol:acetic acid=90:10:1),

NMR ($d_6$-DMSO): δ 10.29 (brs, 1H), 8.63 (d, J=1.5 Hz, 1H), 7.57 (d, J=8.1 Hz, 2H), 7.53 (d, J=8.1 Hz, 2H), 7.34 (d, J=8.1 Hz, 2H), 7.00 (d, J=8.1 Hz, 2H), 5.10 (d, J=4.5 Hz, 1H), 4.53–4.47 (m, 1H), 3.78 (s, 3H), 1.91 (t, J=7.2 Hz, 2H), 1.66–1.15 (m, 6H).

EXAMPLE 2(5)

N-hydroxy-6-(4-(trans-4-propylcycrohexyl)phenyl)-6-hydroxyhexanamide

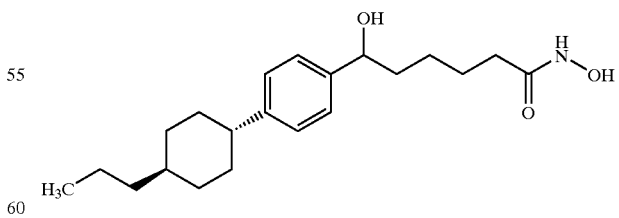

TLC: Rf 0.16 (ethyl acetate),

NMR ($d_6$-DMSO): δ 10.29 (s, 1H), 8.63 (s, 1H), 7.20 (d, J=8.5 Hz, 2H), 7.13 (d, J=8.5 Hz, 2H), 4.98 (d, J=4.4 Hz, 1H), 4.43 (m, 1H), 2.41 (m, 1H), 2.00–0.90 (m, 21H), 0.88 (t, J=7.0 Hz, 3H).

REFERENCE EXAMPLE 4

Ethyl (R)-6-(4-(4-chlorophenyl)phenyl)-6-hydroxyhexanoate

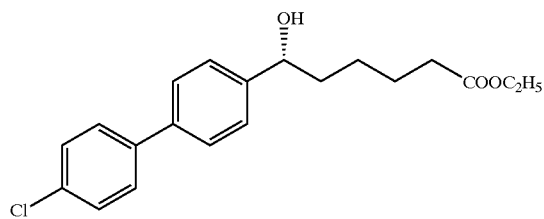

To a solution of the compound prepared in reference example 1 (17.2 g) in tetrahydrofuran (1500 mL) was added a solution of 1.0M (S)-2-methyloxazaborolidine in toluene (5 mL) at room temperature. The reaction mixture was cooled to −15° C. and a solution of 2.0M borane-dimethylsulfide complex in tetrahydrofuran (21.3 mL) was added thereto. The reaction mixture was stirred at room temperature for 3 hours. To the reaction mixture was added methanol and the mixture was stirred over night. The reaction mixture was concentrated, diluted with ethyl acetate, washed with water and a saturated aqueous solution of sodium chloride, dried over magnesium sulfate, and concentrated. The obtained residue was purified by column chromatography on silica gel (hexane:ethyl acetate=1:1) to give the title compound (17 g, 94.2% e.e., HPLC) having the following physical data.

TLC: Rf 0.25 (chloroform),

HPLC: 13.7 min (retention time), Column: DAICEL CHIRAL CELAD-RH, 4.6×150 mm; Eluant: acetonitrile:water=75:25; UV: 260 nm; Flow rate: 1.0 mL/min.

REFERENCE EXAMPLE 5

Ethyl (S)-6-(4-(4-chlorophenyl)phenyl)-6-hydroxyhexanoate

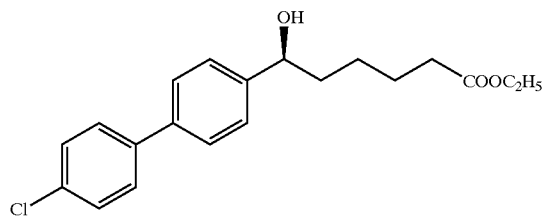

By the same procedure as a series of reactions of reference example 4 using a solution of 1.0M (R)-2-methyl-oxazaborolidine in toluene instead of a solution of 1.0M (S)-2-methyl-oxazaborolidine in toluene, the title compound (91% e.e., HPLC) having the following physical data was obtained.

TLC: Rf 0.25 (chloroform),

HPLC: 9.8 min (retention time), Column: DAICEL CHIRAL CELAD-RH, 4.6×150 mm; Eluant: acetonitrile:water=75:25; UV: 260 nm; Flow rate: 1.0 mL/min.

EXAMPLE 3

(R)-(+)-N-hydroxy-6-(4-(4-chlorophenyl)phenyl)-6-hydroxyhexanamide

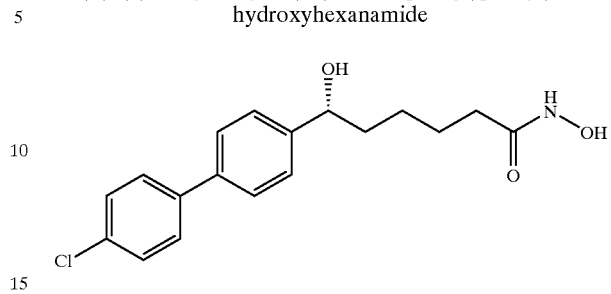

By the same procedure as a series of reactions of reference example 3→example 1→example 2 using the compound prepared in reference example 4 instead of the compound prepared in reference example 2, the compound of the present invention (98.7% e.e., HPLC) having the following physical data was obtained.

TLC: Rf 0.21 (chloroform:methanol:acetic acid=10:1:1), $[\alpha]_D$: +9.27 (c 0.280, methanol), HPLC: 16.8 min (retention time), Column: DAICEL CHIRAL CEL AD-RH, 4.6×150 mm; Eluant: acetonitrile:water=35:65; UV: 260 nm; Flow rate: 1.0 mL/min.

EXAMPLE 3(1)

(S)-(−)-N-hydroxy-6-(4-(4-chlorophenyl)phenyl)-6-hydroxyhexanamide

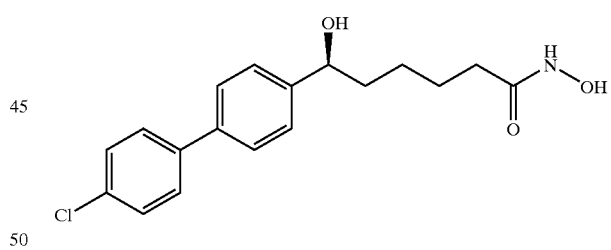

By the same procedure as a series of reactions of example 3 using the compound prepared in reference example 5 instead of the compound prepared in reference example 4, the compound of the present invention (>98% e.e., HPLC) having the following physical data was obtained.

TLC: Rf 0.21 (chloroform:methanol:acetic acid=10:1:1), $[\alpha]_D$: −9.60 (c 0.265, methanol), HPLC: 11.6 min (retention time), Column: DAICEL CHIRAL CEL AD-RH, 4.6×150 mm; Eluant: acetonitrile:water=35:65; UV: 260 nm; Flow rate: 1.0 mL/min.

REFERENCE EXAMPLE 6

N-(1-methoxy-1-methyl)ethoxy-6-(4-iodophenyl)-6-hydroxyhexanamide

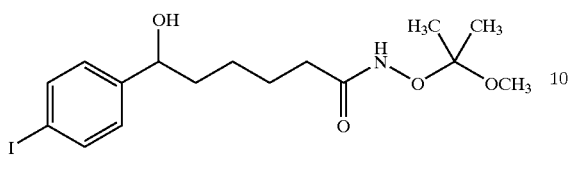

By the same procedure as a series of reactions of reference example 1→reference example 2→reference example 3→example 1 using iodobenzene instead of 4-chlorobiphenyl, the title compound having the following physical data was obtained.

TLC: Rf 0.40 (ethyl acetate),

NMR (CDCl$_3$): δ 7.69–7.63 (m, 3H), 7.08 (d, J=8.2 Hz, 2H), 4.64 (t, J=6.2 Hz, 1H), 3.31 (s, 3H), 2.42–1.21 (m, 8H), 1.41 (s, 6H).

EXAMPLE 4

N-(1-methoxy-1-methyl)ethoxy-6-(4-(benzofuran-2-yl)phenyl)-4-hydroxyhexanamide

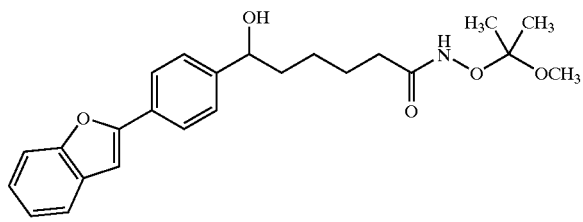

To a solution of the compound prepared in reference example 6 (440 mg) in dimethylformamide (1 0 mL) was added tri-potassium phosphate (333 mg), tetrakis(triphenylphosphine)palladium (120 mg) and benzofuran-2-boronic acid (400 mg). The reaction mixture was stirred at 60° C. for 2 hours. To the reaction mixture was added water and the mixture was extracted with ethyl acetate. The extract was washed with a saturated aqueous solution of sodium chloride, dried over sodium sulfate and concentrated. The obtained residue was purified by column chromatography on silica gel (ethyl acetate: hexane=1:1→7:3→1:0) to give the compound of the present invention (178 mg) having the following physical data.

TLC: Rf 0.39 (ethyl acetate).

EXAMPLE 5

N-hydroxy-6-(4-(benzofuran-2-yl)phenyl)-6-hydroxyhexanamide

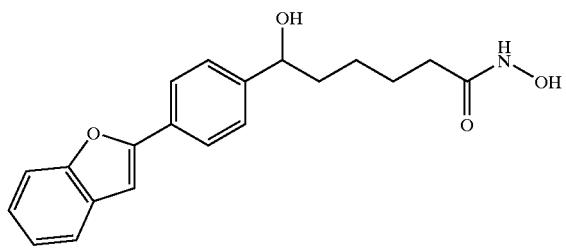

By the same procedure as a series of reactions of example 2 using the compound prepared in example 4 instead of the compound prepared in example 1, the compound of the present invention having the following physical data was obtained.

TLC: Rf 0.29 (ethyl acetate),

NMR (d$_6$-DMSO): δ 10.28 (s, 1H), 7.85 (d, J=8.1 Hz, 2H), 7.65–7.59 (m, 2H), 7.42 (d, J=8.1 Hz, 2H), 7.37 (s, 1H), 7.32–7.21 (m, 2H), 4.58–4.51 (m, 1H), 1.90 (t, J=7.2 Hz, 2H), 1.62–1.14 (m, 6H).

EXAMPLES 5(1)–5(18)

By the same procedure as a series of reactions of example 4→example 5 using a corresponding boronic acid instead of benzofuran-2-boronic acid, the following compounds of the present invention were obtained.

EXAMPLE 5(1)

N-hydroxy-6-(4-(pyridin-4-yl)phenyl)-6-hydroxyhexanamide

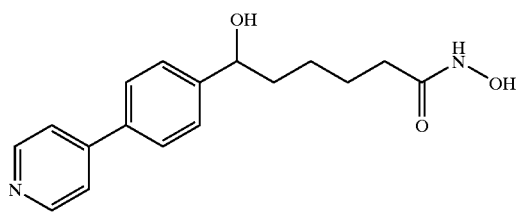

TLC: Rf 0.33 (chloroform:methanol:acetic acid=90:10:1),

NMR (d$_6$-DMSO): δ 10.30 (s, 1H), 8.63 (s, 1H), 8.61 (dd, J=4.8 Hz, 1.5 Hz, 2H), 7.74 (d, J=8.1 Hz, 2H), 7.68 (dd, J=4.8 Hz, 1.5 Hz, 2H), 7.44 (d, J=8.1 Hz, 2H), 5.21 (d, J=4.5 Hz, 1H), 4.58–4.52 (m, 1H), 1.91 (t, J=7.2 Hz, 2H), 1.64–1.14 (m, 6H).

EXAMPLE 5(2)

N-hydroxy-6-(4-(pyridin-3-yl)phenyl)-6-hydroxyhexanamide

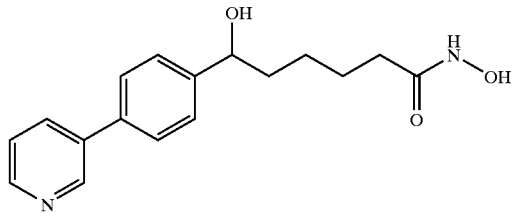

TLC: Rf 0.34 (chloroform:methanol:acetic acid=90:10:1),

NMR (d$_6$-DMSO): δ 10.29 (s, 1H), 8.86 (d, J=1.8 Hz, 1H), 8.62 (s, 1H), 8.54 (dd, J=4.8 Hz, 1.8 Hz, 1H), 8.06–8.02 (m, 1H), 7.65 (d, J=8.1 Hz, 2H), 7.48–7.43 (m, 1H), 7.42 (d, J=8.1 Hz, 2H), 5.17 (d, J=4.5 Hz, 1H), 4.56–4.50 (m, 1H), 1.90 (t, J=7.5 Hz, 2H), 1.63–1.18 (m, 6H).

EXAMPLE 5(3)

N-hydroxy-6-(4-(2-chlorophenyl)phenyl)-6-hydroxyhexanamide

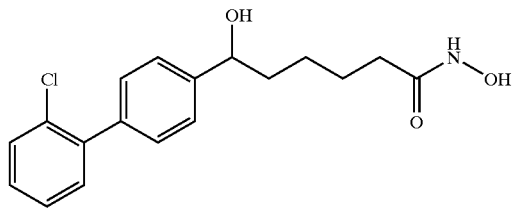

TLC: Rf 0.25 (ethyl acetate),

NMR (d$_6$-DMSO): δ 10.29 (s, 1H), 8.63 (s, 1H), 7.55–7.52 (m, 1H), 7.40–7.33 (m, 7H), 5.16 (d, J=4.5 Hz, 1H), 4.54–4.51 (m, 1H), 1.91 (t, J=6.9 Hz, 2H), 1.65–1.20 (m, 6H).

EXAMPLE 5(4)

N-hydroxy-6-(4-(3-chlorophenyl)phenyl)-6-hydroxyhexanamide

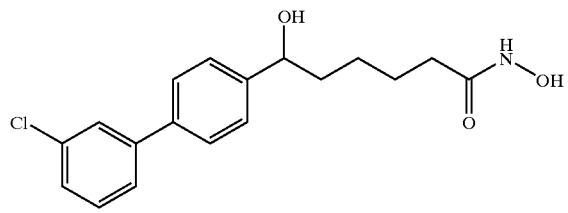

TLC: Rf 0.23 (ethyl acetate),

NMR (d$_6$-DMSO): δ 10.29 (s, 1H), 8.63 (s, 1H), 7.68 (t, J=1.8 Hz, 1H), 7.63–7.60 (m, 3H), 7.46 (t, J=8.1 Hz, 1H), 7.40–7.37 (m, 3H), 5.16 (d, J=4.2 Hz, 1H), 4.54–4.50 (m, 1H), 1.90 (t, J=7.2 Hz, 2H), 1.63–1.20 (m, 6H).

EXAMPLE 5(5)

N-hydroxy-6-(4-(4-bromophenyl)phenyl)-6-hydroxyhexanamide

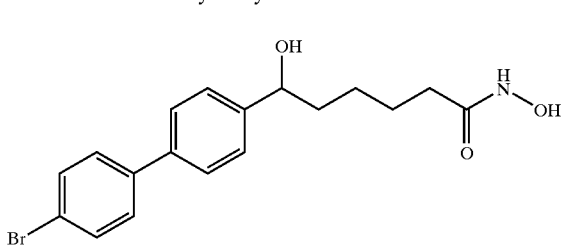

TLC: Rf 0.35 (ethyl acetate:methanol=9:1),

NMR (d$_6$-DMSO): δ 10.31 (s, 1H), 8.64 (s, 1H), 7.70–7.50 (m, 6H), 7.40 (d, J=8.4 Hz, 2H), 5.15 (d, J=4.5 Hz, 1H), 4.54 (m, 1H), 1.93 (t, J=7.2 Hz, 2H), 1.70–1.20 (m, 6H).

EXAMPLE 5(6)

N-hydroxy-6-(4-(thiophen-2-yl)phenyl)-6-hydroxyhexanamide

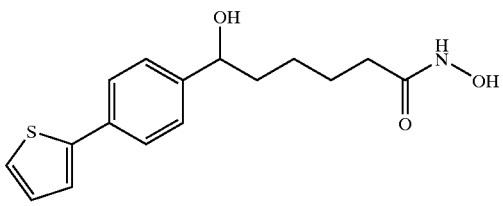

TLC: Rf 0.26 (ethyl acetate),

NMR (d$_6$-DMSO): δ 10.28 (s, 1H), 8.62 (brs, 1H), 7.57 (d, J=8.7 Hz, 2H), 7.49 (dd, J=5.1 Hz, 1.2 Hz, 1H), 7.45 (dd, J=3.6 Hz, 1.2 Hz, 1H), 7.32 (d, J=8.7 Hz, 2H), 7.10 (dd, J=5.1 Hz, 3.6 Hz, 1H), 5.13 (d, J=4.5 Hz, 1H), 4.51–4.45 (m, 1H), 1.89 (t, J=6.9 Hz, 2H), 1.60–1.15 (m, 6H).

EXAMPLE 5(7)

N-hydroxy-6-(4-(furan-2-yl)phenyl)-6-hydroxyhexanamide

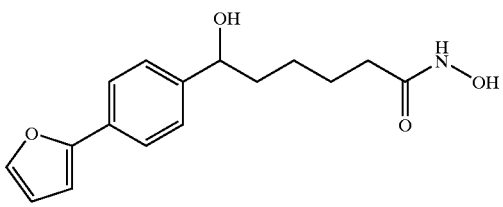

TLC: Rf 0.27 (ethyl acetate),

NMR (d$_6$-DMSO): δ 10.28 (brs, 1H), 8.65 (brs, 1H), 7.70 (d, J=2.1 Hz, 1H), 7.62 (d, J=8.4 Hz, 2H), 7.33 (d, J=8.4 Hz, 2H), 6.87 (d, J=3.6 Hz, 1H), 6.56 (dd, J=3.6 Hz, 2.1 Hz, 1H), 5.13 (d, J=4.5 Hz, 1H), 4.50–4.45 (m, 1H), 1.89 (t, J=7.2 Hz, 2H), 1.60–1.12 (m, 6H).

EXAMPLE 5(8)

N-hydroxy-6-(4-(1,3-dioxy-2,3-dihydroinden-5-yl)phenyl)-6-hydroxyhexanamide

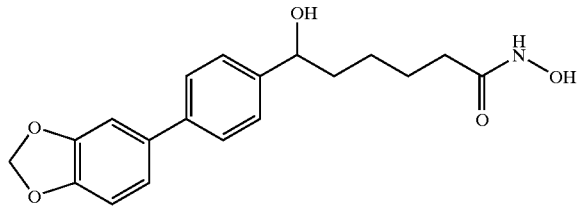

TLC: Rf 0.22 (ethyl acetate),

NMR (d$_6$-DMSO): δ 10.28 (s, 1H), 8.62 (brs, 1H), 7.51 (d, J=8.1 Hz, 2H), 7.32 (d, J=8.1 Hz, 2H), 7.21 (d, J=1.8 Hz, 1H), 7.10 (dd, J=8.1 Hz, 1.8 Hz, 1H), 6.96 (d, J=8.1 Hz, 1H), 6.03 (s, 2H), 5.10 (d, J=4.5 Hz, 1H), 4.52–4.47 (m, 1H), 1.90 (t, J=7.2 Hz, 2H), 1.60–1.12 (m, 6H).

EXAMPLE 5(9)

N-hydroxy-6-(4-(4-methylthiophenyl)phenyl)-6-hydroxyhexanamide

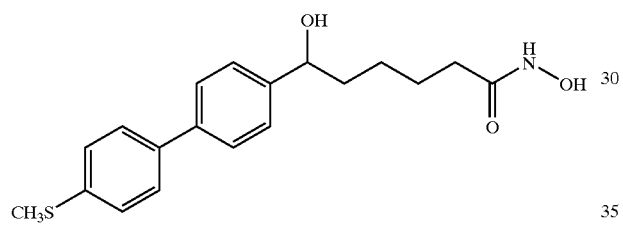

TLC: Rf 0.27 (ethyl acetate),

NMR (d$_6$-DMSO): δ 10.28 (s, 1H), 8.62 (brs, 1H), 7.59 (d, J=8.4 Hz, 2H), 7.57 (d, J=8.4 Hz, 2H), 7.36 (d, J=8.4 Hz, 2H), 7.32 (d, J=8.4 Hz, 2H), 5.12 (d, J=4.2 Hz, 1H), 4.53–4.48 (m, 1H), 3.30 (s, 3H), 1.90 (t, J=7.2 Hz, 2H), 1.62–1.16 (m, 6H).

EXAMPLE 5(10)

N-hydroxy-4-(4-(naphthalen-1-yl)phenyl)-6-hydroxyhexanamide

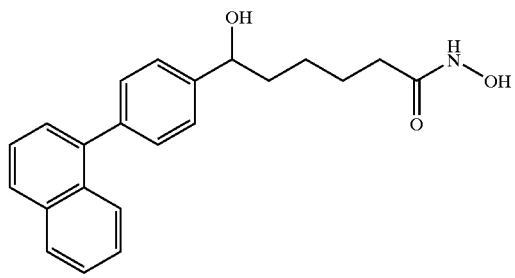

TLC: Rf 0.30 (ethyl acetate),

NMR (d$_6$-DMSO): δ 10.31 (s, 1H), 8.64 (s, 1H), 7.99–7.91 (m, 2H), 7.80 (d, J=8.1 Hz, 1H), 7.58–7.39 (m, 8H), 5.19 (d, J=4.5 Hz, 1H), 4.61–4.55 (m, 1H), 1.94 (t, J=7.5 Hz, 2H), 1.68–1.23 (m, 6H).

EXAMPLE 5(11)

N-hydroxy-6-(4-(naphthalen-2-yl)phenyl)-6-hydroxyhexanamide

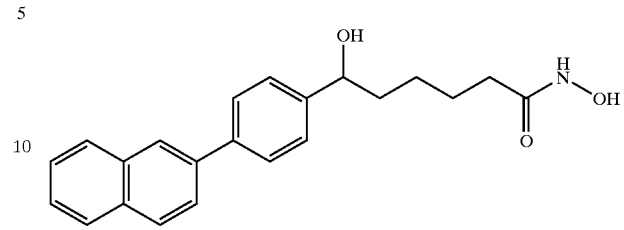

TLC: Rf 0.27 (ethyl acetate),

NMR (d$_6$-DMSO): δ 10.29 (s, 1H), 8.27 (s, 1H), 8.19 (s, 1H), 7.99–7.90 (m, 3H), 7.83 (dd, J=8.1 Hz, 1.5 Hz, 1H), 7.75 (d, J=8.1 Hz, 2H), 7.55–7.47 (m, 2H), 7.43 (d, J=8.1 Hz, 2H), 5.16 (d, J=4.2 Hz, 1H), 4.60–4.51 (m, 1H), 1.91 (t, J=7.2 Hz, 2H), 1.66–1.20 (m, 6H).

EXAMPLE 5(12)

N-hydroxy-6-(4-(4-acetylphenyl)phenyl)-6-hydroxyhexanamide

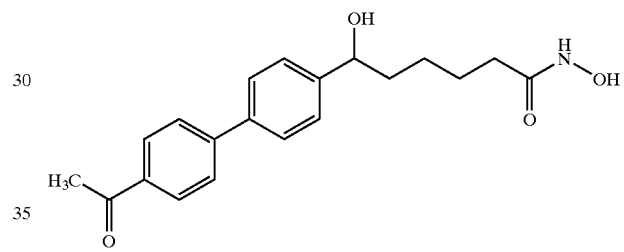

TLC: Rf 0.19 (chloroform:methanol:triethylamine=8:1:1),

NMR (d$_6$-DMSO): δ 10.31 (s, 1H), 8.64 (s, 1H), 8.03 (d, J=8.4 Hz, 2H), 7.82 (d, J=8.4 Hz, 2H), 7.70 (d, J=8.4 Hz, 2H), 7.44 (d, J=8.4 Hz, 2H), 5.18 (d, J=4.5 Hz, 1H), 4.56 (m, 1H), 2.61 (s, 3H), 1.92 (t, J=7.8 Hz, 2H), 1.70–1.42 (m, 4H), 1.42–1.18 (m, 2H).

EXAMPLE 5(13)

N-hydroxy-6-(4-(4-hydroxyphenyl)phenyl)-6-hydroxyhexanamide

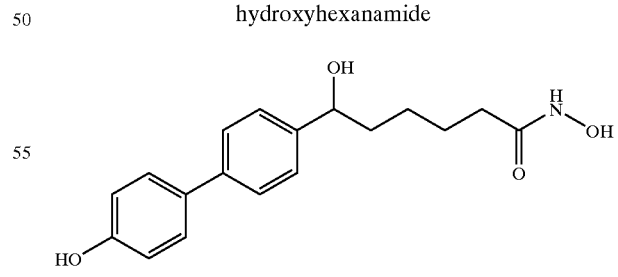

TLC: Rf 0.23 (ethyl acetate),

NMR (d$_6$-DMSO): δ 10.28 (s, 1H), 9.47 (s, 1H), 8.62 (s, 1H), 7.48 (d, J=8.4 Hz, 2H), 7.44 (d, J=8.7 Hz, 2H), 7.31 (d, J=8.4 Hz, 2H), 6.81 (d, J=8.7 Hz, 2H), 5.07 (d, J=4.2 Hz, 1H), 4.51–4.45 (m, 1H), 1.90 (t, J=7.2 Hz, 2H), 1.62–1.17 (m, 6H).

EXAMPLE 5(14)

N-hydroxy-6-(4-(dibenzofuran-4-yl)phenyl)-6-hydroxyhexanamide

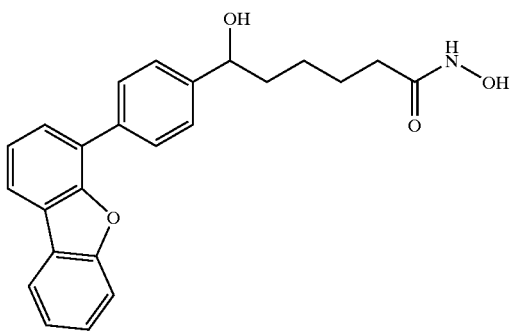

TLC: Rf 0.29 (ethyl acetate),

NMR ($d_6$-DMSO): δ 10.30 (s, 1H), 8.63 (s, 1H), 8.18 (d, J=7.2 Hz, 1H), 8.13 (dd, J=7.5 Hz, 1.2 Hz, 1H), 7.84 (d, J=8.1 Hz, 2H), 7.73 (d, J=7.2 Hz, 1H), 7.67 (dd, J=7.5 Hz, 1.2 Hz, 1H), 7.56–7.39 (m, 5H), 5.19 (d, J=4.2 Hz, 1H), 4.60–4.55 (m, 1H), 1.93 (t, J=7.2 Hz, 2H), 1.66–1.21 (m, 6H).

EXAMPLE 5(15)

N-hydroxy-6-(4-(2-methoxyphenyl)phenyl)-6-hydroxyhexanamide

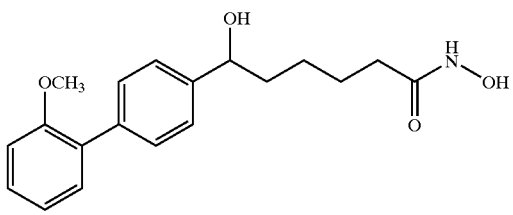

TLC: Rf 0.20 (chloroform:methanol:triethylamine=8:1:1),

NMR ($d_6$-DMSO): δ 10.31 (s, 1H), 8.65 (s, 1H), 7.40 (d, J=8.4 Hz, 2H), 7.36–7.23 (m, 2H), 7.33 (d, J=8.4 Hz, 2H), 7.10 (d, J=8.4 Hz, 1H), 7.02 (t, J=7.5 Hz, 1H), 5.11 (d, J=4.5 Hz, 1H), 4.51 (m, 1H), 3.76 (s, 3H), 1.93 (t, J=7.2 Hz, 2H), 1.68–1.15 (m, 6H).

EXAMPLE 5(16)

N-hydroxy-6-(4-(3-methoxyphenyl)phenyl)-6-hydroxyhexanamide

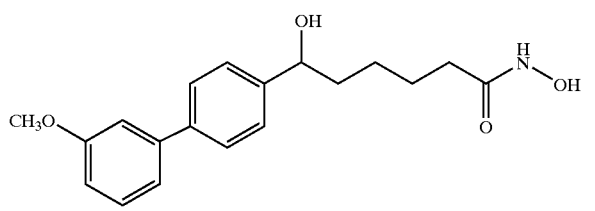

TLC: Rf 0.20 (chloroform:methanol:triethylamine=8:1:1),

NMR ($d_6$-DMSO): δ 10.30 (s, 1H), 8.64 (s, 1H), 7.60 (d, J=8.1 Hz, 2H), 7.38 (d, J=8.1 Hz, 2H), 7.36 (t, J=8.1 Hz, 1H), 7.23–7.13 (m, 2H), 6.95–6.87 (m, 1H), 5.14 (d, J=4.2 Hz, 1H), 4.53 (m, 1H), 3.80 (s, 3H), 1.92 (t, J=7.2 Hz, 2H), 1.70–1.15 (m, 6H).

EXAMPLE 5(17)

N-hydroxy-6-(4-(4-trifluoromethylphenyl)phenyl)-6-hydroxyhexanamide

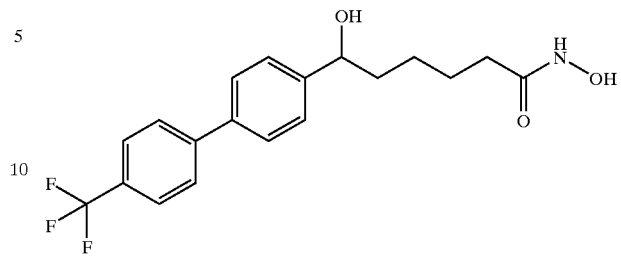

TLC: Rf 0.20 (chloroform:methanol:triethylamine=8:1:1),

NMR ($d_6$-DMSO): δ 10.31 (s, 1H), 8.65 (s, 1H), 7.89 (d, J=8.7 Hz, 2H), 7.80 (d, J=8.7 Hz, 2H), 7.69 (d, J=8.7 Hz, 2H), 7.44 (d, J=8.7 Hz, 2H), 5.20 (d, J=4.2 Hz, 1H), 4.56 (m, 1H), 1.93 (t, J=7.5 Hz, 2H), 1.70–1.15 (m, 6H).

EXAMPLE 5(18)

N-hydroxy-6-(4-(4-t-butylphenyl)phenyl)-6-hydroxyhexanamide

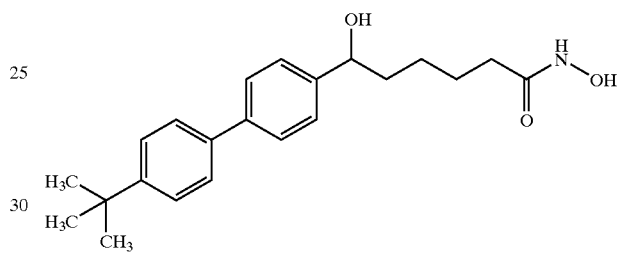

TLC: Rf 0.20 (chloroform:methanol:triethylamine=8:1:1),

NMR ($d_6$-DMSO): δ 10.31 (s, 1H), 8.64 (s, 1H), 7.57 (d, J=8.4 Hz, 4H), 7.46 (d, J=8.4 Hz, 2H), 7.38 (d, J=8.4 Hz, 2H), 5.13 (d, J=4.2 Hz, 1H), 4.52 (m, 1H), 1.92 (t, J=7.2 Hz, 2H), 1.65–1.20 (m, 6H), 1.31 (s, 9H).

REFERENCE EXAMPLE 7

2-(2-methoxyethoxy)ethyl 6-(4-bromophenyl)-6-oxohexanoate

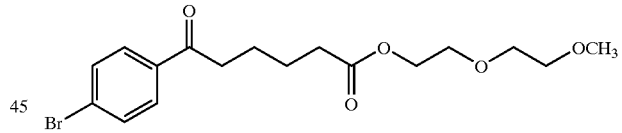

To a solution of 6-(4-bromophenyl)-6-oxohexanoic acid (52 g) in dichloromethane (200 mL) was added oxalyl chloride (32 mL). The reaction mixture was stirred at 40° C. for 3 hours. The reaction mixture was concentrated. A solution of the obtained residue in toluene (500 mL) was dropped to di(ethylene glycol)methyl ether (65 mL) at 0° C. The reaction mixture was stirred at room temperature overnight and triethylamine (25 mL) was dropped thereto at room temperature. The reaction mixture was stirred at room temperature for 1 hour. The reaction mixture was poured into water and extracted with ethyl acetate. The extract was washed with water and a saturated aqueous solution of sodium chloride, dried over anhydrous magnesium sulfate and concentrated. To the obtained residue was added methanol and the precipitate was filtrated. The filtrate was concentrated to give the title compound (88 g) having the following physical data.

TLC: Rf 0.43 (hexane:ethyl acetate=2:3),

NMR (CDCl$_3$): δ 7.81 (d, J=8.7 Hz, 2H), 7.60 (d, J=8.7 Hz, 2H), 4.24 (t, J=4.8 Hz, 2H), 3.69 (t, J=4.8 Hz, 2H), 3.66–3.62 (m, 2H), 3.56–3.53 (m, 2H), 3.38 (s, 3H), 2.95 (t, J=7.2 Hz, 2H), 2.40 (t, J=7.2 Hz, 2H), 1.83–1.67 (m, 4H).

REFERENCE EXAMPLE 8

2-(2-methoxyethoxy)ethyl 6-[4-(N-(2-hydroxy-5-methylphenyl)carbamoyl)phenyl]-6-oxohexanoate

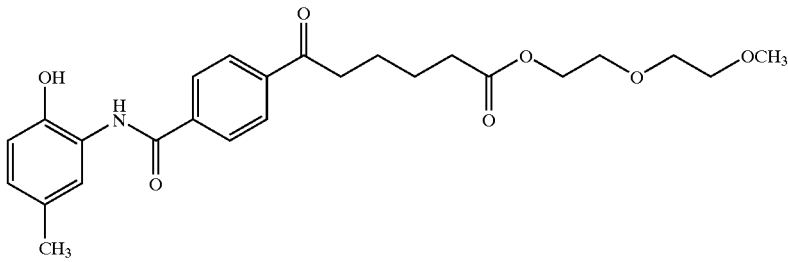

Under an atmosphere of argon, to a solution of compound prepared in reference example 7 (75 g) in dimethylacetamide (300 mL) was added 4-methyl-2-aminophenol (17.9 g), dichlorobis(triphenylphosphine)palladium(II) (2.78 g), triphenylphosphine (2.07 g), 1,8-diazabicyclo[5.4.0]undec-7-ene (23.7 mL). The atmosphere of argon was replaced with carbon monoxide. The reaction mixture was stirred at 150° C. for 2.5 hours. The reaction mixture was poured into water and extracted with ethyl acetate. The extract was washed with 1N hydrochloric acid water and a saturated aqueous solution of sodium chloride, dried over anhydrous magnesium sulfate and concentrated. The obtained residue was washed with diethyl ether to give the title compound (51.3 g) having the following physical data.

TLC: Rf 0.27 (hexane:ethyl acetate=1:2),

NMR (CDCl$_3$): δ 8.29 (brs, 1H), 8.04 (d, J=8.7 Hz, 2H), 8.00–7.98 (m, 1H), 7.97 (d, J=8.7 Hz, 2H), 7.19 (s, 1H), 6.98–6.93 (m, 2H), 4.24 (t, J=5.0 Hz, 2H), 3.70 (t, J=5.0 Hz, 2H), 3.66–3.63 (m, 2H), 3.56–3.53 (m, 2H), 3.37 (s, 3H), 3.02 (t, J=6.9 Hz, 2H), 2.40 (t, J=6.9 Hz, 2H), 2.29 (s, 3H), 1.86–1.68 (m, 4H).

REFERENCE EXAMPLE 9

2-(2-methoxyethoxy)ethyl 6-[4-(5-methylbenzoxazol-2-yl)phenyl]-6-oxohexanoate

To a suspension of the compound prepared in reference example 8 (49 g) in toluene (500 mL) was added camphor sulfonic acid (24.9 g). The reaction mixture was stirred at 150° C. for 3.5 hours with dehydrating with Dean-Stark. The reaction mixture was poured into ice water and extracted with ethyl acetate. The extract was washed with a saturated aqueous solution of sodium hydrogen carbonate, water and a saturated aqueous solution of sodium chloride, dried over anhydrous magnesium sulfate and concentrated. The obtained residue was purified by column chromatography on silica gel (dichloromethane:ethyl acetate=10:1~1:1) to give the title compound (33.1 g) having the following physical data.

TLC: Rf 0.42 (hexane:ethyl acetate=1:2),

NMR (CDCl$_3$): δ 8.33 (d, J=8.7 Hz, 2H), 8.08 (d, J=8.7 Hz, 2H), 7.58 (d, J=1.5 Hz, 1H), 7.48 (d, J=8.1 Hz, 1H), 7.20 (dd, J=8.1, 1.5 Hz, 1H), 4.25 (t, J=4.8 Hz, 2H), 3.70 (t, J=4.8 Hz, 2H), 3.66–3.62 (m, 2H), 3.57–3.53 (m, 2H), 3.38 (s, 3H), 3.05 (t, J=7.0 Hz, 2H), 2.50 (s, 3H), 2.42 (t, J=7.0 Hz, 2H), 1.87–1.70 (m, 4H).

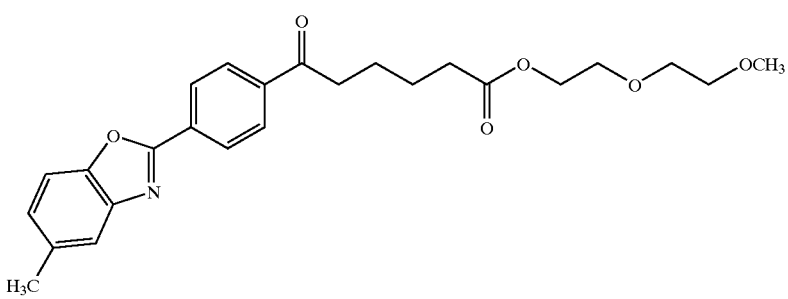

REFERENCE EXAMPLE 9(1)

2-(2-methoxyethoxy)ethyl 6-[4-(benzoxazol-2-yl)phenyl]-6-oxohexanoate

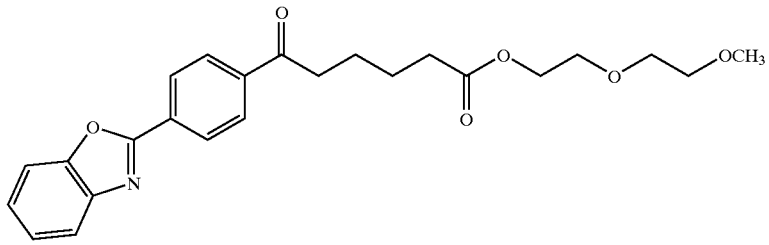

By the same procedure as a series of reactions of reference example 8→reference example 9 using 2-aminophenol instead of 4-methyl-2-aminophenol, the title compound having the following physical data were obtained.

TLC: Rf 0.45 (hexane:ethyl acetate=2:3),

NMR (CDCl$_3$): δ 8.35,(d, J=8.8 Hz, 2H), 8.09 (d, J=8.8 Hz, 2H), 7.85–7.77 (m, 1H), 7.67–7.58 (m, 1H), 7.45–7.37 (m, 2H), 4.24 (t, J=4.8 Hz, 2H), 3.72 (t, J=4.8 Hz, 2H), 3.67–3.62 (m, 2H), 3.58–3.53 (m, 2H), 3.38 (s, 3H), 3.05 (t, J=7.0 Hz, 2H), 2.42 (t, J=7.0 Hz, 2H), 1.90–1.70 (m, 4H).

REFERENCE EXAMPLE 10

2-(2-methoxyethoxy)ethyl 6-[4-(2-(4-methylthiophenyl)ethynyl)phenyl]-6-oxohexanoate

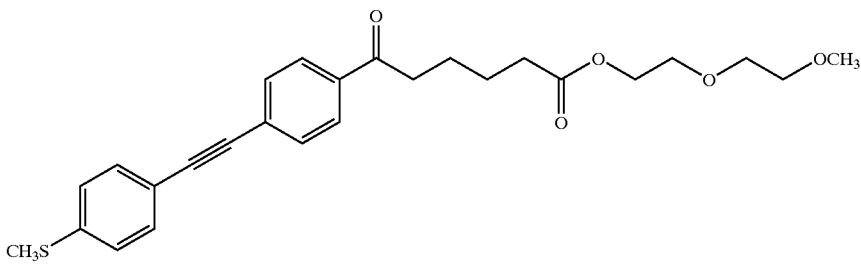

Under an atmosphere of argon, to a mixture solution of the compound prepared in reference example 7 (80 g) in dimethylformamide (310 mL) and triethylamine (155 mL) was added 1-ethynyl-4-methylthiobenzene (27.5 g) and dichlorobis(triphenylphosphine)palladium(II) (10.9 g). The reaction mixture was stirred at 50° C. for 3 hours. The reaction mixture was poured into an aqueous solution of 2N hydrochloric acid cooled with ice and extracted with ethyl acetate. The extract was washed with 2N hydrochloric acid, a saturated aqueous solution of sodium hydrogen carbonate and a saturated aqueous solution of sodium chloride, dried over anhydrous magnesium sulfate and concentrated. The obtained residue was purified by column chromatography on silica gel (hexane:ethyl acetate=2:1~2:3→chloroform:methanol=20:1) to give the title compound (41.1 g) having the following physical data.

TLC: Rf 0.21 (hexane:ethyl acetate=2:1),

NMR (CDCl$_3$): δ 7.93 (d, J=8.6 Hz, 2H), 7.59 (d, J=8.6 Hz, 2H), 7.46 (d, J=8.6 Hz, 2H), 7.22 (d, J=8.6 Hz, 2H), 4.28–4.20 (m, 2H), 3.75–3.60 (m, 4H), 3.60–3.50 (m, 2H), 3.38 (s, 3H), 2.99 (t, J=7.0 Hz, 2H), 2.51 (s, 3H), 2.41 (t, J=7.0 Hz, 2H), 1.85–1.65 (m, 4H).

REFERENCE EXAMPLE 11

2-(2-methoxyethoxy)ethyl 6-[4-(4-methylthiophenyl)phenyl]-6-oxohexanoate

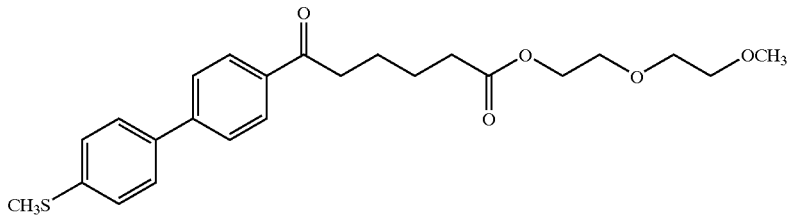

By the same procedure as a series of reactons of example 4 using the compound prepared in reference example 7 and 4-methylthiophenylboronic acid, the title compound having the following physical data was obtained.

TLC: Rf 0.24 (hexane:ethyl acetate=1:1),

NMR (CDCl₃): δ 8.01 (d, J=8.7 Hz, 2H), 7.65 (d, J=8.7 Hz, 2H), 7.56 (d, J=8.4 Hz, 2H), 7.34 (d, J=8.4 Hz, 2H), 4.25 (t, J=4.8 Hz, 2H), 3.70 (t, J=4.8 Hz, 2H), 3.66–3.63 (m, 2H), 3.56–3.53 (m, 2H), 3.38 (s, 3H), 3.01 (t, J=6.9 Hz, 2H), 2.53 (s, 3H), 2.41 (t, J=6.9 Hz, 2H), 1.86–1.70 (m, 4H).

REFERENCE EXAMPLE 12

Methyl 6-[4-(4-methylthiophenyl)phenyl]-6-oxohexanoate

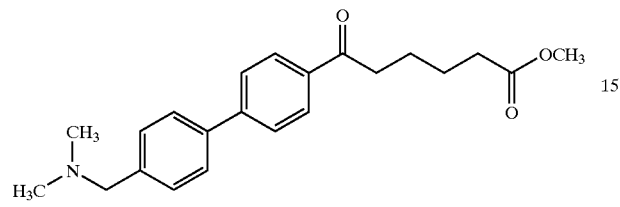

By the same procedure as a series of reactions of reference example 1 using monomethyl adipate and 4-(N,N-dimethylamino)methylbiphenyl, the title compound having the following physical data was obtained.

TLC: Rf 0.51 (dichloromethane:methanol=4:1),

NMR (CDCl₃): δ 8.01 (d, J=8.7 Hz, 2H), 7.68 (d, J=8.7 Hz, 2H), 7.59 (d, J=8.3 Hz, 2H), 7.42 (d, J=8.3 Hz, 2H), 3.67 (s, 3H), 3.50 (s, 2H), 3.02 (t, J=7.0 Hz, 2H), 2.39 (t, J=7.0 Hz, 2H), 2.29 (s, 6H), 1.86–1.70 (m, 4H).

EXAMPLE 6

(R)-(+)-N-(1-methoxy-1-methyl)ethoxy-6-[4-(5-methylbenzoxaiol-2-yl)phenyl]-6-hydroxyhexanamide

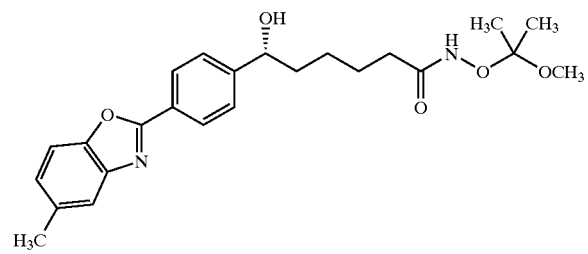

By the same procedure as a series of reactions of reference example 4→reference example 3→example 1 using the compound prepared in reference example 9, the compound of the present invention having the following physical data was obtained.

[α]_D: +22.46 (c 0.615, dimethylformamide),

TLC: Rf 0.34 (ethyl acetate),

NMR (CDCl₃): δ 8.19 (d, J=8.1 Hz, 2H), 7.84 (brs, 1H), 7.54–7.53 (m, 1H), 7.47 (d, J=8.1 Hz, 2H), 7.44 (d, J=8.1 Hz, 1H), 7.16–7.13 (m, 1H), 4.80–4.75 (m, 1H), 3.30 (s, 3H), 2.48 (s, 3H), 2.42–2.08 (m, 2H), 1.94–1.32 (m, 6H), 1.41 (s, 6H).

EXAMPLES 6(1)–6(4)

By the same procedure as a series of reactions of example 6 using the compound prepared in reference example 9(1), 10, 11 or 12 instead of the compound prepared in reference example 9, the compounds of the present invention having the following physical data were obtained.

EXAMPLE 6(1)

(R)-N-(1-methoxy-1-methyl)ethoxy-6-[4-(benzoxazol-2-yl)phenyl]-6-hydroxyhexanamide

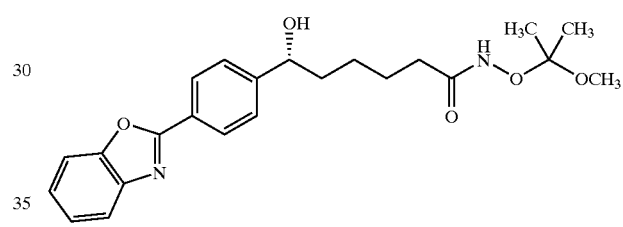

TLC: Rf 0.50 (chloroform:methanol:acetic acid=90:10:1),

NMR (CDCl₃): δ 8.22 (d, J=8.2 Hz, 2H), 7.83 (br, 1H), 7.75 (m, 1H), 7.59 (m, 1H), 7.49 (d, J=8.2 Hz, 2H), 7.35 (m, 2H), 4.76 (t, J=6.5 Hz, 1H), 3.30 (s, 3H), 2.45–2.12 (m, 2H), 1.85–1.62 (m, 4H), 1.53–1.38 (m, 2H), 1.41 (s, 6H).

EXAMPLE 6(2)

(R)-N-(1-methoxy-1-methyl)ethoxy-6-[4-(2-(4-methylthiophenyl)ethynyl)phenyl]-6-hydroxyhexanamide

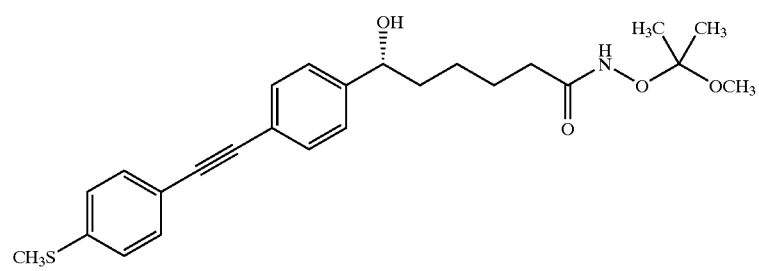

TLC: Rf 0.41 (chloroform:methanol:acetic acid= 90:10:1),

NMR (CDCl$_3$): δ 7.86 (br, 1H), 7.48 (d, J=8.4 Hz, 2H), 7.42 (d, J=8.4 Hz, 2H), 7.30 (d, J=8.4 Hz, 2H), 7.20 (d, J=8.4 Hz, 2H), 4.68 (t-like, J=6.0 Hz, 1H), 3.31 (s, 3H), 2.49 (s, 3H), 2.40–2.10 (m, 2H), 1.82–1.65 (m, 4H), 1.50–1.35 (m, 2H), 1.41 (s, 6H).

EXAMPLE 6(3)

(R)-N-(1-methoxy-1-methyl)ethoxy-6-[4-(4-methylthiophenyl)phenyl]-6-hydroxyhexanamide

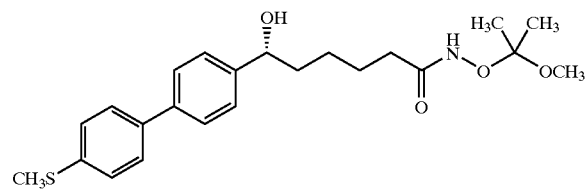

TLC: Rf 0.44 (ethyl acetate),

NMR (CDCl$_3$): δ 7.79 (br, 1H), 7.53 (d, J=8.5 Hz, 2H), 7.51 (d, J=8.5 Hz, 2H), 7.38 (d, J=8.5 Hz, 2H), 7.31 (d, J=8.5 Hz, 2H), 4.71 (t, J=6.0 Hz, 1H), 3.30 (s, 3H), 2.52 (s, 3H), 2.43–2.08 (m, 2H), 1.90–1.65 (m, 5H), 1.57–1.36 (m, 1H), 1.41 (s, 6H).

EXAMPLE 6(4)

(R)-(+)-N-(1-methoxy-1-methyl)ethoxy-6-[4-(4-(dimethylaminomethyl)phenyl)phenyl]-6-hydroxyhexanamide

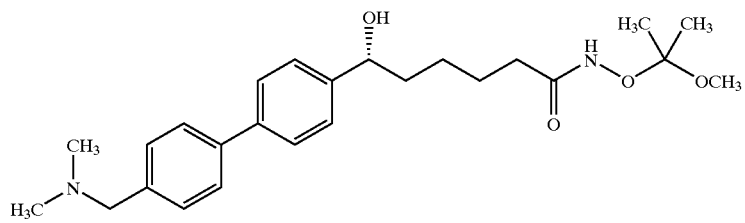

[α]$_D$: +22.6 (c 1.04, dimethylformamide),

TLC: Rf 0.17 (chloroform:methanol=9:1),

NMR (d$_6$-DMSO): δ 7.58 (d, J=8.1 Hz, 2H), 7.57 (d, J=8.1 Hz, 2H), 7.36 (d, J=8.1 Hz, 2H), 7.34 (d, J=8.1 Hz, 2H), 5.12 (d, J=4.5 Hz, 1H), 4.52 (m, 1H), 3.39 (s, 2H), 3.18 (s, 3H), 2.14 (s, 6H), 1.98 (t, J=7.2 Hz, 2H), 1.65–1.54 (m, 2H), 1.49 (m, 2H), 1.40–1.18 (m, 2H), 1.24 (s, 6H).

EXAMPLE 7

(R)-(+)-N-hydroxy-6-[4-(5-methylbenzoxazol-2-yl)phenyl]-6-hydroxyhexanamide

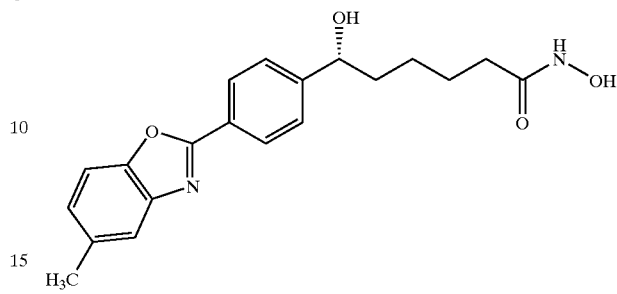

By the same procedure as a series of reactions of example 2 using the compound prepared in example 6, the compound of the present invention having the following physical data was obtained.

TLC: Rf 0.28 (chloroform:methanol=9:1), m.p.: 178–179° C.,

[α]$_D$: +31.0 (c 1.05, dimethylformamide),

NMR (d$_6$-DMSO): δ 10.30 (s, 1H), 8.63 (s, 1H), 8.12 (d, J=8.4 Hz, 2H), 7.63 (d, J=8.4 Hz, 1H), 7.57 (m, 1H), 7.53 (d, J=8.4 Hz, 2H), 7.22 (m, 1H), 5.31 (d, J=4.2 Hz, 1H), 4.59 (m, 1H), 2.43 (s, 3H), 1.91 (t, J=7.2 Hz, 2H), 1.65–1.56 (m, 2H), 1.54–1.45 (m, 2H), 1.41–1.18 (m, 2H).

EXAMPLES 7(1)~7(4)

By the same procedure as a series of reactions of example 7 using the compound prepared in example 6(1)–(4) instead of the compound prepared in example 6, if desired, the conversion into the acid addition salts by conventional means, the following compounds of the present invention were obtained.

EXAMPLE 7(1)

(R)-(+)-N-hydroxy-6-[4-benzoxazol-2-yl)phenyl]-6-hydroxyhexanamide

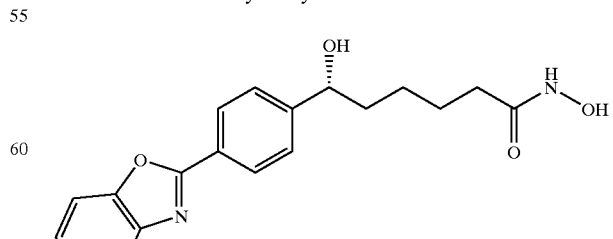

TLC: Rf 0.20 (chloroform:methanol:acetic acid= 90:10:1), m.p.: 160~161° C.,

[α]$_D$: +10.10 (c 0.81, methanol),

NMR (d$_6$-DMSO): δ 10.31 (s, 1H), 8.64 (s, 1H), 8.14 (d, J=8.2 Hz, 2H), 7.82–7.72 (m, 2H), 7.54 (d, J=8.2 Hz, 2H), 7.47–7.34 (m, 2H), 5.32 (d, J=4.4 Hz, 1H), 4.64–4.57 (m, 1H), 1.92 (t, J=7.0 Hz, 2H), 1.70–1.10 (m, 6H).

EXAMPLE 7(2)

(R)-(+)-N-hydroxy-6-[4-(2-(4-methylthiophenyl)ethynyl)phenyl]-6-hydroxyhexanamide

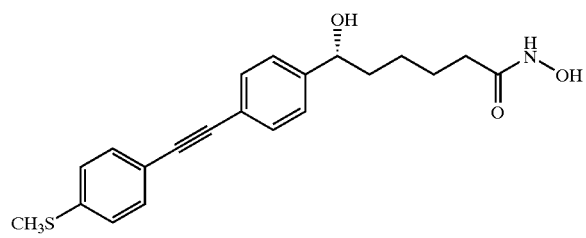

TLC: Rf 0.43 (chloroform:methanol:acetic acid=60:10:1), m.p.: 173~176° C.,

[α]$_D$: +31.5 (c 1.02, dimethylformamide),

NMR (d$_6$-DMSO): δ 10.30 (s, 1H), 8.62 (s, 1H), 7.48 (d, J=8.0 Hz, 2H), 7.47 (d, J=8.4 Hz, 2H), 7.35 (d, J=8.0 Hz, 2H), 7.28 (d, J=8.4 Hz, 2H), 5.22 (d, J=4.4 Hz, 1H), 4.60–4.45 (m, 1H), 2.51 (s, 3H), 1.92 (t, J=7.2 Hz, 2H), 1.70–1.10 (m, 6H).

EXAMPLE 7(3)

(R)-(+)-N-hydroxy-6-[4-(4-methylthiophenyl)phenyl]-6-hydroxyhexanamide

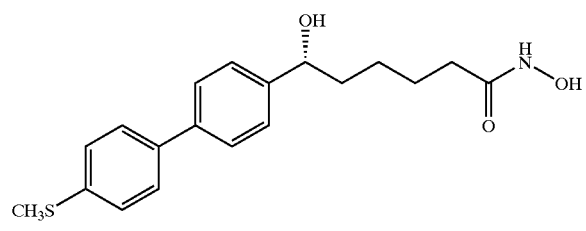

TLC: Rf 0.23 (chloroform:methanol=9:1), m.p.: 194~197° C.,

[α]$_D$: +6.86 (c 0.105, methanol),

NMR (d$_6$-DMSO): δ 10.29 (s, 1H), 8.62 (s, 1H), 7.61–7.55 (m, 4H), 7.38–7.29 (m, 4H), 5.12 (d, J=4.4 Hz, 1H), 4.58–4.42 (m, 1H), 2.49 (s, 3H), 1.90 (t, J=7.4 Hz, 2H), 1.66–1.02 (m, 6H).

EXAMPLE 7(4)

(R)-(+)-N-hydroxy-6-[4-(4-(dimethylaminomethyl)phenyl)phenyl]-6-hydroxyhexanamide.hydrochloride

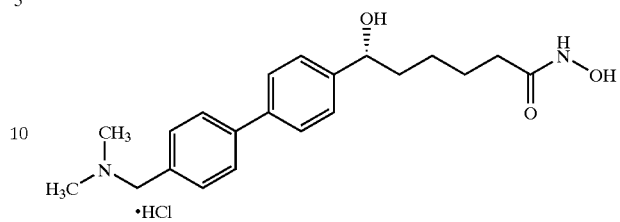

TLC: Rf 0.14 (chloroform:methanol=2:1), m.p.: 214~217° C.,

[α]$_D$: +26.54 (c 0.11, methanol),

NMR (d$_6$-DMSO): δ 10.79 (s, 1H), 10.33 (s, 1H), 8.63 (s, 1H), 7.73 (d, J=8.2 Hz, 2H), 7.64–7.62 (m, 4H), 7.39 (d, J=8.2 Hz, 2H), 5.17 (d, J=3.9 Hz, 1H), 4.58–4.49 (m, 1H), 4.27 (s, 2H), 2.68 (s, 6H), 1.91 (t, J=6.9 Hz, 2H), 1.64–1.18 (m, 2H).

EXAMPLES 8(1)~8(4)

By the same procedure as a series of reactions of reference example 1→reference example 2→reference example 3→example 1→example 2 using a corresponding compound instead of 4-chlorobiphenyl, the following compounds of the present invention were obtained.

EXAMPLE 8(1)

N-hydroxy-6-(4-(trans-4-butylcyclohexyl)phenyl)-6-hydroxyhexanamide

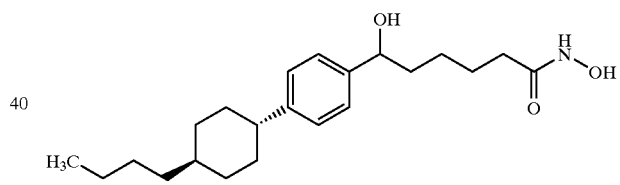

TLC: Rf 018 (ethyl acetate),

NMR (d$_6$-DMSO): δ 10.30 (s, 1H), 8.63 (s, 1H), 7.20 (d, J=8.2 Hz, 2H), 7.13 (d, J=8.2 Hz, 2H), 4.99 (d, J=3.9 Hz, 1H), 4.42 (m, 1H), 2.40 (m, 1H), 1.91 (t, J=7.2 Hz, 2H), 1.90–0.90 (m, 21H), 0.85 (t, J=6.9 Hz, 3H).

EXAMPLE 8(2)

N-hydroxy-6-(4-(trans-4-hydroxycyclohexyl)phenyl)-6-hydroxyhexanamide

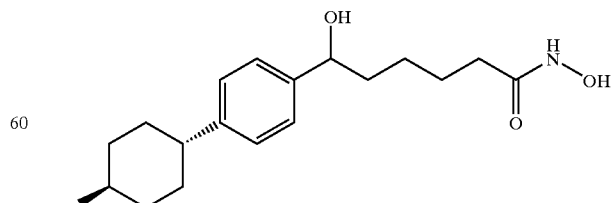

TLC: Rf 0.12 (chloroform:methanol:triethylamine=8:1:1),

NMR (d$_6$-DMSO): δ 10.29 (s, 1H), 8.64 (s, 1H), 7.19 (d, J=8.1 Hz, 2H), 7.13 (d, J=8.1 Hz, 2H), 4.99 (d, J=4.5 Hz, 1H), 4.54 (d, J=4.5 Hz, 1H), 4.42 (q, J=4.5 Hz, 1H), 3.52–3.36 (m, 1H), 2.60–2.30 (m, 1H), 1.95–1.83 (m, 4H), 1.80–1.65 (m, 2H), 1.63–1.10 (m, 10H).

EXAMPLE 8(3)

N-hydroxy-6-(4-cyclopentylphenyl)-6-hydroxyhexanamide

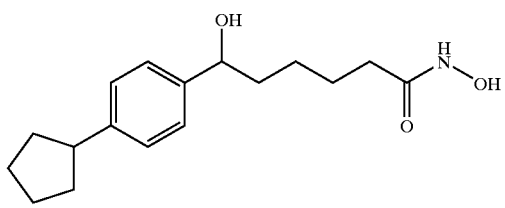

TLC: Rf 0.18 (chloroform:methanol:triethylamine= 8:1:1),

NMR (d$_6$-DMSO): δ 10.29 (s, 1H), 8.64 (s, 1H), 7.20 (d, J=8.4 Hz, 2H), 7.16 (d, J=8.4 Hz, 2H), 5.00 (d, J=3.9 Hz, 1H), 4.43 (q, J=3.9 Hz, 1H), 3.00–2.85 (m, 1H), 2.06–1.84 (m, 4H), 1.83–1.38 (m, 10H), 1.38–1.10 (m. 2H).

EXAMPLE 8(4)

N-hydroxy-6-[4-(morpholin-4-yl)phenyl]-6-hydroxyhexanamide

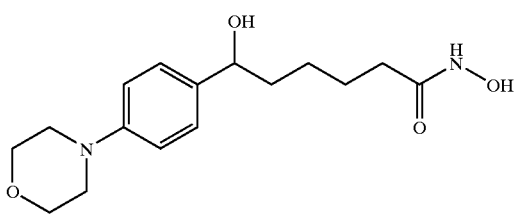

TLC: Rf 0.20 (chloroform:methanol=9:1),

NMR (d$_6$-DMSO): δ 10.27 (s, 1H), 8.61 (s, 1H), 7.14 (d, J=8.7 Hz, 2H), 6.85 (d, J=8.7 Hz, 2H), 4.80 (d, J=4.2 Hz, 1H), 4.40–4.35 (m, 1H), 3.72–3.69 (m, 4H), 3.05–3.02 (m, 4H), 1.88 (t, J=7.5 Hz, 2H), 1.62–1 .07 (m, 6H).

EXAMPLE 9

N-hydroxy-6-[3-(4-chlorophenyl)phenyl]-6-hydroxyhexanamide

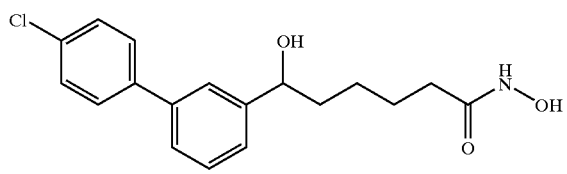

By the same procedure as a series of reactions of example 4→reference example 2→reference example 3→example 1→example 2 using methyl 6-(3-bromophenyl)-6-oxohexanoate instead of the compound prepared in reference example 6, the compound of the present invention having the following physical data was obtained.

TLC: Rf 0.27 (ethyl acetate),

NMR (d$_6$-DMSO): δ 10.28 (brs, 1H), 8.62 (brs, 1H), 7.75–7.64 (m, 3H), 7.57 (s, 1H), 7.52–7.47 (m, 2H), 7.39 (t, J=7.5 Hz, 1H), 7.31 (d, J=6.9 Hz, 1H), 5.16 (d, J=4.5 Hz, 1H), 4.58–4.52 (m, 1H), 1.90 (t, J=7. 2 Hz, 2H), 1.64–1.20 (m, 6H).

EXAMPLE 9(1)

N-hydroxy-6-[2-(4-chlorophenyl)phenyl]-6-hydroxyhexanamide

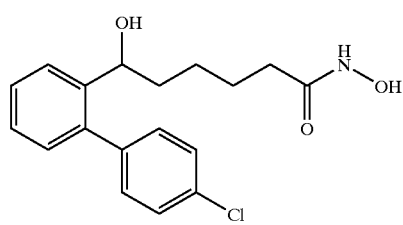

By the same procedure as a series of reactions of example 9 using methyl 6-(2-bromophenyl)-6-oxohexanoate instead of methyl 6(3-bromophenyl)-6-oxohexanoate, the compound of the present invention having the following physical data was obtained.

TLC: Rf 0.26 (ethyl acetate),

NMR (d$_6$-DMSO): δ 10.24 (s, 1H), 8.61 (s, 1H), 7.56 (d, J=7.5 Hz, 1H), 7.49–7.46 (m, 2H), 7.40–7.24 (m, 4H), 7.11–7.09 (m, 1H), 5.03 (d, J=4.2 Hz, 1H), 4.49–4.44 (m, 1H), 1.80 (t, J=7.5 Hz, 2H), 1.56–1.02 (m, 6H).

EXAMPLE 10

N-hydroxy-6-[4-((1E)-2-phenylvinyl)phenyl]-6-hydroxyhexanamide

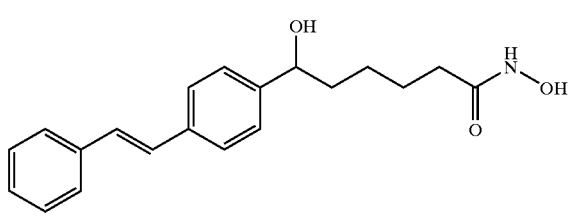

By the same procedure as a series of reactions of reference example 10→example 2 using the compound prepared in reference example 6 and styrene, the compound of the present invention having the following physical data was obtained.

TLC: Rf 0.34 (ethyl acetate),

NMR (d$_6$-DMSO): δ 10.28 (s, 1H), 7.59–7.51 (m, 4H), 7.38–7.21 (m, 5H), 7.21 (s, 1 2H), 4.49–4.45 (m, 1H), 1.89 (t, J=7.5 Hz, 2H), 1.601.12 (m, 6H).

EXAMPLES 10(1) AND 10(2)

By the same procedure as a series of reactions of example 10 using a corresponding compound instead of styrene, the following compounds of the present invention were obtained.

EXAMPLE 10(1)

N-hydroxy-6-[4-((1E)-2-(pyridinyl)vinyl)phenyl]-6-hydroxyhexanamide

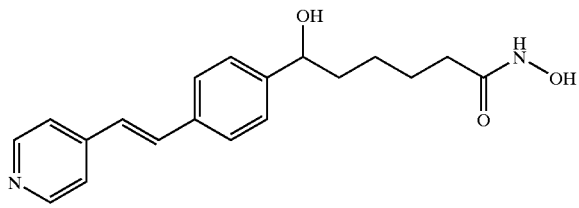

TLC: Rf 0.22 (ethyl acetate:methanol 9:1),

NMR (d$_6$-DMSO): δ 10.28 (s, 1H), 8.62 (s, 1H), 8.51 (d, J=5.4 Hz, 2H), 7.58 (d, J=8.1 Hz, 2H), 7.53 (d, J=5.4 Hz, 2H), 7.51 (d, J=16.2 Hz, 1H), 7.33 (d, J=8.1 Hz, 2H), 7.19 (d, J=16.2 Hz, 1H), 5.14 (d, J=4.8 Hz, 1H), 4.52–4.46 (m, 1H), 1.89 (t, J=7.5 Hz, 2H), 1.60–1.10 (m, 6H).

EXAMPLE 10(2)

N-hydroxy-6-[4-((1E)-2-(pyridin-2-yl)vinyl)phenyl]-6-hydroxyhexanamide

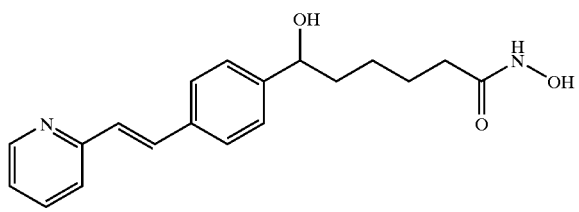

TLC: Rf 0.22 (ethyl acetate:methanol=9:1),

NMR (d$_6$-DMSO): δ 10.29 (s, 1H), 8.63 (s, 1H), 8.56–8.54 (m, 1H), 7.77 (dt, J=7.5 Hz, 1.5 Hz, 1H), 7.64 (d, J=16.2 Hz, 1H), 7.59 (d, J=7.8 Hz, 2H), 7.52 (d, J=8.1 Hz, 1H), 7.32 (d, J=7.8 Hz, 2H), 7.27 (d, J=16.2 Hz, 1H), 7.25–7.21 (m, 1H), 5.13 (d, J=4.5 Hz, 1H), 4.52–4.80 (m, 1H), 1.90 (t, J=7.5 Hz, 2H), 1.63–1.18 (m, 6H).

REFERENCE EXAMPLE 13

6-[4-(4-chlorophenyl)phenyl]-6-oxohexanoic acid

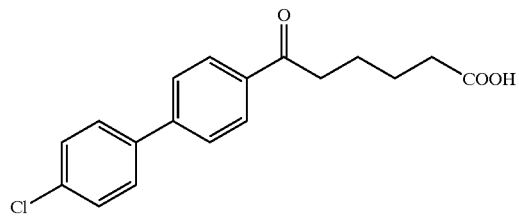

By the same procedure as a series of reactions of reference example 3 using the compound prepared in reference example 1, the title compound having the following physical data was obtained.

TLC: Rf 0.50 (ethyl acetate),

NMR (d$_6$-DMSO) δ 12.00 (s, 1H), 8.05 (d, J=8.4 Hz, 2H), 7.82 (d, J=8.4 Hz, 2H), 7.79 (d, J=8.4 Hz, 2H), 7.56 (d, J=8.4 Hz, 2H), 3.07 (t, J=6.6 Hz, 2H), 2.27 (t, J=7.4 Hz, 2H), 1.80–1.50 (m, 4H).

REFERENCE EXAMPLE 14

6-[4-(4-chlorophenyl)phenyl]-6-hydroxy heptanoic acid

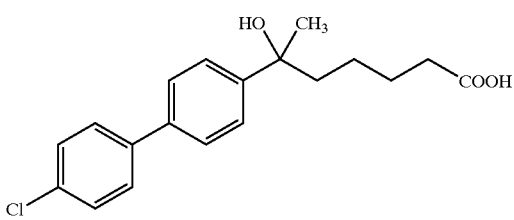

Under an atmosphere of argon, to a solution of the compound prepared in reference example 13 (560 mg) in tetrahydrofuran (20 mL) was added 0.82 mmol/mL solution of methylmagnesium iodide in diethylether (10.8 mL) at 0° C. The reaction mixture was stirred at room temperature for 1 hour. To the reaction mixture was added 1N hydrochloric acid and the mixture was extracted with ethyl acetate. The extract was washed with water and a saturated aqueous solution of sodium chloride, dried over anhydrous magnesium sulfate, and concentrated. The obtained residue was purified by column chromatography on silica gel (hexane:ethyl acetate=1:1) to give the title compound (442 mg) having the following physical data.

TLC: Rf 0.30 (hexane:ethyl acetate=1:2),

NMR (CDCl$_3$): δ 7.54–7.46 (m, 6H), 7.39 (d, J=8.4 Hz, 2H), 2.30 (t, J=7.2 Hz, 2H), 1.84 (m, 2H), 1.66–1.56 (m, 2H), 1.58 (s, 3H), 1.45–1.32 (m, 1H), 1.30–1.18 (m, 1H).

EXAMPLE 11

N-hydroxy-6-[4-(4-chlorophenyl)phenyl]-6-hydroxyheptanamide

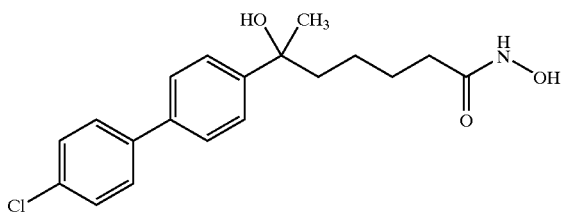

By the same procedure as a series of reactions of example 1→example 2 using the compound prepared in reference example 14, the compound of present invention having the following physical data was obtained.

TLC: Rf 0.27 (ethyl acetate),

NMR (d$_6$-DMSO): δ 10.24 (s, 1H), 8.60 (s, 1H), 7.67 (d, J=8.4 Hz, 2H), 7.58 (d, J=8.4 Hz, 2H), 7.49 (d, J=8.4 Hz, 2H), 7.48 (d, J=8.4 Hz, 2H), 4.87 (s, 1H), 1.85 (t, J=7.2 Hz, 2H), 1.74–1.60 (m, 2H), 1.44–1.34 (m, 2H), 1.30–1.20 (m, 1H), 1.05–0.93 (m, 1H).

EXAMPLE 11(1)

N-hydroxy-6-[4-(4-chlorophenyl)phenyl]-6-hydroxy-7-octenamide

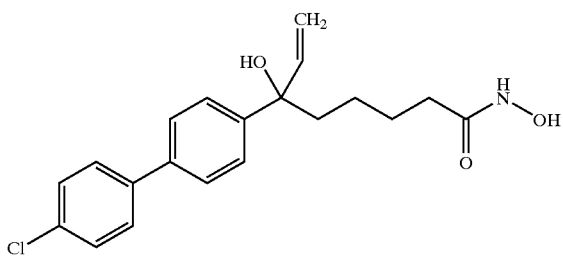

By the same procedure as a series of reactions of reference example 14→example 11 using vinylmagnesium bromide instead of methylmagnesium iodide, the compound of present invention having the following physical data was obtained.

TLC: Rf 0.28 (ethyl acetate),

NMR ($d_6$-DMSO): δ 10.26 (s, 1H), 8.62 (s, 1H), 7.67 (d, J=8.5 Hz, 2H), 7.59 (d, J=8.5 Hz, 2H), 7.48 (d, J=8.5 Hz, 4H), 6.12 (dd, J=17.2, 10.6 Hz, 1H), 5.21 (dd, J=17.2, 2.0 Hz, 1H), 5.15 (s, 1H), 5.00 (dd, J=10.6, 2.0 Hz, 1H), 1.84 (m, 2H), 1.83–1.72 (m, 2H), 1.42 (m, 2H), 1.32–1.22 (m, 1H), 1.12–1.00 (m, 1H).

EXAMPLE 11(2)

N-hydroxy-6-(4-biphenyl)-6-hydroxyheptanamide

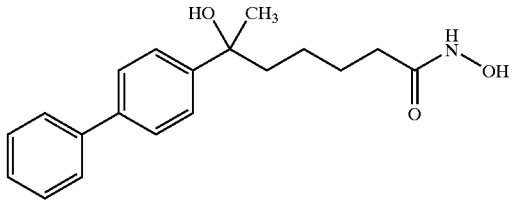

By the same procedure as a series of reactions of reference example 14→example 11 using 6-(4-biphenyl)-4-oxohexanoic acid instead of the compound prepared in reference example 13, the compound of present invention having the following physical data was obtained.

TLC: Rf 0.26 (ethyl acetate),

NMR ($d_6$-DMSO): δ 10.25 (s, 1H), 8.61 (s, 1H), 7.65–7.62 (m, 2H), 7.57 (d, J=8.4 Hz, 2H), 7.46 (d, J=8.4 Hz, 2H), 7.43–7.41 (m, 2H), 7.35–7.29 (m, 1H), 4.86 (s, 1H), 1.85 (t, J=7.2 Hz, 2H), 1.75–1.60 (m, 2H), 1.40 (s, 3H), 1.42–1.18 (m, 3H), 1.04–0.91 (m. 1H).

REFERENCE EXAMPLE 15

6-[4-(4-ethylphenyl)phenyl]-6-hydroxyheptanoic acid

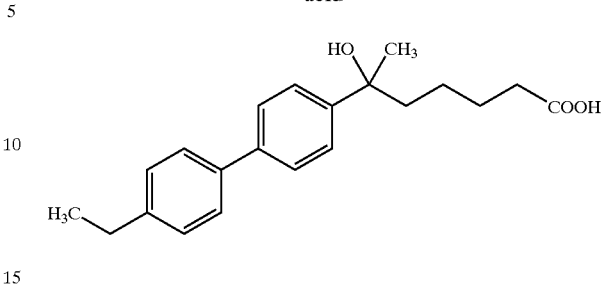

By the same procedure as a series of reactions of reference example 14 using 6-[4-(4-ethylphenyl)phenyl]-6-oxohexanoic acid instead of the compound prepared in reference example 13, enantiomer mixture of the title compound was obtained. By the following method, (+) isomer and (−) isomer of the title compound, respectively, were obtained from enantiomer mixture.

The enantiomer mixture (6.66 g), (1R,2R)-(+)-1,2-diphenylethylenediamine (4.33 g), ethyl acetate (80 mL) and hexane (20 mL) were mixed. The mixture was refluxed and dissolved completely. The mixture was cooled to room temperature and the crystal precipitated. The precipitated crystal was filtered and washed with a solution of hexane and ethyl acetate (hexane:ethyl acetate=1:1). The filtrate was concentrated. The obtained residue was used in the preparation of (−) isomer. The precipitated crystal was dissolved into ethyl acetate and washed with 1N hydrochloric acid, water and a saturated aqueous solution of sodium chloride and dried over anhydrous magnesium sulfate and concentrated to give (+) isomer of the title compound (2.44 g, 92.4% e.e, HPLC) having the following physical data.

The residue concentrated the filtrate was dissolved into ethyl acetate and washed with 1N hydrochloric acid, water and a saturated aqueous solution of sodium chloride, dried over anhydrous magnesium sulfate and concentrated. The obtained residue, (1S,2S)-(−)-1,2-diphenylethylenediamine (2.32 g), ethyl acetate (50 mL) and hexane (10 mL) were mixed. The mixture was refluxed and dissolved completely. The mixture was cooled to room temperature and crystal precipitated. The precipitated crystal was filtered and washed with a solution of hexane and ethyl acetate (hexane:ethyl acetate=1:1). The precipitated crystal was dissolved into ethyl acetate and washed with 1N hydrochloric acid, water and a saturated aqueous solution of sodium chloride, dried over anhydrous magnesium sulfate and concentrated to give (−) isomer of the title compound (2.88 g, 89.9% e.e, HPLC) having the following physical data.

(+) Isomer:

TLC: Rf 0.46 (chloroform:methanol=9:1), Retention time: 6.99 min. Column: DAICEL CHIRAL CELAD-RH, 4.6×150 mm; Eluant: acetonitrile:water=65:35; UV: 256 nm; Flow rate: 1.0 mL/min.

(−) Isomer: TLC: Rf 0.46 (chloroform:methanol=9:1), Retention time: 14.40 min. Column: DAICEL CHIRAL CELAD-RH, 4.6×150 mm; Eluant: acetonitrile:water= 65:35; UV: 256nm; Flow rate: 1.0 mL/min.

EXAMPLE 12

(+)-N-hydroxy-6-[4-(4-ethylphenyl)phenyl]-6-hydroxyheptanamide

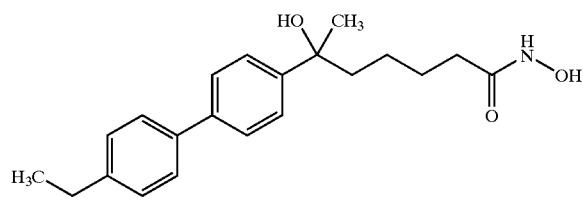

By the same procedure as a series of reactions of example 1→example 2 using (+) isomer of the compound prepared in reference example 15, the compound of the present invention having the following physical data was obtained.

$[\alpha]_D$: +14.74 (c 0.555, methanol),

TLC: Rf 0.35 (chloroform:methanol=9:1),

NMR ($d_6$-DMSO): δ 10.26 (s, 1H), 8.62 (s, 1H), 7.55 (d, J=8.4 Hz, 4H), 7.45 (d, J=8.4 Hz, 2H), 7.27 (d, J=8.4 Hz, 2H), 4.85 (s, 1H), 2.62 (q, J=7.4 Hz, 2H), 1.86 (t, J=7.4 Hz, 2H), 1.78–1.56 (m, 2H), 1.55–1.21 (m, 6H), 1.20 (t, J=7.4 Hz, 3H), 1.12–0.85 (m, 1H).

EXAMPLE 12(1)

(−)-N-hydroxy-6-[4-(4-ethylphenyl)phenyl]-6-hydroxyheptanamide

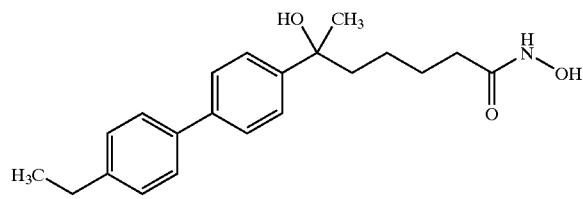

By the same procedure as a series of reactions of example 12 using (−) isomer of the compound prepared in reference example 15, the compound of the present invention having the following physical data was obtained.

$[\alpha]_D$: −12.18 (c 0.74, methanol),

TLC: Rf 0.35 (chloroform:methanol=9:1),

NMR ($d_6$-DMSO): δ 10.26 (s, 1H), 8.62 (s, 1H), 7.55 (d, J=8.4 Hz, 4H), 7.45 (d, J=8.4 Hz, 2H), 7.27 (d, J=8.4 Hz, 2H), 4.85 (s, 1H), 2.62 (q, J=7.4 Hz, 2H), 1.86 (t, J=7.4 Hz, 2H), 1.78–1.56 (m, 2H), 1.55–1.21 (m, 6H), 1.20 (t, J=7.4 Hz, 3H), 1.12–0.85 (m, 1H).

EXAMPLES 13(1)~13(44)

By the same procedure as a series of reactions of reference example 4→reference example 3→example 1→example 2 using a corresponding ketone derivative instead of the compound prepared in reference example 1, if desired, the conversion into the acid addition salts by conventional means, the following compounds of the present invention were obtained.

EXAMPLE 13(1)

(R)-(+)-N-hydroxy-6-(4-biphenyl)-6-hydroxyhexanamide

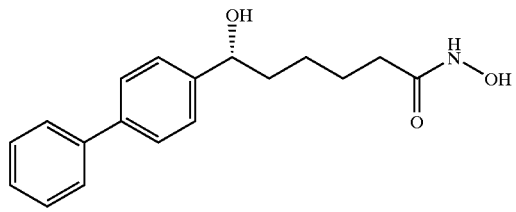

$[\alpha]_D$: +15.1 (c 0.245, methanol),

TLC: Rf 0.25 (chloroform:methanol:acetic acid=90:10:1),

NMR ($d_6$-DMSO): δ 10.29 (s. 1H), 8.63 (s, 1H), 7.65–7.57 (m, 4H), 7.46–7.30 (m, 5H), 5.13 (d, J=4.5 Hz, 1H), 4.54–4.49 (m, 1H), 1.91 (t, J=7.2 Hz, 2H), 1.64–1.44 (m, 4H), 1.40–1.22 (m, 2H).

EXAMPLE 13(2)

(R)-(+)-N-hydroxy-6-[4-(4-methylphenyl)phenyl]-6-hydroxyhexanamide

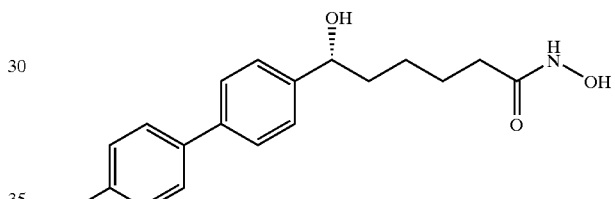

$[\alpha]_D$: +11.53 (c 0.215, methanol),

TLC: Rf 0.22 (chloroform:methanol:acetic acid=90:10:1),

NMR ($d_6$-DMSO): δ 10.29 (s, 1H), 8.62 (s, 1H), 7.56–7.51 (m, 4H), 7.34 (d, J=8.1 Hz, 2H), 7.24 (d, J=8.1 Hz, 2H), 5.11 (d, J=4.5 Hz, 1H), 4.52–4.48 (m, 1H), 2.32 (s, 3H), 1.90 (t, J=7.5 Hz, 2H), 1.62–1.15 (m, 6H).

EXAMPLE 13(3)

(R)-(+)-N-hydroxy-6-[4-(3-methylphenyl)phenyl]-6-hydroxyhexanamide

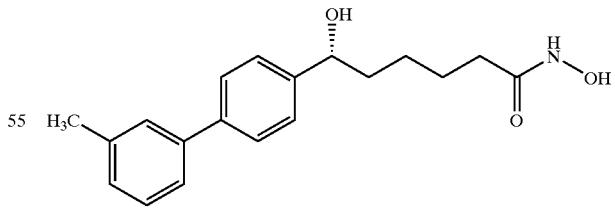

$[\alpha]_D$: +8.43 (c 0.37, methanol),

TLC: Rf 0.22 (chloroform:methanol:acetic acid=90:10:1),

NMR ($d_6$-DMSO): δ 10.29 (s, 1H), 8.63 (s, 1H), 7.56 (d, J=8.1 Hz, 2H), 7.44–7.29 (m, 5H), 7.14 (d, J=7.5 Hz, 1H), 5.12 (d, J=4.5 Hz, 1H), 4.59–4.48 (m, 1H), 2.35 (s, 3H), 1.90 (t, J=7.2 Hz, 2H), 1.63–1.12 (m, 6H).

EXAMPLE 13(4)

(R)-(+)-N-hydroxy-6-[4-(benzoxazol-2-yl)phenyl]-6-hydroxyhexanamide

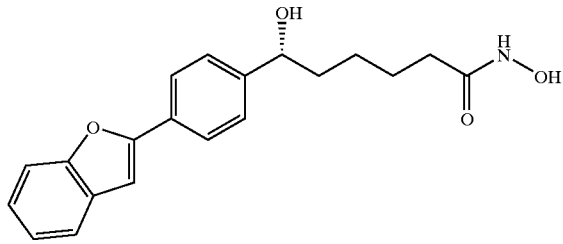

$[\alpha]_D$: +14.5 (c 0.195, methanol),

TLC: Rf 0.25 (chloroform:methanol:acetic acid 90:10:1),

NMR ($d_6$-DMSO): δ 10.28 (s, 1H), 8.62 (s, 1H), 7.84 (d, J=8.4 Hz, 2H), 7.65–7.58 (m, 2H), 7.42 (d, J=8.4 Hz, 2H), 7.37 (s, 1H), 7.33–7.19 (m, 2H), 5.19 (d, J=4.4 Hz, 1H), 4.59–4.45 (m, 1H), 1.89 (t, J=7.2 Hz, 2H), 1.62–1.05 (m, 6H).

EXAMPLE 13(5)

(R)-N-hydroxy-6-[4-(2-phenylethynyl)phenyl]-6-hydroxyhexanamide

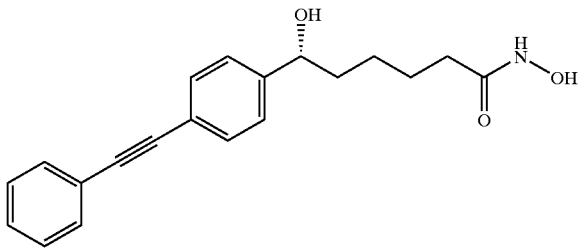

TLC: Rf 0.24 (chloroform:methanol=9:1),

NMR ($d_6$-DMSO): δ 10.28 (s, 1H), 8.62 (s, 1H), 7.55–7.32 (m, 9H), 5.20 (d, J=4.4 Hz, 1H), 4.56–4.44 (m, 1H), 1.89 (t, J=7.0 Hz, 2H), 1.60–1.08 (m, 6H).

EXAMPLE 13(6)

(R)-(+)-N-hydroxy-6-[4-(benzothiophen-2-yl)phenyl]-6-hydroxyhexanamide

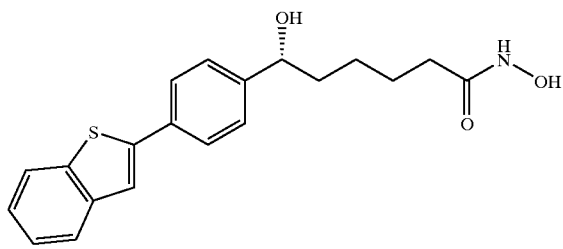

$[\alpha]_D$: +13.88 (c 0.085, methanol),

TLC: Rf 0.25 (chloroform:methanol:acetic acid=90:10:1),

NMR ($d_6$-DMSO): δ 10.28 (s, 1H), 8.62 (s, 1H), 7.96–7.92 (m, 1H), 7.84–7.79 (m, 2H), 7.70 (d, J=9.0 Hz, 2H), 7.39 (d, J=9.0 Hz, 2H), 7.36–7.28 (m, 2H), 5.18 (d, J=4.4 Hz, 1H), 4.59–4.48 (m, 1H), 1.89 (t, J=6.8 Hz, 2H), 1.65–1.10 (m, 6H).

EXAMPLE 13(7)

(R)-N-hydroxy-6-[4-(4-(cyanomethyl)phenyl)phenyl]-6-hydroxyhexanamide

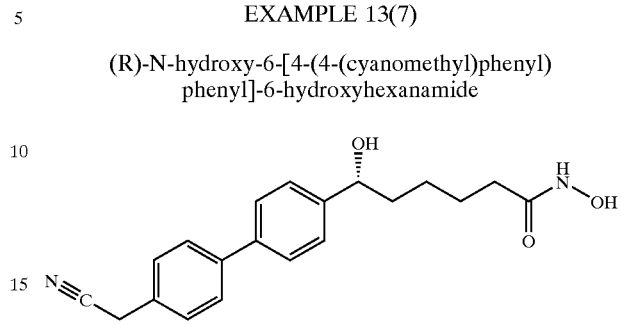

TLC: Rf 0.28 (ethyl acetate:methanol=9:1),

NMR ($d_6$-DMSO): δ 10.29 (s, 1H), 8.63 (s, 1H), 7.67 (d, J=8.1 Hz, 2H), 7.60 (d, J=8.1 Hz, 2H), 7.41 (d, J=8.1 Hz, 2H), 7.38 (d, J=8.1 Hz, 2H), 5 14 (d, J=4.5 Hz, 1H), 4.52 (m, 1H), 4.06 (s, 2H), 1.91 (t, J=7.2 Hz, 2H), 1.64–1.54 (m, 2H), 1.54–1.44 (m, 2H), 1.39–1.16 (m, 2H).

EXAMPLE 13(8)

(R)-N-hydroxy-6-[4-(4-ethylphenyl)phenyl]-6-hydroxyhexanamide

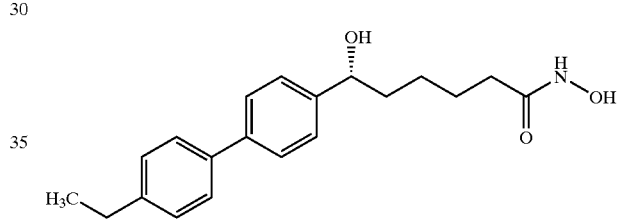

TLC: Rf 0.29 (chloroform:methanol=9:1),

NMR ($d_6$-DMSO): δ 10.42–10.20 (br, 1H), 8.75–8.55 (br, 1H), 7.56 (d, J=8.0 Hz, 2H), 7.55 (d, J=8.0 Hz, 2H), 7.36 (d, J=8.0 Hz, 2H), 7.27 (d, J=8.0 Hz, 2H), 5.12 (d, J=4.4 Hz, 1H), 4.58–4.45 (m, 1H), 2.62 (q, J=7.6 Hz, 2H), 1.91 (t, J=7.4 Hz, 2H), 1.70–1.10 (m, 6H), 1.19 (t, J=7.6 Hz, 3H).

EXAMPLE 13(9)

(R)-N-hydroxy-6-[4-(4-propylphenyl)phenyl]-6-hydroxyhexanamide

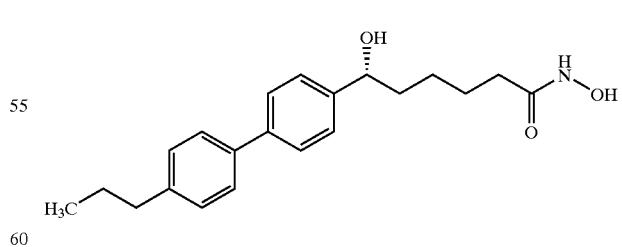

TLC: Rf 0.29 (chloroform:methanol=9:1),

NMR ($d_6$-DMSO): δ 10.30 (s, 1H), 8.64 (s, 1H), 7.57 (d, J=8.4 Hz, 2H), 7.54 (d, J=8.0 Hz, 2H), 7.36 (d, J=8.0 Hz, 2H), 7.25 (d, J=8.4 Hz, 2H), 5.12 (d, J=4.4 Hz, 1H), 4.58–4.44 (m, 1H), 2.57 (t, J=7.4 Hz, 2H), 1.92 (t, J=7.4 Hz, 2H), 1.72–1.10 (m, 8H), 0.90 (t, J=7.8 Hz, 3H).

EXAMPLE 13(10)

(R)-N-hydroxy-6-[4-(4-biphenyl)phenyl]-6-hydroxyhexanamide

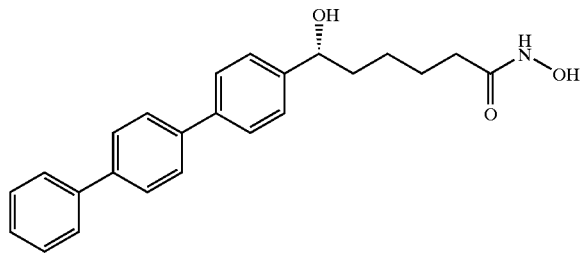

TLC: Rf 0.26 (chloroform:methanol=9:1),

NMR (d$_6$-DMSO): δ 10.30 (s, 1H), 8.64 (s, 1H), 7.78–7.60 (m, 8H), 7.54–7.30 (m, 5H), 5.15 (d, J=4.4 Hz, 1H), 4.59–4.46 (m, 1H), 1.91 (t, J=6.8 Hz, 2H), 1.65–1.10 (m, 6H).

EXAMPLE 13(11)

(R)-N-hydroxy-6-[4-(1-methylpiperidin-4-yl)phenyl]-6-hydroxyhexanamide hydrochloride

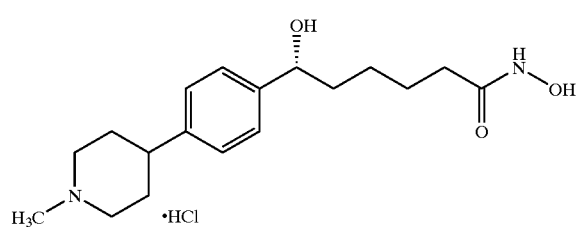

TLC: Rf 0.12 (methanol),

NMR (d$_6$-DMSO): δ 10.53 (br, 1H), 10.31 (s, 1H), 8.64 (br, 1H), 7.25 (d, J=8.2 Hz, 2H), 7.15 (d, J=8.2 Hz, 2H), 5.06 (br, 1H), 4.44 (t, J=6.0 Hz, 1H), 3.46–3.28 (m, 3H), 3.09–2.96 (m, 2H), 2.73 (d-like, J=4.2 Hz, 3H), 2.00–1.87 (m, 6H), 1.58–1.41 (m, 4H), 1.37–1.15 (m, 2H).

EXAMPLE 13(12)

(R)-N-hydroxy-6-[4-(indol-2-yl)phenyl]-6-hydroxyhexanamide

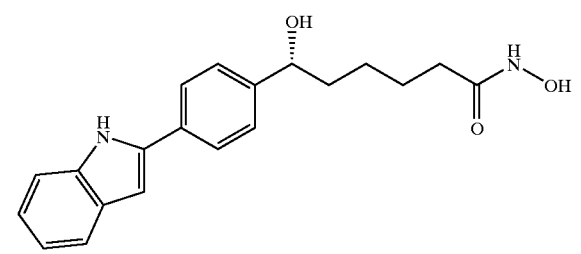

TLC: Rf 0.33 (chloroform:methanol:acetic acid=60:10:1),

NMR (d$_6$-DMSO): δ 11.42 (s, 1H), 10.25 (s, 1H), 8.62 (s, 1H), 7.76 (d, J=8.1 Hz, 2H), 7.47 (d, J=7.5 Hz, 1H), 7.40–7.30 (m, 3H), 7.10–7.00 (m, 1H), 7.00–6.90 (m, 1H), 6.81 (d, J=1.2 Hz, 1H), 5.12 (d, J=4.5 Hz, 1H), 4.55–4.42 (m, 1H), 1.88 (t, J=7.4 Hz, 2H), 1.70–1.40 (m, 4H), 1.40–1.10 (m, 2H).

EXAMPLE 13(13)

(R)-(+)-N-hydroxy-6-[4-(4-cyanophenyl)phenyl]-6-hydroxyhexanamide

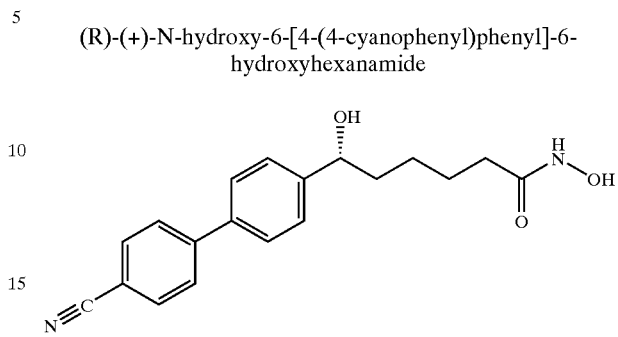

[α]$_D$: +4.60 (c 0.265, methanol),

TLC: Rf 0.34 (ethyl acetate:methanol=19:1),

NMR (d$_6$-DMSO): δ 10.28 (brs, 1H), 8.63 (s, 1H), 7.90 (d, J=9.0 Hz, 2H), 7.85 (d, J=9.0 Hz, 2H), 7.68 (d, J=8.1 Hz, 2H), 7.42 (d, J=8.1 Hz, 2H), 5.19 (d, J=4.8 Hz, 1H), 4.58–4.51 (m, 1H), 1.90 (t, J=7.2 Hz, 2H), 1.59–1.14 (m, 6H).

EXAMPLE 13(14)

(R)-(+)-N-hydroxy-6-[4-phenyl-2-methylphenyl]-6-hydroxyhexanamide

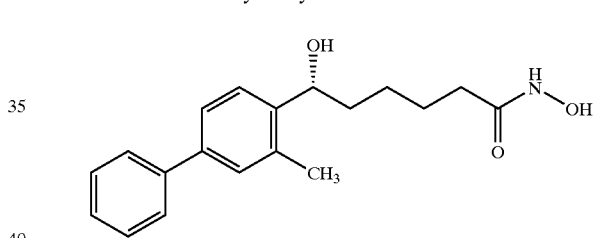

[α]$_D$: +18.31 (c 0.225, methanol),

TLC: Rf 0.37 (ethyl acetate:methanol=19:1),

NMR (d$_6$-DMSO): δ 10.30 (s, 1H), 8.64 (s, 1H), 7.63–7.60 (m, 2H), 7.46–7.39 (m, 5H), 7.34–7.28 (m, 1H), 5.02 (d, J=4.5 Hz, 1H), 4.72–4.68 (m, 1H), 2.32 (s, 3H), 1.92 (t, J=6.9 Hz, 2H), 1.60–1.22 (m, 6H).

EXAMPLE 13(15)

(R)-N-hydroxy-6-(4-cycloheptylphenyl)-6-hydroxyhexanamide

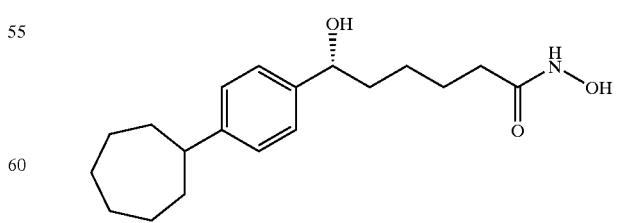

TLC: Rf 0.43 (ethyl acetate:methanol=9:1),

NMR (d$_6$-DMSO): δ 10.28 (s, 1H), 8.63 (s, 1H), 7.17 (d, J=8.3 Hz, 2H), 7.10 (d, J=8.3 Hz, 2H), 4.98 (d, J=4.5 Hz,

1H), 4.41 (m, 1H), 2.61 (m, 1H), 1.89 (t, J=7.2 Hz, 2H), 1.81–1.41 (m, 16H), 1.37–1.10 (m, 2H).

EXAMPLE 13(16)

(R)-N-hydroxy-6-(9,10-dihydrophenanthren-2-yl)-6-hydroxyhexanamide

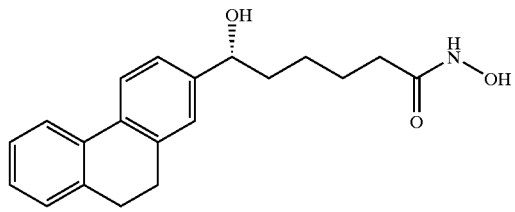

TLC: Rf 0.37 (ethyl acetate:methanol=9:1),

NMR (d$_6$-DMSO): δ 10.30 (s, 1H), 8.63 (s, 1H), 7.77 (d, J=7.2 Hz, 1H), 7.73 (d, J=8.1 Hz, 1H), 7.31–7.17 (m, 5H), 5.10 (d, J=4.5 Hz, 1H), 4.47 (m, 1H), 2.79 (s, 4H), 1.91 (t, J=7.2 Hz, 2H), 1.63–1.44 (m, 4H), 1.41–1.17 (m, 2H).

EXAMPLE 13(17)

(R)-N-hydroxy-6-[4-(1-ethoxycarbonylpiperidin-4-yl)phenyl]-6-hydroxyhexanamide

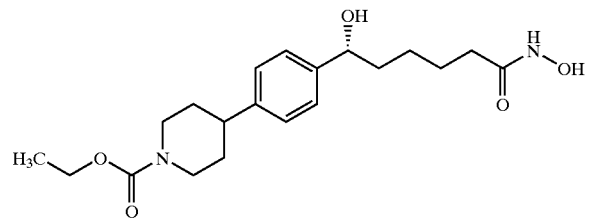

TLC: Rf 0.42 (ethyl acetate:methanol=9:1),

NMR (d$_6$-DMSO): δ 10.29 (s, 1H), 8.63 (s, 1H), 7.21 (d, J=8.3 Hz, 2H), 7.15 (d, J=8.3 Hz, 2H), 5.01 (d, J=4.2 Hz, 1H), 4.42 (m, 1H), 4.11–4.01 (m, 2H), 4.01 (q, J=7.0 Hz, 2H), 2.83 (m, 2H), 2.65 (m, 1H), 1.89 (t, J=7.2 Hz, 2H), 1.75–1.71 (m, 2H), 1.55–1.42 (m, 6H), 1.37–1.25 (m, 2H), 1.18 (t, J=7.0 Hz, 3H).

EXAMPLE 13(18)

(R)-(+)-N-hydroxy-[4-(4-(N-methylcarbamoyl)phenyl)phenyl]-6-hydroxyhexanamide

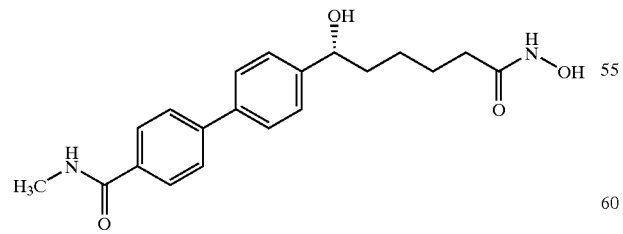

[α]$_D$: +12.37 (c 0.08, methanol),
TLC: Rf 0.33 (chloroform:methanol=9:1),
NMR (d$_6$-DMSO): δ 10.29 (s, 1H), 8.63 (brs, 1H), 8.48–8.43 (m, 1H), 7.89 (d, J=8.4 Hz, 2H), 7.73 (d, J=8.4 Hz, 2H), 7.65 (d, J=85.4 Hz, 2H), 7.39 (d, J=8.4 Hz, 2H), 5.18 (brs, 1H), 4.56–4.50 (m, 1H), 2.78 (d, J=4.8 Hz, 3H), 1.90 (t, J=7.5 Hz, 2H), 1.63–1.11 (m, 6H).

EXAMPLE 13(19)

(R)-(+)-N-hydroxy-6-(4-cyclohexylphenyl)-6-hydroxyhexanamide

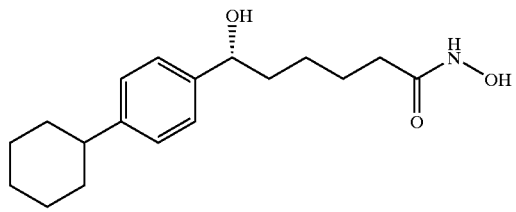

[α]$_D$: +12.65 (c 0.16, methanol),

TLC: Rf 0.31 (chloroform:methanol=19:1),

NMR (d$_6$-DMSO): δ 10.27 (s, 1H), 8.62 (s, 1H), 7.18 (d, J=8.1 Hz, 2H), 7.12 (d, J=8.1 Hz, 2H), 4.98 (d, J=4.2 Hz, 1H), 4.42–4.36 (m, 1H), 2.45–2.39 (m, 1H), 1.89 (t, J=7.2 Hz, 2H), 1.80–1.09 (m, 17H).

EXAMPLE 13(20)

(R)-N-hydroxy-6-[4-(5-hydroxybenzofuran-2-yl)phenyl]-6-hydroxyhexanamide

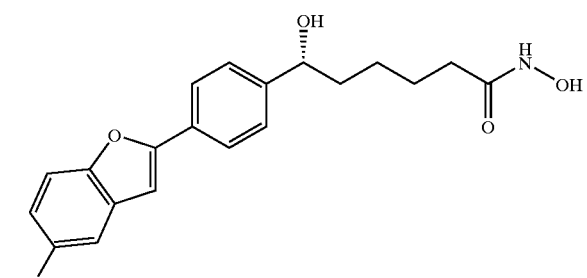

TLC: Rf 0.27 (chloroform:methanol:acetic acid=60:10:1),

NMR (d$_6$-DMSO): δ 10.25 (s, 1H), 9.18 (s, 1H), 8.60 (s, 1H), 7.77 (d, J=8.2 Hz, 2H), 7.38 (d, J=8.2 Hz, 2H), 7.35 (d, J=8.8 Hz, 1H), 7.19 (s, 1H), 6.89 (d, J=2.6 Hz, 1H), 6.69 (dd, J=8.8, 2.6 Hz, 1H), 5.17 (d, J=4.4 Hz, 1H), 4.60–4.40 (m, 1H), 1.88 (t, J=7.1 Hz, 2H), 1.70–1.10 (m, 6H).

EXAMPLE 13(21)

(R)-N-hydroxy-6-[4-(2-(4-methylphenyl)ethynyl)phenyl]-6-hydroxyhexanamide

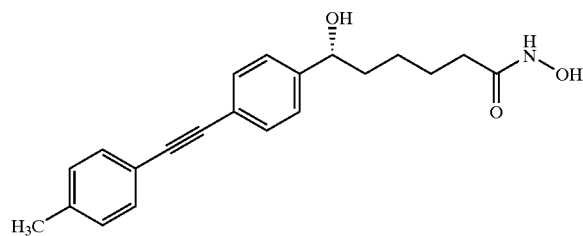

TLC: Rf 0.41 (chloroform:methanol:acetic acid=60:10:1),

NMR ($d_6$-DMSO): δ 10.27 (s, 1H), 8.65 (s, 1H), 7.50–7.35 (m, 4H), 7.31 (d, J=8.0 Hz, 2H), 7.20 (d, J=8.0 Hz, 2H), 5.18 (d, J=4.4 Hz, 1H), 4.60–4.40 (m, 1H), 2.30 (s, 3H), 1.87 (t, J=7.1 Hz, 2H), 1.65–1.00 (m, 6H).

EXAMPLE 13(22)

(R)-N-hydroxy-6-[4-((1E)-2-(4-methylphenyl)vinyl)phenyl]-6-hydroxyhexanamide

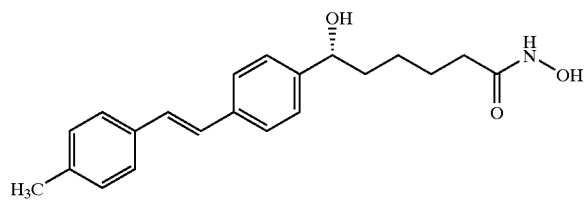

TLC: Rf 0.43 (chloroform:methanol:acetic acid 60:10:1),

NMR ($d_6$-DMSO): δ 10.28 (s, 1H), 7.53–7.38 (m, 4H), 7.26 (d, J=8.0 Hz, 2H), 7.20–7.05 (m, 4H), 4.45 (t, J=6.4 Hz, 1H), 2.25 (s, 3H), 1.87 (t, J=7.0 Hz, 2H), 1.70–1.00 (m, 6H).

EXAMPLE 13(23)

(R)-N-hydroxy-6-[4-(4-trifuoromethoxyphenyl)phenyl]-6-hydroxyhexanamide

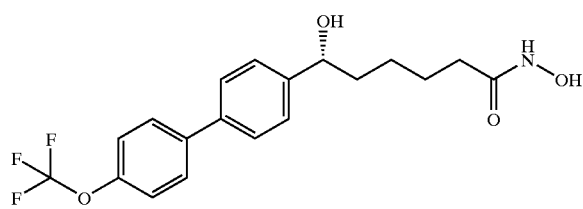

TLC: Rf 0.25 (chloroform:methanol=9:1),

NMR ($d_6$-DMSO): δ 10.29 (s, 1H), 8.63 (s, 1H), 7.76 (d, J=8.7 Hz, 2H), 7.61 (d, J=8.7 Hz, 2H), 7.43–7.38 (m, 4H), 5.15 (d, J=4.5 Hz, 1H), 4.55–4.95 (m, 1H), 1.90 (t, J=7.5 Hz, 2H), 1.63–1.12 (m, 6H).

EXAMPLE 13(24)

(R)-N-hydroxy-6-[4-(4-ethylthiophenyl)phenyl]-6-hydroxyhexanamide

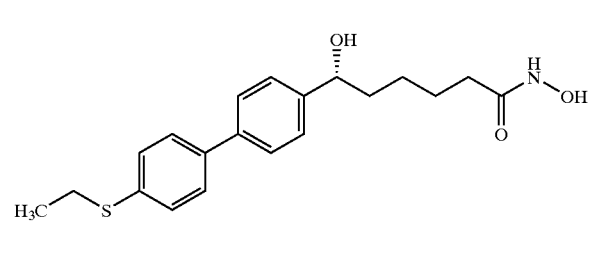

TLC: Rf 0.40 (ethyl acetate:methanol=4:1),

NMR ($d_6$-DMSO): δ 10.29 (s, 1H), 8.63 (s, 1H), 7.59 (d, J=8.4 Hz, 2H), 7.58 (d, J=8.4 Hz, 2H), 7.37 (d, J=8.4 Hz, 4H), 5.13 (br, 1H), 4.51 (t, J=6.0 Hz, 1H), 3.00 (q, J=7.2 Hz, 2H), 1.91 (t, J=7.0 Hz, 2H), 1.58 (m, 2H), 1.48 (m, 2H), 1.39–1.16 (m, 2H), 1.24 (t, J=7.2 Hz, 3H).

EXAMPLE 13(25)

(R)-N-hydroxy-6-[4-(4-methoxyphenyl)phenyl]-6-hydroxyhexanamide

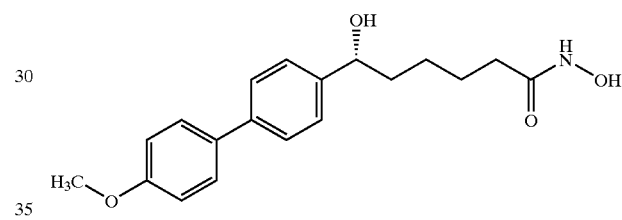

TLC: Rf 0.23 (ethyl acetate:methanol=4:1),

NMR ($d_6$-DMSO): δ 10.29 (s, 1H), 8.64 (s, 1H), 7.57 (d, J=8.5 Hz, 2H), 7.53 (d, J=8.5 Hz, 2H), 7.34 (d, J=8.5 Hz, 2H), 6.99 (d, J=8.5 Hz, 2H), 5.11 (d, J=4.2 Hz, 1H), 4.50 (m, 1H), 3.77 (s, 3H), 1.91 (t, J=7.2 Hz, 2H), 1.57 (m, 2H), 1.48 (m, 2H), 1.39–1.16 (m, 2H).

EXAMPLE 13(26)

(R)-N-hydroxy-6-[4-(4-(1-methylethyl)phenyl)phenyl]-6-hydroxyhexanamide

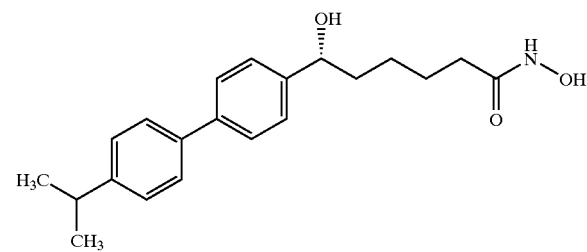

TLC: Rf 0.20 (chloroform:methanol=9:1),

NMR ($d_6$-DMSO): δ 10.29 (s, 1H), 8.63 (brs, 1H), 7.55 (d, J=8.4 Hz, 2H), 7.54 (d, J=8.4 Hz, 2H), 7.35 (d, J=8.4 Hz, 2H), 7.30 (d, J=8.4 Hz, 2H), 5.11 (brs, 1H), 4.50 (t, J=6.0 Hz, 1H), 2.98–2.82 (m, 1H), 1.90 (t, J=7.2 Hz, 2H), 1.62–1.20 (m, 6H), 1.21 (d, J=6.9 Hz, 6H).

EXAMPLE 13(27)

(R)-N-hydroxy-6-[4-(4-(N,N-dimethylcarbamoylmethyl)phenyl)phenyl]-6-hydroxyhexanamide

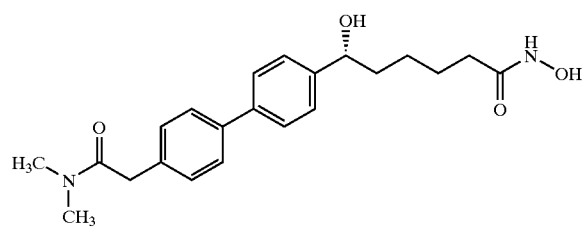

TLC: Rf 0.21 (chloroform:methanol 9:1),

NMR (d$_6$-DMSO): δ 10.30 (s, 1H), 8.64 (s, 1H), 7.57 (d, J=8.0 Hz, 4H), 7.37 (d, J=8.0 Hz, 2H), 7.28 (d, J=8.0 Hz, 2H), 5.13 (d, J=4.4 Hz, 1H), 4.59–4.46 (m, 1H), 3.71 (s, 2H), 3.01 (s, 3H), 2.83 (s, 3H), 1.91 (t, J=7.0 Hz, 2H), 1.65–1.10 (m, 6H).

EXAMPLE 13(28)

(R)-N-hydroxy-6-[4-benzothiazol-2-yl)phenyl]-6-hydroxyhexanamide

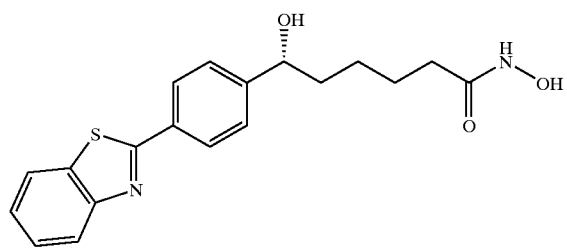

TLC: Rf 0.24 (chloroform:methanol=9:1),

NMR (d$_6$-DMSO): δ 10.30 (s, 1H), 8.64 (s, 1H), 8.18–8.12 (m, 1H), 8.09–7.98 (m, 3H), 7.60–7.40 (m, 4H), 5.38–5.22 (m, 1H), 4.65–4.55 (m, 1H), 1.92 (t, J=7.4 Hz, 2H), 1.70–1.15 (m, 6H).

EXAMPLE 13(29)

(R)-N-hydroxy-6-[4-(4-(methoxymethoxymethyl)phenyl)phenyl]-6-hydroxyhexanamide

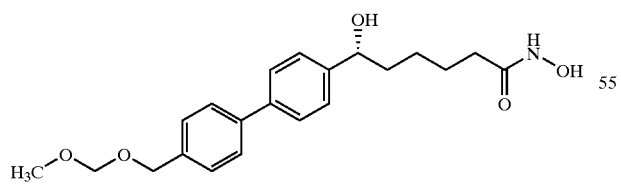

TLC: Rf 0.30 (chloroform:methanol=9:1),

NMR (d$_6$-DMSO): δ 10.30 (s, 1H), 8.64 (s, 1H), 7.63 (d, J=8.0 Hz, 2H), 7.59 (d, J=8.0 Hz, 2H), 7.40 (d, J=8.0 Hz, 2H), 7.38 (d, J=8.0 Hz, 2H), 5.14 (d, J=4.4 Hz, 1H, 4.66 (s, 2H), 4.60–4.45 (m, 3H), 3.31 (s, 3H), 1.92 (t, J=7.0 Hz, 2H), 1.70–1.12 (m, 6H).

EXAMPLE 13(30)

(R)-(+N-hydroxy-6-[4-(6-methoxybenzoxazol-2-yl)phenyl]-6-hydroxyhexanamide

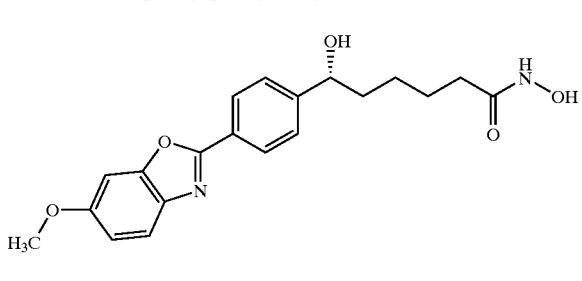

[α]$_D$: +7.31 (c 0.19, methanol),

TLC: Rf 0.15 (chloroform:methanol=9:1),

NMR (d$_6$-DMSO): δ 10.29 (s, 1H), 8.63 (brs, 1H), 8.07 (d, J=8.7 Hz, 2H), 7.66 (d, J=8.7 Hz, 1H), 7.52 (d, J=8.7 Hz, 2H), 7.40 (d, J=2.4 Hz, 1H), 6.99 (dd, J=8.7 Hz, 2.4 Hz, 1H), 5.29 (brs, 1H), 4.60–4.56 (m, 1H), 3.83 (s, 3H), 1.90 (t, J=7.5 Hz, 2H), 1.63–1.20 (m, 6H).

EXAMPLE 13(31)

(R)-N-hydroxy-6-[4-(6-methylbenzoxazol-2-yl)phenyl]-6-hydroxyhexanamide

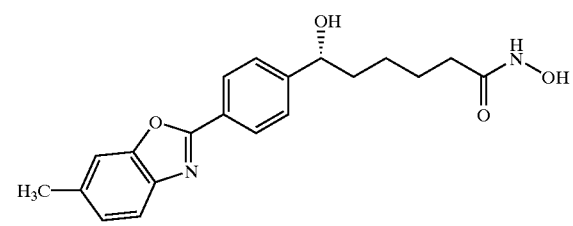

TLC: Rf 0.28 (chloroform:methanol=9:1),

NMR (d$_6$-DMSO): δ 10.30 (s, 1H), 8.90–8.30 (br, 1H), 8.11 (d, J=8.4 Hz, 2H), 7.65 (d, J=8.2 Hz, 1H), 7.59 (d, J=1.0 Hz, 1H), 7.53 (d, J=8.4 Hz, 2H), 7.21 (dd, J=8.2,1.0 Hz, 1H), 5.60–4.90 (br, 1H), 4.60 (t, J=6.2 Hz, 1H), 2.46 (s, 3H), 1.91 (t, J=7.4 Hz, 2H), 1.68–1.12 (m, 6H).

EXAMPLE 13(32)

(R)-N-hydroxy-6-[4-(4-methoxymethylphenyl)phenyl]-6-hydroxyhexanamide

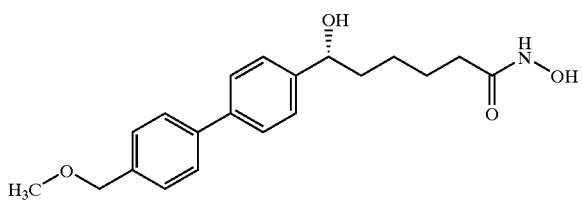

TLC: Rf 0.39 (chloroform:methanol=9:1),

NMR (d$_6$-DMSO): δ 10.31 (s, 1H), 9.10–8.10 (br, 1H), 7.62 (d, J=8.4 Hz, 2H), 7.59 (d, J=8.4 Hz, 2H), 7.38 (d, J=8.4 Hz, 4H), 5.50–4.70 (br, 1H), 4.52 (t, J=6.2 Hz, 1H), 4.43 (s, 2H), 3.30 (s, 3H), 1.91 (t, J=7.4 Hz, 2H), 1.70–1.10 (m, 6H).

EXAMPLE 13(33)

(R)-N-hydroxy-6-[4-(5-methoxybenzoxazol-2-yl)phenyl]-6-hydroxyhexanamide

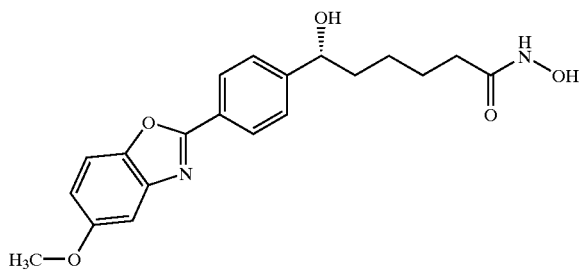

TLC: Rf 0.13 (chloroform:methanol:acetic acid=90:10:1),

NMR (d$_6$-DMSO): δ 10.25 (s, 1H), 8.62 (s, 1H), 8.08 (d, J=8.3 Hz, 2H), 7.63 (d, J=9.0 Hz, 1H), 7.50 (d, J=8.3 Hz, 2H), 7.31 (d, J=2.4 Hz, 1H), 6.96 (dd, J=9.0, 2.4 Hz, 1H), 5.29 (d, J=4.5 Hz, 1H), 4.62–4.52 (m, 1H), 3.79 (s, 3H), 1.88 (t, J=7.2 Hz, 2H), 1.65–1.10 (m, 6H).

EXAMPLE 13(34)

(R)-N-hydroxy-6-[4-(4-methoxybenzoxazol-2-yl)phenyl]-6-hydroxyhexanamide

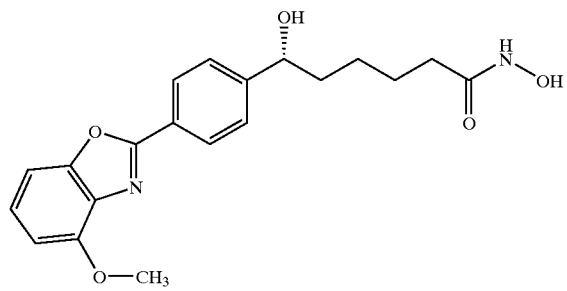

TLC: Rf 0.28 (chloroform:methanol=9:1),

NMR (d$_6$-DMSO): δ 10.32 (s, 1H), 8.64 (s, 1H), 8.12 (d, J=8.4 Hz, 2H), 7.53 (d, J=8.4 Hz, 2H), 7.40–7.28 (m, 2H), 7.02–6.90 (m, 1H), 5.31 (d, J=4.4 Hz, 1H), 4.66–4.54 (m, 1H), 3.99 (s, 3H), 1.92 (t, J=7.4 Hz, 2H), 1.70–1.10 (m, 6H).

EXAMPLE 13(35)

(R)-(+)-N-hydroxy-6-[4-(4-(piperidin-1-ylmethyl)phenyl)phenyl]-6-hydroxyhexanamide.hydrochloride

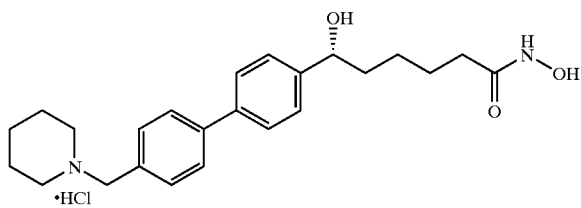

[α]$_D$: +6.17 (c 0.1 2, methanol),

TLC: Rf 0.21 (chloroform:methanol=4:1),

NMR (d$_6$-DMSO): δ 10.41–10.31 (m, 2H), 7.73 (d, J=8.1 Hz, 2H), 7.65–7.61 (m, 4H), 7.39 (d, J=8.1 Hz, 2H), 4.52 (t, J=6.3 Hz, 1H), 4.26 (d, J=5.1 Hz, 2H), 3.32–3.27 (m, 2H), 2.91–2.78 (m, 2H), 1.90 (t, J=7.2 Hz, 2H).

EXAMPLE 13(36)

(R)-(+)-N-hydroxy-6-[4-(4-hydroxybenzoxazol-2-yl)phenyl]-6-hydroxyhexanamide

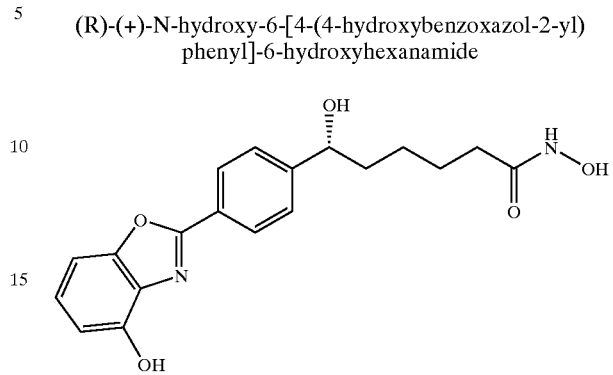

[α]$_D$: +6.33 (c 0.12, methanol),

TLC: Rf 0.42 (chloroform:methanol=17:3),

NMR (d$_6$-DMSO): δ 10.35 (s, 1H), 10.30 (s, 1H), 8.63 (s, 1H), 8.10 (d, J=8.1 Hz, 2H), 7.52 (d, J=8.1 Hz, 2H), 7.21–7.14 (m, 2H), 6.78–6.75 (m, 1H), 5.30 (d, J=4.5 Hz, 1H), 4.62–4.54 (m, 1H), 1.91 (t, J=7.2 Hz, 2H), 1.62–1.16 (m, 6H).

EXAMPLE 13(37)

(R)-N-hydroxy-6-[4-(6-hydroxybenzoxazol-2-yl)phenyl]-6-hydroxylhexanamide

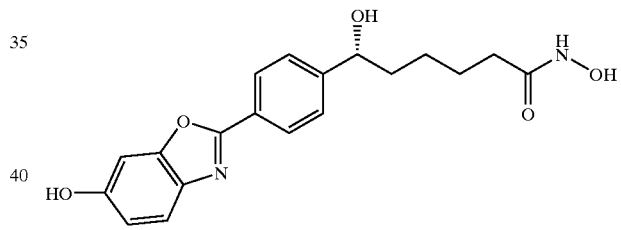

TLC: Rf 0.21 (chloroform:methanol:acetic acid=60:10:1),

NMR (d$_6$-DMSO): δ 10.25 (s, 1H), 9.80 (s, 1H), 8.60 (s, 1H), 8.03 (d, J=8.2 Hz, 2H), 7.56–7.42 (m, 3H), 7.05 (d, J=2.2 Hz, 1H), 6.81 (dd, J=8.4, 2.2 Hz, 1H), 5.25 (d, J=4.4 Hz, 1H), 4.62–4.50 (m, 1H), 1.88 (t, J=7.4 Hz, 2H), 1.70–1.10 (m, 6H).

EXAMPLE 13(38)

(R)-N-hydroxy-6-[4-((1E)-2-(4-methylthiophenyl)vinyl)phenyl]-6-hydroxyhexanamide

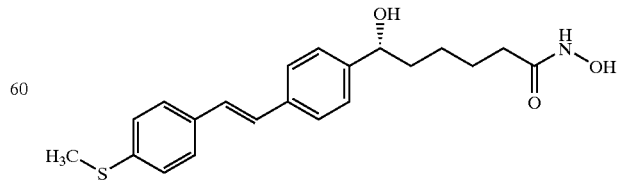

TLC: Rf 0.22 (chloroform:methanol:acetic acid=90:10:1),

NMR (d$_6$-DMSO): δ 10.25 (s, 1H), 7.50 (d, J=8.4 Hz, 2H), 7.49 (d, J=9.0 Hz, 2H), 7.30–7.05 (m, 6H), 4.45 (t, J=6.1 Hz, 1H), 2.45 (s, 3H), 1.87 (t, J=7.2 Hz, 2H), 1.65–1.00 (m, 6H).

EXAMPLE 13(39)

(R)-N-hydroxy-6-[4-(5-methoxybenzofuran-2-yl)phenyl]-6-hydroxyhexanamide

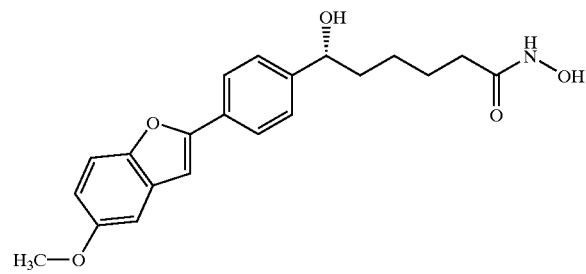

TLC: Rf 0.27 (chloroform:methanol 9:1),

NMR (d$_6$-DMSO): δ 10.30 (s, 1H), 8.64 (s, 1H), 7.83 (d, J=8.4 Hz, 2H), 7.50 (d, 8.8 Hz, 1H), 7.42 (d, J=8.4 Hz, 2H), 7.30 (s, 1H), 7.14 (d, J=2.6 Hz, 1H), 6.88 (dd, J=8.8, 2.6 Hz, 1H), 5.21 (d, J=4.4 Hz, 1H), 4.60–4.48 (m, 1H), 3.79 (s, 3H), 1.91 (t, J=7.0 Hz, 2H), 1.68–1.14 (m, 6H).

EXAMPLE 13(40)

(R)-N-hydroxy-6-[4-(5-methylthiobenzofuran-2-yl)phenyl]-6-hydroxyhexanamide

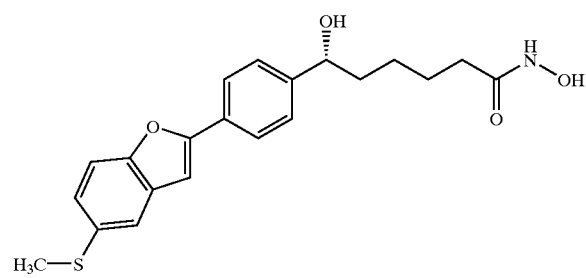

TLC: Rf 0.27 (chloroform:methanol=9:1),

NMR (d$_6$-DMSO): δ 10.30 (s, 1H), 8.82–8.42 (br, 1H), 7.84 (d, J=8.4 Hz, 2H), 7.60–7.52 (m, 2H), 7.43 (d, J=8.4 Hz, 2H), 7.31 (s, 1H), 7.23 (dd, J=8.8, 2.0 Hz, 1H), 5.42–4.96 (br, 1H), 4.54 (t, J=6.4 Hz, 1H), 2.51 (s, 3H), 1.92 (t, J=7.0 Hz, 2H), 1.70–1.12 (m, 6H).

EXAMPLE 13(41)

(R)-(+)-N-hydroxy-6-[4-(4-(2-(dimethylamino)ethyl)phenyl)phenyl]-6-hydroxyhexanamide.hydrochloride

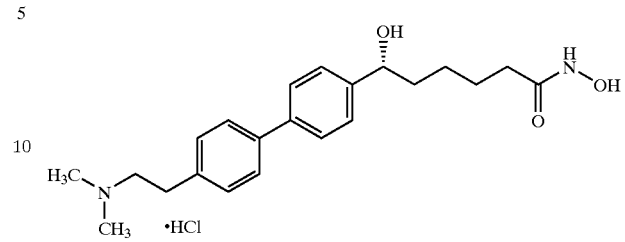

[α]$_D$: +22.11 (c 0.635, dimethylformamide),
TLC: Rf 0.12 (chloroform:methanol=7:3), NMR (d$_6$-DMSO): δ 10.60 (s, 1H), 10.32 (s, 1H), 8.62 (s, 1H), 7.62 (d, J=8.4 Hz, 2H), 7.57 (d, J=8.4 Hz, 2H), 7.38–7.33 (m, 4H), 5.14 (d, J=4.2 Hz, 1H), 4.54–4.48 (m, 1H), 3.30–3.25 (m, 2H), 3.06–3.00 (m, 2H), 2.78 (s, 6H), 1.91 (t, J=7.2 Hz, 2H), 1.62–1.15 (m, 6H).

EXAMPLE 13(42)

(R)-(+)-N-hydroxy-6-[4-(4-(2-(dimethylamino)ethoxy)phenyl)phenyl]-6-hydroxyhexanamide.hydrochloride

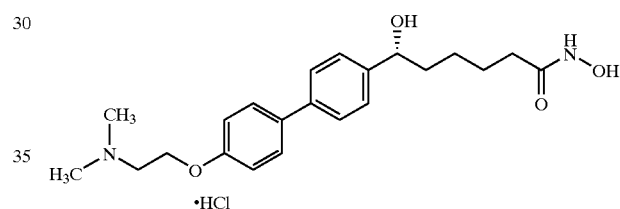

[α]$_D$: +20.47 (c 1.005, dimethylformamide),
TLC: Rf 0.32 (chloroform:methanol=4:1), NMR (d$_6$-DMSO): δ 10.56 (br, 1H), 10.32 (s, 1H), 8.63 (s, 1H), 7.61 (d, J=8.5 Hz, 2H), 7.54 (d, J=8.5 Hz, 2H), 7.35 (d, J=8.5 Hz, 2H), 7.07 (d, J=8.5 Hz, 2H), 5.12 (d, J=4.2 Hz, 1H), 4.05 (m, 1H), 4.39 (t, J=5.0 Hz, 2H), 3.50 (t, J=5.0 Hz, 2H), 2.83 (s, 6H), 1.91 (t, J=7.2 Hz, 2H), 1.57 (m, 2H), 1.50 (m, 2H), 1.39–1.17 (m, 2H).

EXAMPLE 13(43)

(R)-(+)-N-hydroxy-6-[4-(4-(2-(diethylamino)ethyl)phenyl)phenyl]-6-hydroxyhexanamide.hydrochloride

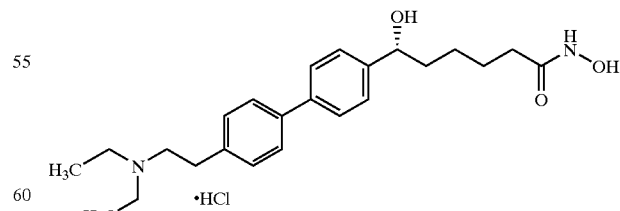

[α]$_D$: +18.58 (c 0.93, dimethylformamide),
TLC: Rf 0.25 (chloroform:methanol=9:1), NMR (d$_6$-DMSO): δ 10.47 (brs, 1H), 10.32 (s, 1H), 8.62 (brs, 1H), 7.61 (d, J=8.4 Hz, 2H), 7.58 (d, J=8.4 Hz, 2H), 7.37 (d, J=8.4 Hz, 2H), 7.37 (d, J=8.4 Hz, 2H), 5.13 (brs, 1H), 4.53–4.49 (m, 1H), 3.31–3.01 (m, 8H), 1.90 (t, J=6.9 Hz, 2H), 1.62–1.15 (m, 6H), 1.23 (t, J=6.9 Hz, 6H).

EXAMPLE 13(44)

(R)-N-hydroxy-6-[4-(4-(2-hydroxyethyl)phenyl)phenyl]-6-hydroxyhexanamide

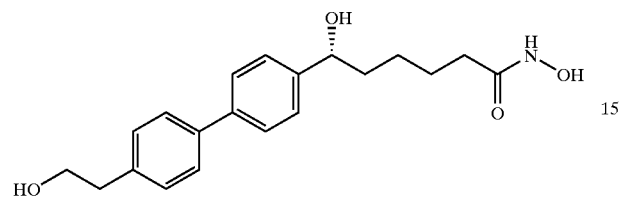

TLC: Rf 0.28 (chloroform:methanol=9:1),

NMR (d$_6$-DMSO): δ 10.29 (s, 1H), 8.63 (s, 1H), 7.56 (d, J=8.1 Hz, 2H), 7.53 (d, J=8.1 Hz, 2H), 7.36 (d, J=8.1 Hz, 2H), 7.27 (d, J=8.1 Hz, 2H), 5.12 (d, J=4.5 Hz, 1H), 4.64 (t, J=5.3 Hz, 1H), 4.51 (m, 1H), 3.61 (m, 2H), 2.74 (t, J=7.0 Hz, 2H), 1.91 (t, J=7.0 Hz, 2H), 1.63–1.43 (m, 4H), 1.40–1.15 (m, 2H).

EXAMPLES 14(1)–14(5)

By the same procedure as a series of reactions of reference example 5→reference example 3→example 1→example 2 using a corresponding ketone derivative instead of the compound prepared in reference example 1, if desired, the conversion into the acid addition salts by conventional means., the following compounds of the present invention were obtained.

EXAMPLE 14(1)

(S)-(–)-N-hydroxy-6-[4-(4-methylthiophenyl)phenyl]-6-hydroxyhexanamide

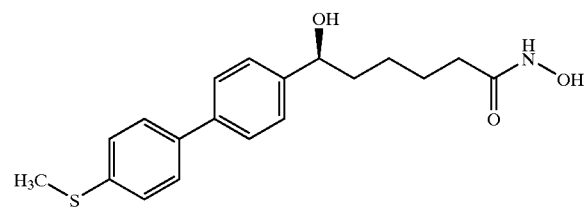

[α]$_D$: –26.3 (c 0.99, dimethylformamide),

TLC: Rf 0.21 (chloroform:methanol=9:1),

NMR (d$_6$-DMSO): δ 10.29 (s, 1H), 8.63 (s, 1H), 7.60 (d, J=8.4 Hz, 2H), 7.58 (d, J=8.4 Hz, 2H), 7.37 (d, J=8.4 Hz, 2H), 7.32 (d, J=8.4 Hz, 2H), 5.12 (d, J=3.9 Hz, 1H), 4.51 (m, 1H), 2.50 (s, 3H), 1.91 (t, J=7.5 Hz, 2H), 1.65–1.15 (m, 6H).

EXAMPLE 14(2)

(S)-(–)-N-hydroxy-6-[4-(2-(4-methylthiophenyl)ethynyl)phenyl]-6-hydroxyhexanamide

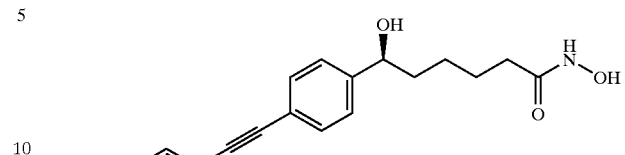

[α]$_D$: –33.4 (c 0.99, dimethylformamide),

TLC: Rf 0.19 (chloroform:methanol=9:1),

NMR (d$_6$-DMSO): δ 10.28 (s, 1H), 8.62 (s, 1H), 7.47 (d, J=8.4 Hz, 2H), 7.45 (d, J=8.4 Hz, 2H), 7.33 (d, J=8.4 Hz, 2H), 7.27 (d, J=8.4 Hz, 2H), 5.20 (d, J=4.8 Hz, 1H), 4.51 (m, 1H), 2.49 (s, 3H), 1.90 (t, J=7.2 Hz, 2H), 1.60–1.40 (m, 4H), 1.35–1.15 (m, 2H).

EXAMPLE 14(3)

(S)-(–)-N-hydroxy-6-[4-(benzoxazol-2-yl)phenyl]-6-hydroxyhexanamide

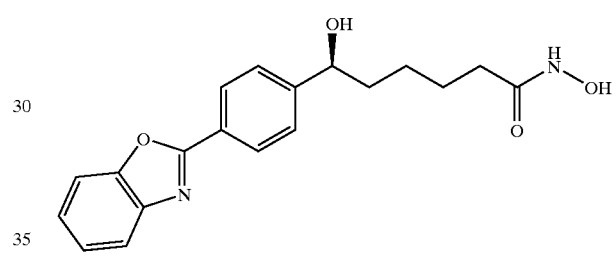

[α]$_D$: –11.5 (c 0.81, methanol),

TLC: Rf 0.21 (chloroform:methanol 9:1),

NMR (d$_6$-DMSO): δ 10.30 (s, 1H), 8.64 (s, 1H), 8.15 (d, J=8.4 Hz, 2H), 7.82–7.75 (m, 2H), 7.55 (d, J=8.4 Hz, 2H), 7.45–7.30 (m, 2H), 5.32 (d, J=4.8 Hz, 1H), 4.65–4.56 (m, 1H), 1.92 (t, J=7.0 Hz, 2H), 1.70–1.20 (m, 6H).

EXAMPLE 14(4)

(S)-(–)-N-hydroxy-6-[4-(5-methylbenzoxazol-2-yl)phenyl]-6-hydroxyhexanamide

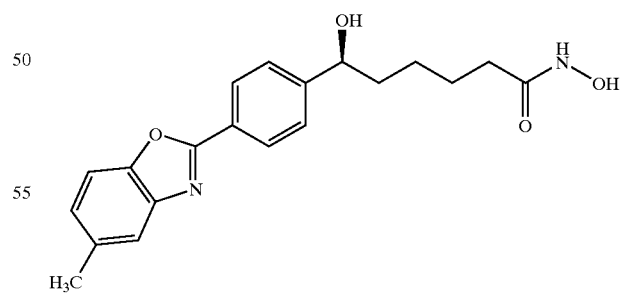

[α]$_D$: –33.4 (c 0.99, dimethylformamide),

TLC: Rf 0.23 (chloroform:methanol=9:1),

NMR (d$_6$-DMSO): δ 10.29 (d, J=1.5 Hz, 1H), 8.63 (d, J=1.5 Hz, 1H), 8.12 (d, J=8.1 Hz, 2H), 7.64 (d, J=8.4 Hz, 1H), 7.58 (d, J=1.2 Hz, 1H), 7.53 (d, J=8.1 Hz, 2H), 7.23 (dd, J=8.4, 1.2 Hz, 1H), 5.32 (d, J=4.2, 1H), 4.60 (m, 1H), 2.43 (s, 3H), 1.91 (t, J=6.9 Hz, 2H), 1.70–1.20 (m, 6H).

EXAMPLE 14(5)

(S)-(−)-N-hydroxy-6-[4-(4-(dimethylaminomethyl)phenyl)phenyl]-6-hydroxyhexanamide.hydrochloride

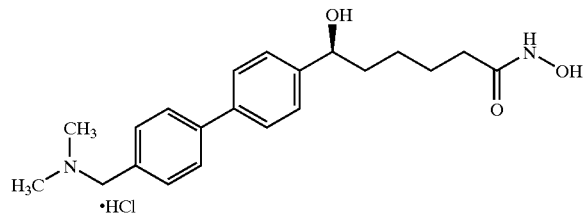

[α]$_D$: −5.39 (c 0.495, water),

TLC: Rf 0.25 (chloroform:methanol=2:1).

NMR (d$_6$-DMSO): δ 10.31 (m, 2H), 8.64 (s, 1H), 7.76 (d, J=8.0 Hz, 2H), 7.65 (d, J=8.0 Hz, 2H), 7.51 (d, J=8.0 Hz, 2H), 7.41 (d, J=8.0 Hz, 2H), 5.16 (m, 1H), 4.53 (m, 1H), 4.29 (s, 2H), 2.71 (s, 6H), 1.91 (t, J=7.0 Hz, 2H), 1.65–1.15 (m, 6H).

EXAMPLE 15

(R)-N-(1-methoxy-1-methyl)ethoxy-6-[4-(4-(morpholin-4-ylmethyl)phenyl)phenyl]-6-hydroxyhexanamide

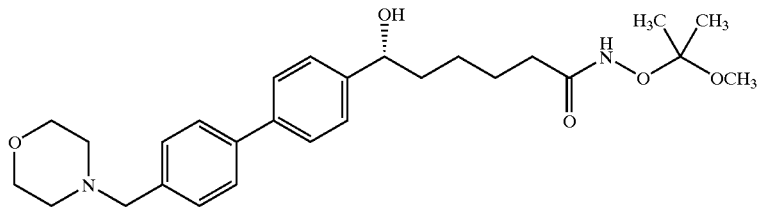

By the same procedure as a series of reactions of reference example 4→reference example 3→example 1 using methyl 6-[4-(4-(morpholin-4-ylmethyl)phenyl)phenyl]-6-oxohexanoate instead of the compound prepared in reference example 1, the compound of the present invention having the following physical data was obtained.

TLC: Rf 0.46 (chloroform:methanol=6:1),

NMR (CDCl$_3$): δ 7.74 (brs, 1H), 7.54 (d, J=8.1 Hz, 2H), 7.53 (d, J=8.1 Hz, 2H), 7.39 (d, J=8.1 Hz, 2H), 7.38 (d, J=8.1 Hz, 2H), 4.74–4.70 (m, 1H), 3.73–3.70 (m, 4H), 3.30 (s, 3H), 2.48–2.45 (m, 4H), 2.19–2.08 (m, 2H), 1.91–1.34 (m, 6H), 1.41 (s, 6H).

EXAMPLE 15(1)

(R)-N-(1-methoxy-1-methyl)ethoxy-4-[4-(4-(dipropylaminomethyl)phenyl)phenyl]-6-hydroxyhexanamide

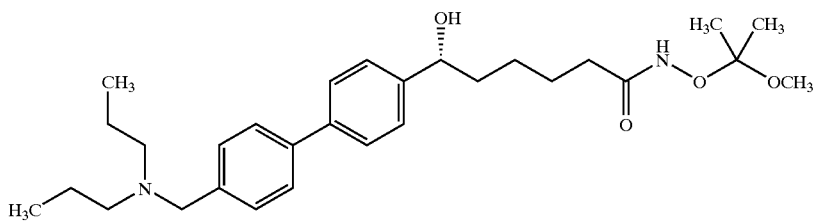

By the same procedure as a series of reactions of example 15 using methyl 6-[4-(4-(dipropylaminomethyl)phenyl)phenyl]-6-oxohexanoate instead of methyl 6-[4-(4-(morpholin-4-ylmethyl)phenyl)phenyl]-6-oxohexanoate, the compound of the present invention having the following physical data was obtained.

TLC: Rf 0.31 (chloroform:methanol=9:1),

NMR (CDCl$_3$): δ 7.76 (br, 1H), 7.57 (d, J=8.4 Hz, 2H), 7.52 (d, J=8.4 Hz, 2H), 7.39 (d, J=8.4 Hz, 4H), 4.72 (dd, J=7.0, 5.8 Hz, 1H), 3.59 (s, 2H), 3.30 (s, 3H), 2.40 (t-like, J=7.5 Hz, 4H), 2.34 (m, 2H), 1.84–1.67 (m, 4H), 1.56–1.36 (m, 2H), 1.50 (m, J=7.5 Hz, 4H), 1.41 (s, 6H), 0.87 (t, J=7.5 Hz, 6H).

EXAMPLE 16

(R)-(+)-N-hydroxy-6-[4-(4-(morpholin-4-ylmethyl)phenyl)phenyl]-6-hydroxyhexanamide.hydrochloride

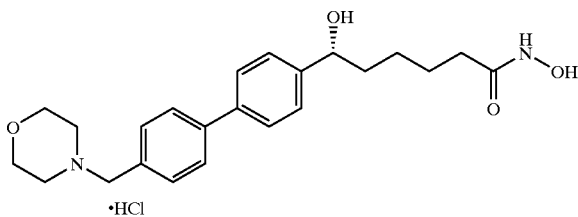

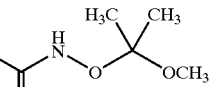

By the same procedure as a series of reactions of example 2 using the compound prepared in example 15 instead of the compound prepared in example 1 and the conversion into the acid addition salts by conventional means., the compound of the present invention having the following physical data was obtained.

[α]$_D$: +6.17 (c 0.12, methanol),

TLC: Rf 0.21 (chloroform:methanol=9:1),

NMR (d$_6$-DMSO): δ 11.30 (brs, 1H), 10.32 (brs, 1H), 7.73 (d, J=8.7 Hz, 2H), 7.67 (d, J=8.7 Hz, 2H), 7.63 (d, J=8.7 Hz, 2H), 7.39 (d, J=8.7 Hz, 2H), 4.52 (t, J=6.3 Hz, 1H), 4.34 (d, J=5.1 Hz, 2H), 3.94–3.75 (m, 4H), 3.20–2.95 (m, 4H), 1.93 (t, J=7.2 Hz, 2H), 1.65–1.15 (m, 6H).

EXAMPLE 16(1)

(R)-(+)-N-hydroxy-6-[4-(4-(dipropylaminomethyl)phenyl)phenyl]-6-hydroxyhexanamide

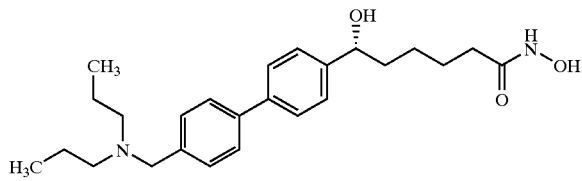

By the same procedure as a series of reactions of example 16 using the compound prepared in example 15(1), or the conversion into the acid addition salts by conventional means, the compounds of the present invention having the following physical data were obtained.

Free Form:
 [α]$_D$: +20.85 (c 1.01, dimethylformamide),
 TLC: Rf 0.37 (chloroform:methanol=6:1),
 NMR (d$_6$-DMSO): δ 10.26 (br, 1H), 8.65 (br, 1H), 7.58 (d, J=8.4 Hz, 4H), 7.36 (d, J=8.4 Hz, 2H), 7.35 (d, J=8.4 Hz, 2H), 5.12 (br, 1H), 4.51 (t, J=6.0 Hz, 1H), 3.52 (s, 2H), 2.33 (t, J=7.2 Hz, 4H), 1.91 (t, J=7.2 Hz, 2H), 1.64–1.55 (m, 2H), 1.51–1.37 (m, 6H), 1.36–1.17 (m, 2H), 0.82 (t, J=7.2 Hz, 6H).

Hydrochloride:
 TLC: Rf 0.37 (chloroform:methanol=6:1),
 NMR (d$_6$-DMSO): δ 10.58 (br, 1H), 10.32 (s, 1H), 8.62 (br, 1H), 7.74 (d, J=8.4 Hz, 2H), 7.68 (d, J=8.4 Hz, 2H), 7.65 (d, J=8.4 Hz, 2H), 7.40 (d, J=8.4 Hz, 2H), 5.17 (br, 1H), 4.53 (t, J=6.3 Hz, 1H), 4.32 (s, 2H), 2.93 (m, 4H), 1.91 (t, J=7.2 Hz, 2H), 1.82–1.66 (m, 4H), 1.65–1.55 (m, 2H), 1.48 (m, 2H), 1.40–1.20 (m, 2H), 0.86 (t, J=7.2 Hz, 6H).

EXAMPLES 17(1) AND 17(2)

By the same procedure as a series of reactions of reference example 4→reference example 3→example 1→example 2 using methyl 6-(5-phenylthiophen-2-yl)-6-oxohexanoate or methyl 6-(5-phenylbenzofuran-2-yl)-6-oxohexanoate instead of the compound prepared in reference example 1, the following compounds of the present invention were obtained.

EXAMPLE 17(1)

(R)-N-hydroxy-6-(5-phenylthiophen-2-yl)-6-hydroxyhexanamide

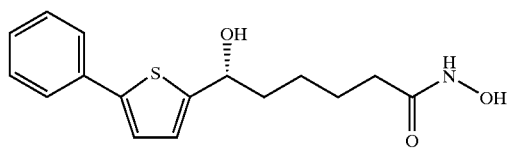

TLC: Rf 0.19 (chloroform:methanol=9:1),
NMR (d$_6$-DMSO): δ 10.42–10.20 (br, 1H), 8.80–8.55 (br, 1H), 7.64–7.56 (m, 2H), 7.43–7.20 (m, 4H), 6.90 (d, J=3.2 Hz, 1H), 5.59 (d, J=4.0 Hz, 1H), 4.80–4.65 (m, 1H), 1.93 (t, J=7.4 Hz, 2H), 1.76–1.15 (m, 6H).

EXAMPLE 17(2)

(R)-N-hydroxy-6-(5-phenylbenzofuran-2-yl)-6-hydroxyhexanamide

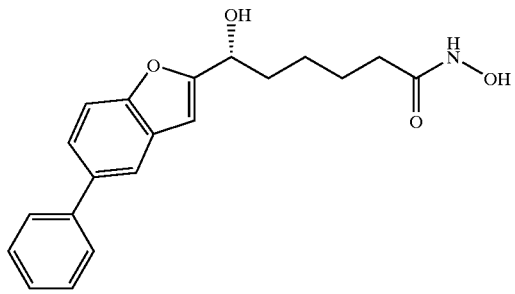

TLC: Rf 0.28 (chloroform:methanol=9:1),
NMR (d$_6$-DMSO): δ 10.31 (s, 1H), 8.65 (s, 1H), 7.83 (m, 1H), 7.70–7.52 (m, 4H), 7.50–7.28 (m, 3H), 6.75 (s, 1H), 5.53 (d, J=5.4 Hz, 1H), 4.72–4.58 (m, 1H), 1.93 (t, J=7.4 Hz, 2H), 1.84–1.62 (m, 2H), 1.60–1.18 (m, 4H).

REFERENCE EXAMPLE 16

(R)-benzyl 6-[4-(4-(methoxycarbonyl)phenyl)phenyl]-6-hydroxyhexanoate

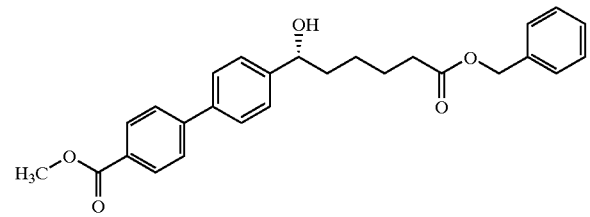

By the same procedure as a series of reactions of reference example 4 using benzyl 6-[4-(4-methoxycarbonyl)phenyl)phenyl]-6-oxohexanoate instead of the compound prepared in reference example 1, the title compound having the following physical data was obtained.

TLC: Rf 0.19 (chloroform:ethyl acetate=19:1).

REFERENCE EXAMPLE 17

(R)-6-[4-(4-(methoxycarbonyl)phenyl)phenyl]-6-hydroxyhexanoic acid

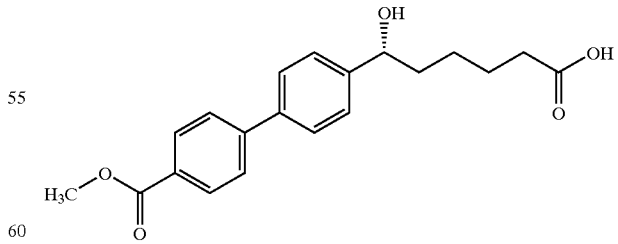

To a solution of the compound prepared in reference example 16 (1.36 g) in methanol (20 mL) and tetrahydrofuran (10 mL) was added 10% palladium carbon (136 mg). Under atmosphere of hydrogen, the reaction mixture was stirred at room temperature for 1.5 hours. The reaction

EXAMPLE 18

(R)-N-hydroxy-6-[4-(4-(methoxycarbonyl)phenyl)phenyl]-6-hydroxyhexanamide

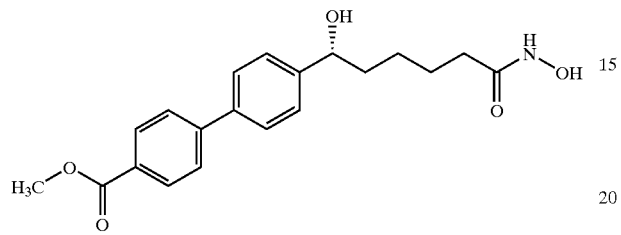

By the same procedure as a series of reactions of example 1→example 2 using the compound prepared in reference example 17, the compound of present invention having the following physical data was obtained.

TLC: Rf 0.28 (chloroform:methanol=9:1),

NMR (d$_6$-DMSO): δ 10.30 (s, 1H), 8.64 (s, 1H), 8.02 (d, J=8.4 Hz, 2H), 7.81 (d, J=8.4 Hz, 2H), 7.68 (d, J=8.4 Hz, 2H), 7.42 (d, J=8.4 Hz, 2H), 5.18 (d, J=4.4 Hz, 2H), 4.61–4.48 (m, 1H), 3.86 (s, 3H), 1.91 (t, J=7.4 Hz, 2H), 1.67–1.10 (m, 6H).

EXAMPLE 19

(R)-N-hydroxy-6-[4-(4-carboxyphenyl)phenyl]-6-hydroxyhexanamide

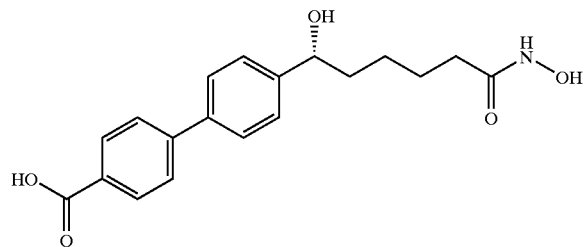

By the same procedure as a series of reactions of example 1→reference example 3→example 2 using the compound prepared in reference example 17, the compound of present invention having the following physical data was obtained.

TLC: Rf 0.16 (chloroform:methanol:acetic acid=90:10:1),

NMR (d$_6$-DMSO): δ 10.31 (s, 1H), 8.00 (d, J=8.4 Hz, 2H), 7.75 (d, J=8.4 Hz, 2H), 7.66 (d, J=8.4 Hz, 2H), 7.41 (d, J=8.4 Hz, 2H), 5.40–4.90 (br. 1H), 4.61–4.47 (m, 1H), 1.92 (t, J=7.0 Hz, 2H), 1.70–1.10 (m, 6H).

REFERENCE EXAMPLE 18

(R)-methyl 6-[4-(4-methylthiophenyl)phenyl]-6-hydroxyhexanoate

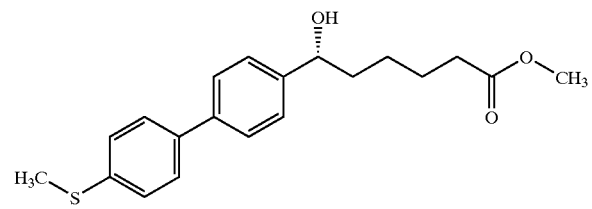

By the same procedure as a series of reactions of reference example 4 using methyl 6-[4-(4-methylthiophenyl)phenyl]-6-oxohexanoate instead of the compound prepared in reference example 1, the title compound having the following physical data was obtained.

TLC: Rf 0.25 (hexane:ethyl acetate=2:1),

NMR (CDCl$_3$): δ 7.57–7.49 (m, 4H), 7.39 (d, J=8.4 Hz, 2H), 7.32 (d, J=8.4 Hz, 2H), 4.72 (t, J=6.2 Hz, 1H), 3.65 (s, 3H), 2.32 (t, J=7.4 Hz, 2H), 1.88–1.25 (m, 6H).

REFERENCE EXAMPLE 19

(R)-methyl 6-[4-(4-methylsulfonylphenyl)phenyl]-6-hydroxyhexanoate

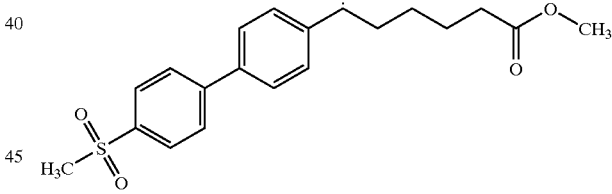

To a solution of the compound prepared in reference example 18 (335 mg) in dichloromethane (10 mL) was added m-chloroperbenzoic acid (504 mg) at 0° C. The reaction mixture was stirred at 0° C. for 1 hour. To the reaction mixture was added an aqueous solution of sodium thiosulfate and the mixture was extracted with ethyl acetate. The extract was washed with water and a saturated aqueous solution of sodium chloride, dried over anhydrous sodium sulfate and concentrated to give the title compound (349 mg) having the following physical data.

TLC: Rf 0.51 (hexane:ethyl acetate=1:4),

NMR (CDCl$_3$): δ 8.00 (d, J=8.4 Hz, 2H), 7.76 (d, J=8.4 Hz, 2H), 7.59 (d, J=8.4 Hz, J=2H), 7.46 (d, J=8.4 Hz, 2H), 4.80–4.72 (m, 1H), 3.66 (s, 3H), 3.09 (s, 3H), 2.32 (t, J=7.5 Hz, 2H), 1.90–1.30 (m, 6H).

EXAMPLE 20

(R)-(+)-N-hydroxy-6-[4-(4-methylsulfonylphenyl)phenyl]-6-hydroxyhexanamide

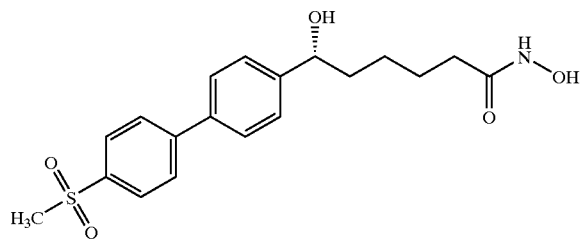

By the same procedure as a series of reactions of reference example 3→example 1→example 2 using the compound prepared in reference example 19 instead of the compound prepared in reference example 2, the compound of the present invention having the following physical data was obtained.

$[\alpha]_D$: +9.84 (c 0.125, methanol),

TLC: Rf 0.12 (chloroform:methanol=9:1),

NMR ($d_6$-DMSO): δ 10.29 (s, 1H), 8.63 (s, 1H), 7.97 (d, J=8.7 Hz, 2H), 7.91 (d, J=8.7 Hz, 2H), 7.69 (d, J=8.7 Hz, 2H), 7.43 (d, J=8.7 Hz, 2H), 5.19 (d, J=4.5 Hz, 1H), 4.59–4.51 (m, 1H), 3.23 (s, 1H), 1.90 (t, J=7.5 Hz, 2H), 1.62–1.18 (m, 6H).

REFERENCE EXAMPLE 20

(R)-methyl 6-[4-(4-hydroxymethylphenyl)phenyl]-6-hydroxyhexanoate

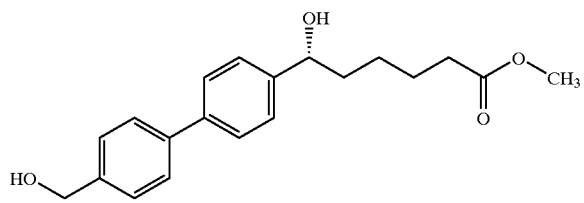

By the same procedure as a series of reactions of reference example 4 using methyl 6-[4-(4-formylphenyl)phenyl]-6-oxohexanoate instead of the compound prepared in reference example 1, the title compound having the following physical data was obtained.

TLC: Rf 0.27 (hexane:ethyl acetate=1:1),

NMR (CDCl$_3$): δ 7.59 (d, J=8.4 Hz, 2H), 7.57 (d, J=8.4 Hz, 2H), 7.44 (d, J=8.4 Hz, 2H), 7.40 (d, J=8.4 Hz, 2H), 4.78–4.66 (m, 3H), 3.66 (s, 3H), 2.32 (t, J=7.6 Hz, 2H), 2.02–1.20 (m, 6H).

EXAMPLE 21

(R)-N-hydroxy-6-[4-(4-hydroxymethylphenyl)phenyl]-6-hydroxyhexanamide

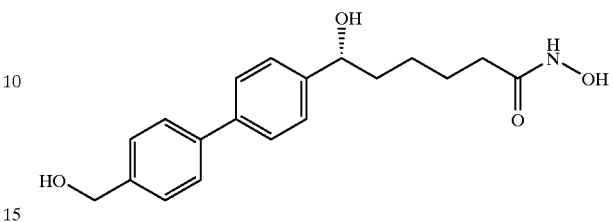

By the same procedure as a series of reactions of reference example 3→example 1→example 2 using the compound prepared in reference example 20 instead of the compound prepared in reference example 2, the compound of the present invention having the following physical data was obtained.

TLC: Rf 0.13 (chloroform:methanol=9:1),

NMR ($d_6$-DMSO): δ 10.30 (s, 1H), 8.80–8.50 (br. 1H), 7.60 (d, J=8.0 Hz, 2H), 7.58 (d, J=8.0 Hz, 2H), 7.37 (d, J=8.0 Hz, 4H), 5.40–5.00 (br, 2H), 4.60–4.40 (m, 3H), 1.91 (t, J=7.0 Hz, 2H), 1.70–1.10 (m, 6H).

EXAMPLE 22

N-methoxy-6-[4-(4-chlorophenyl)phenyl]-6-hydroxyhexanamide

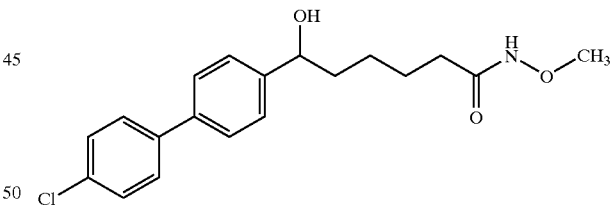

By the same procedure as a series of reactions of example 1 using methoxylamine instead of (1-methoxy-1-methylethyl)hydroxyamine, the compound of the present invention having the following physical data was obtained.

TLC: Rf 0.27 (ethyl acetate),

NMR (CDCl$_3$): δ 8.21 (br, 1H), 7.52 (d, J=8.0 Hz, 2H), 7.49 (d, J=8.0 Hz, 2H), 7.39 (d, J=8.0 Hz, 4H), 4.74–4.70 (m, 1H), 3.72 (s, 3H), 2.44–2.04 (m, 3H), 1.90–1.62 (m, 4H), 1.58–1.34 (m, 2H).

EXAMPLE 23

(R)-(+)-5-(5,5-dimethyl-1,4,2-dioxazolin-3-yl)-1-[4-(5-methylbenzoxazol-2-yl)phenyl]pentan-1-ol

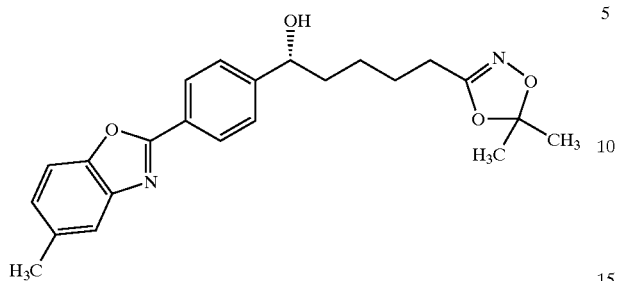

A solution of the compound prepared in example 6 (3 g) in toluene (100 mL) was stirred at 100° C. for 3 hours. The reaction mixture was concentrated. The obtained residue was washed with isopropyl ether and dried to give the compound (2.83 g) of the present invention having the following physical data.

[α]$_D$: +24.59 (c 0.81, dimethylformamide),

TLC: Rf 0.21 (hexane:ethyl acetate=2:1),

NMR (CDCl$_3$): δ 8.21 (d, J=8.4 Hz, 2H), 7.54 (brs, 1H), 7.49 (d, J=8.4 Hz, 2H), 7.45 (d, J=8.4 Hz, 1H), 7.17–7.14 (m, 1H), 4.79–4.75 (m, 1H), 2.48 (s, 3H), 2.30 (t, J=7.2 Hz, 2H), 1.91–1.33 (m, 6H), 1.53 (s, 6H).

EXAMPLES 23(1) AND 23(2)

Using the compound prepared in example 6(3) or (4) instead of the compound prepared in example 6, if desired, the conversion into the acid addition salts by conventional means, the following compounds of the present invention were obtained.

EXAMPLE 23(1)

(R)-5-(5,5-dimethyl-1,4,2-dioxazolin-3-yl)-1-[4-(4-methylthiophenyl)phenyl]pentan-1-ol

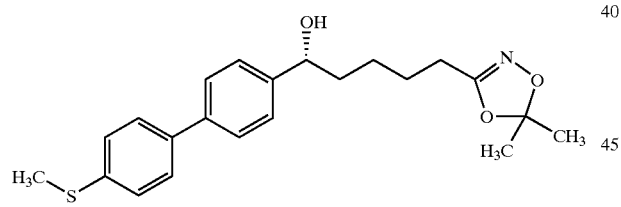

TLC: Rf 0.57 (hexane:ethyl acetate=1:1),

NMR (CDCl$_3$): δ 7.54 (d, J=8.5 Hz, 2H), 7.51 (d, J=8.5 Hz, 2H), 7.39 (d, J=8.5 Hz, 2H), 7.32 (d, J=8.5 Hz, 2H), 4.71 (m, 1H), 2.52 (s, 3H), 2.30 (t, J=7.5 Hz, 2H), 1.94–1.72 (m, 2H), 1.66 (m, 2H), 1.57–1.35 (m, 2H), 1.53 (s, 3H), 1.52 (s, 3H).

EXAMPLE 23(2)

(R)-5-(5,5-dimethyl-1,4,2-dioxazolin-3-yl)-1-[4-(4-(dimethylaminomethyl)phenyl)phenyl]pentan-1-ol.1.5 fumaric acid salt

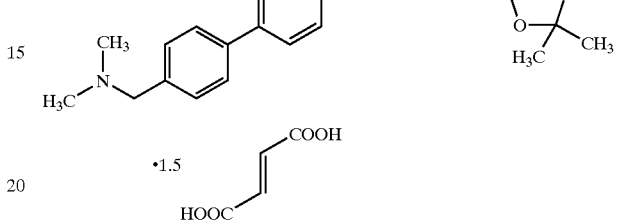

[α]$_D$: +15.9 (c 1.16, dimethylformamide),

TLC: Rf 0.30 (chloroform:methanol=9:1),

NMR (d$_6$-DMSO): δ 7.63 (d, J=8.3 Hz, 2H), 7.60 (d, J=8.3 Hz, 2H), 7.42 (d, J=8.3 Hz, 2H), 7.38 (d, J=8.3 Hz, 2H), 6.57 (s, 3H), 4.54 (t, J=6.0 Hz, 1H), 3.71 (s, 2H), 2.34 (s, 6H), 2.26 (t, J=7.2 Hz, 2H), 1.67–1.23 (m, 6H), 1.43 (s, 6H).

EXAMPLE 24

(R)-N-(1-methoxy-1-methyl)ethoxy-6-[4-(4-(2-(morpholin-4-yl)ethoxy)phenyl)phenyl]-6-hydroxyhexanamide

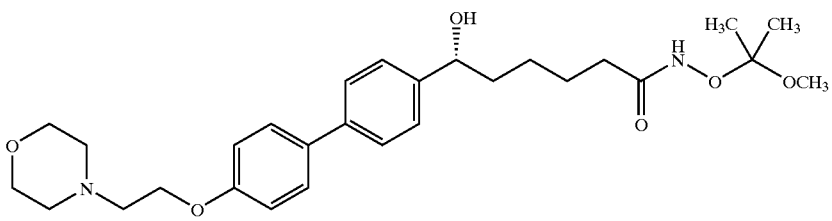

By the same procedure as a series of reactions of reference example 4→reference example 3→example 1 using methyl 6-[4-(4-(2-(morpholin-4-yl)ethoxy)phenyl)phenyl]-6-oxohexanoate instead of the compound prepared in reference example 1, the compound of the present invention having the following physical data was obtained.

TLC: Rf 0.50 (chloroform:methanol=9:1),

NMR (CD$_3$OD): δ 7.52 (d, J=8.7 Hz, 2H), 7.51 (d, J=8.7 Hz, 2H), 7.36 (d, J=J=8.7 Hz, 2H), 7.00 (d, J=8.7 Hz, 2H), 4.62 (t, J=6.6 Hz, 1H), 4.17 (t, J=5.4 Hz, 2H), 3.72 (t, J=4.7 Hz, 4H), 3.28 (s, 3H), 2.82 (t, J=5.4 Hz, 2H), 2.61 (t, J=4.7 Hz, 4H), 2.13 (t, J=7.2 Hz, 2H), 1.86–1.70 (m, 2H), 1.64 (m, 2H), 1.50–1.23 (m, 2H), 1.33 (s, 6H).

EXAMPLE 24(1)

(R)-N-(1-methoxy-1-methyl)ethoxy-6-[4-(4-(2-(morpholin-4-yl)ethyl)phenyl)phenyl]-4-hydroxyhexanamide

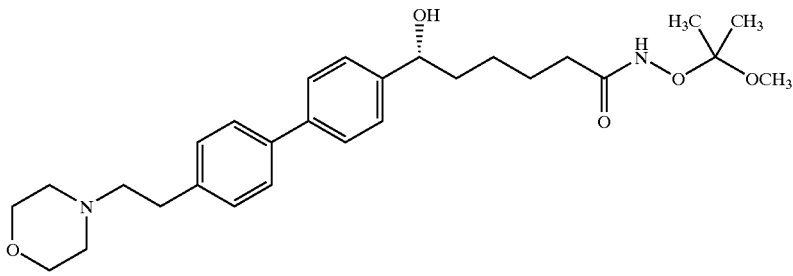

By the same procedure as a series of reactions of example 24 using methyl 6-[4-(4-(2-(morpholin-4-yl)ethyl)phenyl)phenyl]-6-oxohexanoate instead of methyl 6-[4-(4-(2-(morpholin-4-yl)ethoxy)phenyl)phenyl]-6-oxohexanoate, the compound of the present invention having the following physical data was obtained.

TLC: Rf 0.46 (chloroform:methanol=9:1),

NMR (CDCl$_3$): δ 7.70 (brs, 1H), 7.55 (d, J=8.1 Hz, 2H), 7.51 (d, J=8.1 Hz, 2H), 7.39 (d, J=8.1 Hz, 2H), 7.27 (d, J=8.1 Hz, 2H), 4.74–4.69 (m, 1H), 3.77–3.73 (m, 4H), 3.30 (s, 3H), 2.87–2.81 (m, 2H), 2.65–2.60 (m, 2H), 2.55–2.53 (m, 4H), 2.19–1.32 (m, 8H), 1.41 (s, 6H).

EXAMPLE 25

(R)-(+)-N-hydroxy-6-[4-(4-(2-(morpholin-4-yl)ethoxy)phenyl)phenyl]-6-hydroxyhexanamide.hydrochloride

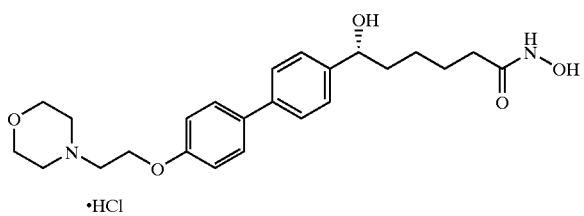

By the same procedure as a series of reactions of example 2 using the compound prepared in example 24 instead of the compound prepared in example 1 and the conversion into the acid addition salts by conventional means., the compound of the present invention having the following physical data was obtained.

[α]$_D$: +13.52 (c 0.84, dimethylformamide),

TLC: Rf 0.31 (chloroform:methanol=9:1),

NMR (d$_6$-DMSO): δ 10.92 (brs, 1H), 10.30 (s, 1H), 8.61 (brs, 1H), 7.61 (d, J=8.4 Hz, 2H), 7.54 (d, J=8.4 Hz, 2H), 7.35 (d, J=8.4 Hz, 2H), 7.07 (d, J=8.4 Hz, 2H), 5.12 (brs, 1H), 4.53–4.41 (m, 3H), 4.01–3.93 (m, 2H), 3.84–3.74 (m, 2H), 3.60–3.12 (m, 6H), 1.90 (t, J=7.2 Hz, 2H), 1.62–1.12 (m, 6H).

EXAMPLE 25(1)

(R)-(+)-N-hydroxy-6-[4-(4-(2-(morpholin-4-yl)ethyl)phenyl)phenyl]-6-hydroxyhexanamide.hydrochloride

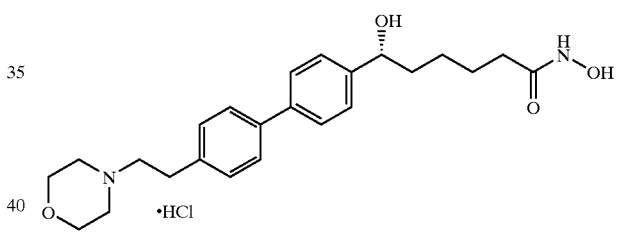

By the same procedure as a series of reactions of example 25 using the compound prepared in example 24(1) or the conversion into the acid addition salts by conventional means, the compound of the present invention having the following physical data was obtained.

[α]$_D$: +16.80 (c 0.815, dimethylformamide),

TLC: Rf 0.41 (chloroform:methanol=17:3),

NMR (d$_6$-DMSO): δ 10.82 (brs, 1H), 10.30 (s, 1H), 8.62 (brs, 1H), 7.62 (d, J=8.4 Hz, 2H), 7.58 (d, J=8.4 Hz, 2H), 7.37 (d, J=8.4 Hz, 2H), 7.34 (d, J=8.4 Hz, 2H), 5.13 (brs, 1H), 4.53–4.49 (m, 1H), 4.00–3.96 (m, 2H), 3.96–3.72 (m, 2H), 3.51–3.47 (m, 2H), 3.39–3.25 (m, 2H), 3.18–3.02 (m, 4H), 1.90 (t, J=7.2 Hz, 2H), 1.64–1.16 (m, 6H).

FORMULATION EXAMPLE
FORMULATION EXAMPLE 1

The following components were admixed in a conventional technique, punched out to give 100 tablets each containing 50 mg of active ingredient.

(R)-(+)-N-hydroxy-6-(4-(4-chlorophenyl)phenyl)-6-hydroxyhexanamide 5.0 g calcium carboxymethylcellulose (disintegrant) 0.2 g magnesium stearate (lubricant) 0.1 g microcrystalline cellulose 4.7 g

FORMULATION EXAMPLE 2

The following components were admixed in a conventional technique. The solution was sterilized in a conventional technique, filled in ampoules 5 ml each and freeze-dried in a conventional technique to give 100 ampoules each containing 20 mg of active ingredient.

(R)-(+)-N-hydroxy-6-(4-(4-chlorophenyl)phenyl)-6-hydroxyhexanamide 2.0 g mannitol 20 g distilled water 500 mL

What is claimed is:

1. A hydroxamic acid derivative of the formula (I):

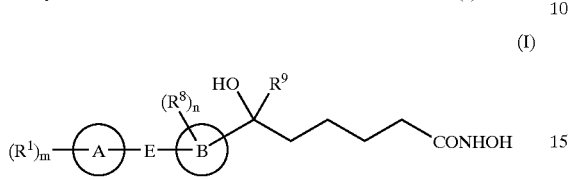

(I)

wherein, $R^1$ is
  (a) C1–8 alkyl,
  (b) C2–8 alkenyl,
  (c) C2–8 alkynyl,
  (o) C1–8 alkyl substituted by —$OR^2$, —$SR^2$, —$NR^3R^4$, —$COR^5$ or Cyc1,
  (u) C1–8 alkyl substituted by —O—(C1–8 alkylene)—$NR^{12}R^{13}$— or —S—(C1–8 alkylene)—$NR^{12}R^{13}$,
  (v) C2–8 alkenyl substituted by —$OR^2$, —$SR^2$, —$NR^3R^4$, —$COR^5$, Cyc1, nitrile, $SO_2R^{10}$, —O—(C1–8 alkylene)—$OR^{11}$, —O—(C1–8 alkylene)—$NR^{12}R^{13}$ or —S—(C1–8 alkylene)—$NR^{12}R^{13}$ or
  (w) C2–8 alkynyl substituted by —$OR^2$, —$SR^2$, —$NR^3R^4$, —$COR^5$, Cyc1, nitrile, —$SO_2R^{10}$, —O—(C1–8 alkylene)—$OR^{11}$, —O—(C1–8 alkylene)—$NR^{12}R^{13}$ or —S—(C1–8 alkylene)—$NR^{12}R^{13}$, $R^2$ is hydrogen, C1–8 alkyl, C2–9 acyl or Cyc1, $R^3$ and $R^4$ are each independently hydrogen, C1–8 alkyl, C2–9 acyl or Cyc1, $R^5$ is hydroxyl, C1–8 alkyl, C1–8 alkoxy, —$NR^6R^7$ or Cyc1, $R^6$ and $R^7$ are each independently hydrogen, C1–8 alkyl or Cyc1, $R^{10}$ is C1–8 alkyl or Cyc1, Cyc1 is morpholine, piperidine or piperazine;

$R^{11}$ is hydrogen, C1–8 alkyl, C2–9 acyl or Cyc1;

$R^{12}$ and $R^{13}$ are each independently hydrogen, C1–8 alkyl, C2–9 acyl or Cyc1;

m is an integer of 1–5;

ring A is a benzene ring;

ring B is a benzene ring;

E is a bond, —CH=CH— or —C≡C—;

$R^8$ is
  (a) C1–8 alkyl,
  (b) C1–8 alkoxy,
  (c) halogen,
  (d) nitro,
  (e) nitrile,
  (f) trifluoromethyl or
  (g) trifluoromethoxy, with the proviso that when E is a bond then, optionally, $R^1$ and $R^8$, taken together, is C1–4 alkylene;

n is 0 or an integer of 1–5;

$R^9$ is hydrogen, C1–8 alkyl, C2–8 alkenyl or C2–8 alkynyl;

a nontoxic salt thereof or a prodrug thereof.

2. The prodrug of a compound of the formula (I) described in claim 1, which is represented by the formula (IA):

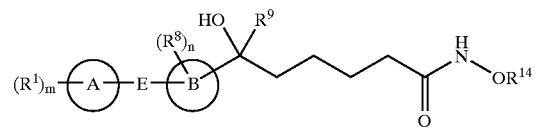

(IA)

wherein, $R^{14}$ is C1–8 alkyl substituted with C1–8 alkyl, C1–8 alkoxy, the other symbols have the same meaning as defined in claim 1.

3. The prodrug of a compound of the formula (I) described in claim 1, which is represented by the formula (IB):

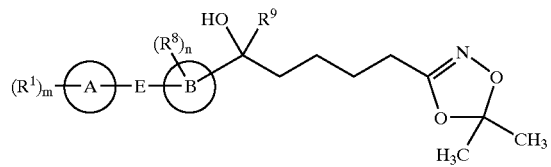

(IB)

wherein, the all symbols have the same meaning as defined in claim 1.

4. The compound described in claim 1, wherein E is a bond.

5. The compound described in claim 1, wherein E is —CH=CH— or —C≡C—.

6. The compound described in claim 1, which is
  (1) (R)-N-hydroxy-6-[4-(4-(piperidin-1-ylmethyl)phenyl)phenyl]-6-hydroxyhexanamide,
  (2) (R)-N-hydroxy-6-[4-(4-(morpholin-4-ylmethyl)phenyl)phenyl]-6-hydroxyhexanamide,
  (3) (R)-N-hydroxy-6-[4-((2-(morpholin-4-yl)ethoxy)phenyl)phenyl]-6-hydroxyhexanamide,
  (4) (R)-N-hydroxy-6-[4-(4-(2-(morpholin-4-yl)ethyl)phenyl)phenyl]-6-hydroxyhexanamide
or a nontoxic salt thereof.

7. The compound described in claim 2, which is:
  (1) (R)-N-(1-methoxy-1-methyl)ethoxy-6-[4-(4-(morpholin-4-ylmethyl)phenyl)phenyl]-6-hydroxyhexanamide,
  (2) (R)-N-(1-methoxy-1-methyl)ethoxy-6-[4-(4-(morpholin-4-yl)ethoxy)phenyl)phenyl]-6-hydroxyhexanamide,
  (3) (R)-N-(1-methoxy-1-methyl)ethoxy-6-[4-(4-(morpholin-4-yl)ethyl)phenyl)phenyl]-6-hydroxyhexanamide,
or a nontoxic salt thereof.

* * * * *